(12) United States Patent
Isaacson et al.

(10) Patent No.: US 11,559,665 B2
(45) Date of Patent: Jan. 24, 2023

(54) MIDLINE CATHETER PLACEMENT DEVICE

(71) Applicant: Becton, Dickinson and Company, Franklin Lakes, NJ (US)

(72) Inventors: Shawn Ray Isaacson, Layton, UT (US); Weston Finch Harding, Lehi, UT (US); Charles D. Shermer, Raleigh, NC (US); Daniel M. Stipe, Raleigh, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/996,769

(22) Filed: Aug. 18, 2020

(65) Prior Publication Data
US 2021/0052858 A1 Feb. 25, 2021

Related U.S. Application Data

(60) Provisional application No. 62/888,946, filed on Aug. 19, 2019.

(51) Int. Cl.
*A61M 25/06* (2006.01)
*A61M 25/00* (2006.01)

(52) U.S. Cl.
CPC .... *A61M 25/0606* (2013.01); *A61M 25/0097* (2013.01)

(58) Field of Classification Search
CPC .......... A61M 25/0606; A61M 25/0113; A61M 2005/1585; A61M 25/0097; A61M 5/14;
(Continued)

(56) References Cited

U.S. PATENT DOCUMENTS 2,211,975 A 8/1940 Hendrickson
2,259,488 A 10/1941 Raiche
(Continued)

FOREIGN PATENT DOCUMENTS

AU 710967 B2 9/1999
CN 1178707 A 4/1998
(Continued)

OTHER PUBLICATIONS

PCT/US2019/021231 filed Mar. 7, 2019 International Search Report and Written Opinion, dated Jun. 27, 2019.
(Continued)

*Primary Examiner* — Theodore J Stigell
*Assistant Examiner* — Rachel T. Smith
(74) *Attorney, Agent, or Firm* — Rutan & Tucker LLP

(57) ABSTRACT

A catheter insertion device is provided for positioning and inserting a catheter, particularly a midline catheter into a patient. The insertion device includes an actuator assembly movable with respect to a housing for deploying the catheter over a needle. A step-wise movement of the actuator advances a catheter assembly, including the catheter, in stages over the introducer needle. An indexing finger of the catheter assembly engages the actuator body during distal advancement of the actuator, and deflects as the actuator is moved proximally. The device further includes a lockout device such as a button, collar, slider, or tab, which allows movement of the catheter relative to the needle but prevents advancement of the catheter to the first stage of the step-wise movement.

16 Claims, 14 Drawing Sheets

(58) Field of Classification Search
CPC .......... A61M 5/158; A61M 2005/1587; A61B 17/3403
See application file for complete search history.

(56) References Cited

U.S. PATENT DOCUMENTS

| | | |
|---|---|---|
| 2,330,400 A | 9/1943 | Winder |
| D138,589 S | 8/1944 | Brandenburg |
| 3,185,151 A | 5/1965 | Czorny |
| 3,297,030 A | 1/1967 | Czorny et al. |
| 3,416,567 A | 12/1968 | von Dardel et al. |
| 3,469,579 A | 9/1969 | Hubert |
| 3,500,828 A | 3/1970 | Podhora |
| 3,552,384 A | 1/1971 | Pierie et al. |
| 3,572,334 A | 3/1971 | Petterson |
| 3,585,996 A | 6/1971 | Reynolds et al. |
| 3,589,361 A | 6/1971 | Loper et al. |
| 3,592,192 A | 7/1971 | Harautuneian |
| 3,595,230 A | 7/1971 | Suyeoka et al. |
| 3,610,240 A | 10/1971 | Harautuneian |
| 3,682,173 A | 8/1972 | Center |
| 3,766,916 A | 10/1973 | Moorehead et al. |
| 3,884,242 A | 5/1975 | Bazell et al. |
| 3,921,631 A | 11/1975 | Thompson |
| 3,995,628 A | 12/1976 | Gula et al. |
| 4,027,668 A | 6/1977 | Dunn |
| 4,037,600 A | 7/1977 | Poncy et al. |
| 4,079,738 A | 3/1978 | Dunn et al. |
| 4,106,506 A | 8/1978 | Koehn et al. |
| 4,177,809 A | 12/1979 | Moorehead |
| 4,292,970 A | 10/1981 | Hession, Jr. |
| 4,317,445 A | 3/1982 | Robinson |
| 4,345,602 A | 8/1982 | Yoshimura et al. |
| 4,354,491 A | 10/1982 | Marbry |
| 4,368,730 A | 1/1983 | Sharrock |
| 4,387,879 A | 6/1983 | Tauschinski |
| 4,417,886 A | 11/1983 | Frankhouser et al. |
| 4,449,693 A | 5/1984 | Gereg |
| 4,456,017 A | 6/1984 | Miles |
| 4,464,171 A | 8/1984 | Garwin |
| 4,509,534 A | 4/1985 | Tassin, Jr. |
| 4,509,945 A | 4/1985 | Kramann et al. |
| 4,511,359 A | 4/1985 | Vaillancourt |
| 4,512,766 A | 4/1985 | Vailancourt |
| 4,525,157 A | 6/1985 | Vaillancourt |
| 4,581,019 A | 4/1986 | Curelaru et al. |
| 4,585,440 A | 4/1986 | Tchervenkov et al. |
| D287,877 S | 1/1987 | Holewinski et al. |
| 4,728,322 A | 3/1988 | Walker et al. |
| 4,738,659 A | 4/1988 | Sleiman |
| 4,747,831 A | 5/1988 | Kulli |
| 4,767,407 A | 8/1988 | Foran |
| 4,772,264 A | 9/1988 | Cragg |
| 4,772,267 A | 9/1988 | Brown |
| 4,781,703 A | 11/1988 | Walker et al. |
| 4,792,531 A | 12/1988 | Kakihana |
| 4,798,193 A | 1/1989 | Giesy et al. |
| 4,813,934 A | 3/1989 | Engelson et al. |
| 4,826,070 A | 5/1989 | Kakihana |
| 4,828,547 A | 5/1989 | Sahi et al. |
| 4,834,708 A | 5/1989 | Pillari |
| 4,834,718 A | 5/1989 | McDonald |
| 4,840,613 A | 6/1989 | Balbierz |
| 4,840,622 A | 6/1989 | Hardy |
| 4,842,591 A | 6/1989 | Luther |
| 4,846,812 A | 7/1989 | Walker et al. |
| 4,850,961 A | 7/1989 | Wanderer et al. |
| 4,860,757 A | 8/1989 | Lynch et al. |
| 4,869,259 A | 9/1989 | Elkins |
| D304,079 S | 10/1989 | McFarlane |
| 4,871,358 A | 10/1989 | Gold |
| 4,874,377 A | 10/1989 | Newgard et al. |
| 4,883,461 A | 11/1989 | Sawyer |
| 4,883,699 A | 11/1989 | Aniuk et al. |
| 4,894,052 A | 1/1990 | Crawford |
| 4,895,346 A | 1/1990 | Steigerwald |
| 4,900,307 A | 2/1990 | Kulli |
| 4,906,956 A | 3/1990 | Kakihana |
| 4,908,021 A | 3/1990 | McFarlane |
| 4,909,793 A | 3/1990 | Vining et al. |
| 4,911,691 A | 3/1990 | Aniuk et al. |
| 4,913,704 A | 4/1990 | Kurimoto |
| 4,917,102 A | 4/1990 | Miller et al. |
| 4,917,668 A | 4/1990 | Haindl |
| 4,917,671 A | 4/1990 | Chang |
| 4,929,235 A | 5/1990 | Merry et al. |
| 4,935,010 A | 6/1990 | Cox et al. |
| 4,944,725 A | 7/1990 | McDonald |
| 4,944,728 A | 7/1990 | Carrell et al. |
| 4,955,863 A | 9/1990 | Walker et al. |
| 4,961,729 A | 10/1990 | Vaillancourt |
| 4,966,586 A | 10/1990 | Vaillancourt |
| 4,966,589 A | 10/1990 | Kaufman |
| 4,994,042 A | 2/1991 | Vadher |
| 4,994,047 A | 2/1991 | Walker et al. |
| 4,995,866 A | 2/1991 | Amplatz et al. |
| 5,007,901 A | 4/1991 | Shields |
| 5,009,642 A | 4/1991 | Sahi |
| 5,019,048 A | 5/1991 | Margolin |
| 5,019,049 A | 5/1991 | Haining |
| D318,733 S | 7/1991 | Wyzgala |
| 5,034,347 A | 7/1991 | Kakihana |
| 5,047,013 A | 9/1991 | Rossdeutscher |
| D321,250 S | 10/1991 | Jepson et al. |
| 5,053,014 A | 10/1991 | Van Heugten |
| 5,054,501 A | 10/1991 | Chuttani et al. |
| 5,061,254 A | 10/1991 | Karakelle et al. |
| 5,064,416 A | 11/1991 | Newgard et al. |
| 5,078,694 A | 1/1992 | Wallace |
| 5,078,696 A | 1/1992 | Nedbaluk |
| 5,078,702 A | 1/1992 | Pomeranz |
| 5,084,023 A | 1/1992 | Lemieux |
| 5,085,645 A | 2/1992 | Purdy et al. |
| 5,088,984 A | 2/1992 | Fields |
| 5,093,692 A | 3/1992 | Su et al. |
| 5,098,392 A | 3/1992 | Fleischhacker et al. |
| 5,098,395 A | 3/1992 | Fields |
| 5,098,396 A | 3/1992 | Taylor et al. |
| 5,098,405 A | 3/1992 | Peterson et al. |
| 5,108,375 A | 4/1992 | Harrison et al. |
| 5,108,376 A | 4/1992 | Bonaldo |
| 5,112,312 A | 5/1992 | Luther |
| 5,116,323 A | 5/1992 | Kreuzer et al. |
| 5,120,317 A | 6/1992 | Luther |
| 5,125,906 A | 6/1992 | Fleck |
| 5,135,487 A | 8/1992 | Morrill et al. |
| 5,137,515 A | 8/1992 | Hogan |
| 5,149,326 A | 9/1992 | Woodgrift et al. |
| 5,154,703 A | 10/1992 | Bonaldo |
| 5,156,590 A | 10/1992 | Vilmar |
| 5,156,596 A | 10/1992 | Balbierz et al. |
| 5,158,544 A | 10/1992 | Weinstein |
| 5,167,637 A | 12/1992 | Okada et al. |
| 5,176,650 A | 1/1993 | Haining |
| 5,186,168 A | 2/1993 | Spofford et al. |
| 5,186,712 A | 2/1993 | Kelso et al. |
| 5,188,607 A | 2/1993 | Wu |
| 5,190,528 A | 3/1993 | Fonger et al. |
| 5,192,301 A | 3/1993 | Kamiya et al. |
| 5,195,974 A | 3/1993 | Hardy |
| 5,195,980 A | 3/1993 | Catlin |
| 5,195,985 A | 3/1993 | Hall |
| 5,205,830 A | 4/1993 | Dassa et al. |
| 5,215,527 A | 6/1993 | Beck et al. |
| 5,215,528 A | 6/1993 | Purdy et al. |
| 5,217,435 A | 6/1993 | Kring |
| 5,219,335 A | 6/1993 | Willard et al. |
| 5,221,255 A | 6/1993 | Mahurkar et al. |
| 5,222,944 A | 6/1993 | Harris |
| 5,225,369 A | 7/1993 | Su et al. |
| 5,226,899 A | 7/1993 | Lee et al. |
| D338,955 S | 8/1993 | Gresl et al. |
| 5,234,410 A | 8/1993 | Graham et al. |
| 5,242,411 A | 9/1993 | Yamamoto et al. |

(56) References Cited

U.S. PATENT DOCUMENTS

| | | |
|---|---|---|
| 5,246,426 A | 9/1993 | Lewis et al. |
| 5,246,430 A | 9/1993 | MacFarlane |
| 5,254,107 A | 10/1993 | Soltesz |
| 5,257,980 A | 11/1993 | Van Antwerp et al. |
| 5,267,982 A | 12/1993 | Sylvanowicz |
| 5,269,771 A | 12/1993 | Thomas et al. |
| D345,419 S | 3/1994 | Horrigan et al. |
| 5,290,310 A | 3/1994 | Makower et al. |
| 5,297,546 A | 3/1994 | Spofford et al. |
| 5,312,359 A | 5/1994 | Wallace |
| 5,312,361 A | 5/1994 | Zadini et al. |
| 5,312,363 A | 5/1994 | Ryan et al. |
| 5,320,608 A | 6/1994 | Gerrone |
| 5,322,517 A | 6/1994 | Sircom et al. |
| 5,330,435 A | 7/1994 | Vaillancourt |
| 5,334,159 A | 8/1994 | Turkel |
| 5,338,311 A | 8/1994 | Mahurkar |
| 5,352,205 A | 10/1994 | Dales et al. |
| 5,358,796 A | 10/1994 | Nakamura et al. |
| 5,366,441 A | 11/1994 | Crawford |
| 5,368,661 A | 11/1994 | Nakamura et al. |
| D353,668 S | 12/1994 | Banks et al. |
| 5,376,082 A | 12/1994 | Phelps |
| 5,376,094 A | 12/1994 | Kline |
| 5,380,290 A | 1/1995 | Makower et al. |
| 5,380,292 A | 1/1995 | Wilson |
| 5,395,341 A | 3/1995 | Slater |
| 5,397,311 A | 3/1995 | Walker et al. |
| 5,405,323 A | 4/1995 | Rogers et al. |
| 5,415,177 A | 5/1995 | Zadini et al. |
| 5,415,645 A | 5/1995 | Friend et al. |
| 5,419,766 A | 5/1995 | Chang et al. |
| 5,419,777 A | 5/1995 | Hofling |
| 5,423,760 A | 6/1995 | Yoon |
| 5,425,718 A | 6/1995 | Tay et al. |
| 5,431,506 A | 7/1995 | Masunaga |
| 5,439,449 A | 8/1995 | Mapes et al. |
| 5,445,625 A | 8/1995 | Voda |
| 5,454,785 A | 10/1995 | Smith |
| 5,454,790 A | 10/1995 | Dubrul |
| 5,456,258 A | 10/1995 | Kondo et al. |
| 5,456,668 A | 10/1995 | Ogle, II |
| 5,458,658 A | 10/1995 | Sircom |
| 5,466,230 A | 11/1995 | Davila |
| 5,480,389 A | 1/1996 | McWha et al. |
| 5,482,395 A | 1/1996 | Gasparini |
| 5,484,419 A | 1/1996 | Fleck |
| 5,487,734 A | 1/1996 | Thorne et al. |
| 5,489,273 A | 2/1996 | Whitney et al. |
| 5,496,281 A | 3/1996 | Krebs |
| 5,501,671 A | 3/1996 | Rosen et al. |
| 5,501,675 A | 3/1996 | Erskine |
| 5,507,300 A | 4/1996 | Mukai et al. |
| 5,512,052 A | 4/1996 | Jesch |
| 5,514,108 A | 5/1996 | Stevens |
| 5,520,655 A | 5/1996 | Davila et al. |
| 5,520,657 A | 5/1996 | Sellers et al. |
| D371,195 S | 6/1996 | Krebs |
| 5,522,807 A | 6/1996 | Luther |
| 5,527,290 A | 6/1996 | Zadini et al. |
| 5,527,291 A | 6/1996 | Zadini et al. |
| 5,531,701 A | 7/1996 | Luther |
| 5,531,713 A | 7/1996 | Mastronardi et al. |
| 5,533,988 A | 7/1996 | Dickerson et al. |
| 5,535,785 A | 7/1996 | Werge et al. |
| 5,542,933 A | 8/1996 | Marks |
| 5,554,136 A | 9/1996 | Luther |
| 5,562,629 A | 10/1996 | Haughton et al. |
| 5,562,630 A | 10/1996 | Nichols |
| 5,562,631 A | 10/1996 | Bogert |
| 5,562,633 A | 10/1996 | Wozencroft |
| 5,562,634 A | 10/1996 | Flumene et al. |
| 5,569,202 A | 10/1996 | Kovalic et al. |
| 5,569,217 A | 10/1996 | Luther |
| 5,571,073 A | 11/1996 | Castillo |
| 5,573,510 A | 11/1996 | Isaacson |
| 5,575,777 A | 11/1996 | Cover et al. |
| 5,591,194 A | 1/1997 | Berthiaume |
| 5,599,291 A | 2/1997 | Balbierz et al. |
| 5,599,327 A | 2/1997 | Sugahara et al. |
| 5,609,583 A | 3/1997 | Hakki et al. |
| 5,613,663 A | 3/1997 | Schmidt et al. |
| 5,613,954 A | 3/1997 | Nelson et al. |
| 5,630,802 A | 5/1997 | Moellmann et al. |
| 5,630,823 A | 5/1997 | Schmitz-Rode et al. |
| 5,634,475 A | 6/1997 | Wolvek |
| 5,634,913 A | 6/1997 | Stinger |
| 5,637,091 A | 6/1997 | Hakky et al. |
| 5,645,076 A | 7/1997 | Yoon |
| 5,651,772 A | 7/1997 | Arnett |
| D383,538 S | 9/1997 | Erskine et al. |
| 5,662,622 A | 9/1997 | Gore et al. |
| 5,674,241 A | 10/1997 | Bley et al. |
| 5,676,658 A | 10/1997 | Erskine |
| 5,683,368 A | 11/1997 | Schmidt |
| 5,683,370 A | 11/1997 | Luther et al. |
| 5,685,855 A | 11/1997 | Erskine |
| 5,685,858 A | 11/1997 | Kawand |
| 5,685,860 A | 11/1997 | Chang et al. |
| 5,688,249 A | 11/1997 | Chang et al. |
| 5,693,025 A | 12/1997 | Stevens |
| 5,695,474 A | 12/1997 | Daugherty |
| 5,697,914 A | 12/1997 | Brimhall |
| 5,700,250 A | 12/1997 | Erskine |
| 5,702,367 A | 12/1997 | Cover et al. |
| 5,702,369 A | 12/1997 | Mercereau |
| 5,704,914 A | 1/1998 | Stocking et al. |
| 5,722,425 A | 3/1998 | Bostrom |
| 5,725,503 A | 3/1998 | Arnett |
| 5,730,150 A | 3/1998 | Peppel et al. |
| 5,730,733 A | 3/1998 | Mortier et al. |
| 5,730,741 A | 3/1998 | Horzewski et al. |
| 5,738,144 A | 4/1998 | Rogers |
| 5,738,660 A | 4/1998 | Luther |
| 5,743,882 A | 4/1998 | Luther |
| 5,743,888 A | 4/1998 | Wilkes et al. |
| 5,749,371 A | 5/1998 | Zadini et al. |
| 5,749,857 A | 5/1998 | Cuppy |
| 5,749,861 A | 5/1998 | Guala et al. |
| 5,750,741 A | 5/1998 | Crocker et al. |
| 5,755,693 A | 5/1998 | Walker et al. |
| 5,755,709 A | 5/1998 | Cuppy |
| 5,762,630 A | 6/1998 | Bley et al. |
| 5,762,636 A | 6/1998 | Rupp et al. |
| 5,765,682 A | 6/1998 | Bley et al. |
| 5,779,679 A | 7/1998 | Shaw |
| 5,779,680 A | 7/1998 | Yoon |
| 5,779,681 A | 7/1998 | Bonn |
| 5,782,807 A | 7/1998 | Falvai et al. |
| D397,434 S | 8/1998 | Pike |
| 5,792,124 A | 8/1998 | Horrigan et al. |
| 5,800,395 A | 9/1998 | Botich et al. |
| 5,807,339 A | 9/1998 | Bostrom et al. |
| 5,807,342 A | 9/1998 | Musgrave et al. |
| 5,807,350 A | 9/1998 | Diaz |
| 5,810,780 A | 9/1998 | Brimhall et al. |
| 5,810,835 A | 9/1998 | Ryan et al. |
| 5,813,411 A | 9/1998 | Van Bladel et al. |
| 5,817,058 A | 10/1998 | Shaw |
| 5,817,069 A | 10/1998 | Arnett |
| 5,824,001 A | 10/1998 | Erskine |
| 5,827,202 A | 10/1998 | Miraki et al. |
| 5,827,221 A | 10/1998 | Phelps |
| 5,827,227 A | 10/1998 | DeLago |
| 5,830,190 A | 11/1998 | Howell |
| 5,830,224 A | 11/1998 | Cohn et al. |
| 5,839,470 A | 11/1998 | Hiejima et al. |
| 5,843,002 A | 12/1998 | Pecor et al. |
| 5,843,038 A | 12/1998 | Bailey |
| 5,846,259 A | 12/1998 | Berthiaume |
| 5,851,196 A | 12/1998 | Arnett |
| 5,853,393 A | 12/1998 | Bogert |
| 5,855,615 A | 1/1999 | Bley et al. |
| 5,858,002 A | 1/1999 | Jesch |

(56) References Cited

U.S. PATENT DOCUMENTS

| | | |
|---|---|---|
| 5,865,806 A | 2/1999 | Howell |
| 5,873,864 A | 2/1999 | Luther et al. |
| 5,879,332 A | 3/1999 | Schwemberger et al. |
| 5,879,337 A | 3/1999 | Kuracina et al. |
| 5,885,217 A | 3/1999 | Gisselberg et al. |
| 5,885,251 A | 3/1999 | Luther |
| 5,891,098 A | 4/1999 | Huang |
| 5,891,105 A | 4/1999 | Mahurkar |
| 5,895,398 A | 4/1999 | Wensel et al. |
| 5,902,274 A | 5/1999 | Yamamoto et al. |
| 5,902,832 A | 5/1999 | Van Bladel et al. |
| 5,911,705 A | 6/1999 | Howell |
| 5,911,710 A | 6/1999 | Barry et al. |
| 5,913,848 A | 6/1999 | Luther et al. |
| 5,916,208 A | 6/1999 | Luther et al. |
| 5,928,199 A | 7/1999 | Nakagami |
| D413,382 S | 8/1999 | Maissami |
| 5,935,110 A | 8/1999 | Brimhall |
| 5,941,854 A | 8/1999 | Bhitiyakul |
| 5,944,690 A | 8/1999 | Falwell et al. |
| 5,947,930 A | 9/1999 | Schwemberger et al. |
| 5,951,520 A | 9/1999 | Buizynski et al. |
| 5,954,698 A | 9/1999 | Pike |
| 5,957,893 A | 9/1999 | Luther et al. |
| 5,964,744 A | 10/1999 | Balbierz et al. |
| 5,967,490 A | 10/1999 | Pike |
| 5,984,895 A | 11/1999 | Padilla et al. |
| 5,984,903 A | 11/1999 | Nadal |
| 5,989,220 A | 11/1999 | Shaw et al. |
| 5,989,271 A | 11/1999 | Bonnette et al. |
| 5,997,507 A | 12/1999 | Dysarz |
| 5,997,510 A | 12/1999 | Schwemberger |
| 6,001,080 A | 12/1999 | Kuracina et al. |
| 6,004,278 A | 12/1999 | Botich et al. |
| 6,004,294 A | 12/1999 | Brimhall et al. |
| 6,004,295 A | 12/1999 | Langer et al. |
| 6,011,988 A | 1/2000 | Lynch et al. |
| 6,019,736 A | 2/2000 | Avellanet et al. |
| 6,022,319 A | 2/2000 | Willard et al. |
| 6,024,727 A | 2/2000 | Thorne et al. |
| 6,024,729 A | 2/2000 | Dehdashtian et al. |
| 6,045,734 A | 4/2000 | Luther et al. |
| 6,056,726 A | 5/2000 | Isaacson |
| 6,059,484 A | 5/2000 | Greive |
| 6,066,100 A | 5/2000 | Willard et al. |
| 6,074,378 A | 6/2000 | Mouri et al. |
| 6,077,244 A | 6/2000 | Botich et al. |
| 6,080,137 A | 6/2000 | Pike |
| 6,083,237 A | 7/2000 | Huitema et al. |
| 6,096,004 A | 8/2000 | Meglan et al. |
| 6,096,005 A | 8/2000 | Botich et al. |
| 6,109,264 A | 8/2000 | Sauer |
| 6,117,108 A | 9/2000 | Woehr et al. |
| 6,120,494 A | 9/2000 | Jonkman |
| 6,126,633 A | 10/2000 | Kaji et al. |
| 6,126,641 A | 10/2000 | Shields |
| 6,139,532 A | 10/2000 | Howell et al. |
| 6,139,557 A | 10/2000 | Passafaro et al. |
| 6,159,179 A | 12/2000 | Simonson |
| 6,171,234 B1 | 1/2001 | White et al. |
| 6,171,287 B1 | 1/2001 | Lynn et al. |
| 6,176,842 B1 | 1/2001 | Tachibana et al. |
| 6,193,690 B1 | 2/2001 | Dysarz |
| 6,197,001 B1 | 3/2001 | Wilson et al. |
| 6,197,007 B1 | 3/2001 | Thorne et al. |
| 6,197,041 B1 | 3/2001 | Shichman et al. |
| 6,203,527 B1 | 3/2001 | Zadini et al. |
| 6,213,978 B1 | 4/2001 | Voyten |
| 6,217,558 B1 | 4/2001 | Zadini et al. |
| 6,221,047 B1 | 4/2001 | Greene et al. |
| 6,221,048 B1 | 4/2001 | Phelps |
| 6,221,049 B1 | 4/2001 | Selmon et al. |
| 6,224,569 B1 | 5/2001 | Brimhall |
| 6,228,060 B1 | 5/2001 | Howell |
| 6,228,062 B1 | 5/2001 | Howell et al. |
| 6,228,073 B1 | 5/2001 | Noone et al. |
| 6,245,045 B1 | 6/2001 | Stratienko |
| 6,251,092 B1 | 6/2001 | Qin et al. |
| 6,268,399 B1 | 7/2001 | Hultine et al. |
| 6,270,480 B1 | 8/2001 | Dorr et al. |
| 6,273,871 B1 | 8/2001 | Davis et al. |
| 6,280,419 B1 | 8/2001 | Vojtasek |
| 6,287,278 B1 | 9/2001 | Woehr et al. |
| 6,309,379 B1 | 10/2001 | Willard et al. |
| 6,319,244 B2 | 11/2001 | Suresh et al. |
| 6,322,537 B1 | 11/2001 | Chang |
| D452,003 S | 12/2001 | Niermann |
| 6,325,781 B1 | 12/2001 | Takagi et al. |
| 6,325,797 B1 | 12/2001 | Stewart et al. |
| 6,336,914 B1 | 1/2002 | Gillespie, III |
| 6,352,520 B1 | 3/2002 | Miyazaki |
| 6,368,337 B1 | 4/2002 | Kieturakis et al. |
| 6,379,333 B1 | 4/2002 | Brimhall et al. |
| 6,379,372 B1 | 4/2002 | Dehdashtian et al. |
| D457,955 S | 5/2002 | Bilitz |
| 6,406,442 B1 | 6/2002 | McFann et al. |
| D460,179 S | 7/2002 | Isoda et al. |
| 6,422,989 B1 | 7/2002 | Hektner |
| 6,436,070 B1 | 8/2002 | Botich et al. |
| 6,436,112 B2 | 8/2002 | Wensel et al. |
| 6,443,929 B1 | 9/2002 | Kuracina et al. |
| 6,451,052 B1 | 9/2002 | Burmeister et al. |
| 6,461,362 B1 | 10/2002 | Halseth et al. |
| 6,475,217 B1 | 11/2002 | Platt |
| 6,478,779 B1 | 11/2002 | Hu |
| 6,485,473 B1 | 11/2002 | Lynn |
| 6,485,497 B2 | 11/2002 | Wensel et al. |
| 6,497,681 B1 | 12/2002 | Brenner |
| 6,506,181 B2 | 1/2003 | Meng et al. |
| 6,514,236 B1 | 2/2003 | Stratienko |
| 6,524,276 B1 | 2/2003 | Halseth et al. |
| D471,980 S | 3/2003 | Caizza |
| 6,527,759 B1 | 3/2003 | Tachibana et al. |
| 6,530,913 B1 | 3/2003 | Giba et al. |
| 6,530,935 B2 | 3/2003 | Wensel et al. |
| 6,540,725 B1 | 4/2003 | Ponzi |
| 6,540,732 B1 | 4/2003 | Botich et al. |
| 6,544,239 B2 | 4/2003 | Kinsey et al. |
| 6,547,762 B1 | 4/2003 | Botich et al. |
| 6,558,355 B1 | 5/2003 | Metzger et al. |
| 6,582,402 B1 | 6/2003 | Erskine |
| 6,582,440 B1 | 6/2003 | Brumbach |
| 6,585,703 B1 | 7/2003 | Kassel et al. |
| 6,589,262 B1 | 7/2003 | Honebrink et al. |
| 6,595,955 B2 | 7/2003 | Ferguson et al. |
| 6,595,959 B1 | 7/2003 | Stratienko |
| 6,599,296 B1 | 7/2003 | Gillick et al. |
| 6,607,511 B2 | 8/2003 | Halseth et al. |
| 6,616,630 B1 | 9/2003 | Woehr et al. |
| 6,620,136 B1 | 9/2003 | Pressly, Sr. et al. |
| 6,623,449 B2 | 9/2003 | Paskar |
| 6,623,456 B1 | 9/2003 | Holdaway et al. |
| 6,626,868 B1 | 9/2003 | Prestidge et al. |
| 6,626,869 B1 | 9/2003 | Bint |
| 6,629,959 B2 | 10/2003 | Kuracina et al. |
| 6,632,201 B1 | 10/2003 | Mathias et al. |
| 6,638,252 B2 | 10/2003 | Moulton et al. |
| 6,641,564 B1 | 11/2003 | Kraus |
| 6,645,178 B1 | 11/2003 | Junker et al. |
| 6,652,486 B2 | 11/2003 | Bialecki et al. |
| 6,652,490 B2 | 11/2003 | Howell |
| 6,663,577 B2 | 12/2003 | Jen et al. |
| 6,663,592 B2 | 12/2003 | Rhad et al. |
| 6,666,865 B2 | 12/2003 | Platt |
| 6,679,900 B2 | 1/2004 | Kieturakis et al. |
| 6,689,102 B2 | 2/2004 | Greene |
| 6,692,508 B2 | 2/2004 | Wensel et al. |
| 6,692,509 B2 | 2/2004 | Wensel et al. |
| 6,695,814 B2 | 2/2004 | Greene et al. |
| 6,695,856 B2 | 2/2004 | Kieturakis et al. |
| 6,695,860 B1 | 2/2004 | Ward et al. |
| 6,699,221 B2 | 3/2004 | Vaillancourt |
| 6,702,811 B2 | 3/2004 | Stewart et al. |
| 6,706,018 B2 | 3/2004 | Westlund et al. |

(56) References Cited

U.S. PATENT DOCUMENTS

| | | |
|---|---|---|
| 6,711,444 B2 | 3/2004 | Koblish |
| 6,712,790 B1 | 3/2004 | Prestidge et al. |
| 6,712,797 B1 | 3/2004 | Southern, Jr. |
| 6,716,197 B2 | 4/2004 | Svendsen |
| 6,730,062 B2 | 5/2004 | Hoffman et al. |
| 6,740,063 B2 | 5/2004 | Lynn |
| 6,740,096 B2 | 5/2004 | Teague et al. |
| 6,745,080 B2 | 6/2004 | Koblish |
| 6,749,588 B1 | 6/2004 | Howell et al. |
| 6,764,468 B1 | 7/2004 | East |
| D494,270 S | 8/2004 | Reschke |
| 6,776,788 B1 | 8/2004 | Klint et al. |
| 6,796,962 B2 | 9/2004 | Ferguson et al. |
| 6,824,545 B2 | 11/2004 | Sepetka et al. |
| 6,832,715 B2 | 12/2004 | Eungard et al. |
| 6,835,190 B2 | 12/2004 | Nguyen |
| 6,837,867 B2 | 1/2005 | Kortelling |
| 6,860,871 B2 | 3/2005 | Kuracina et al. |
| 6,872,193 B2 | 3/2005 | Shaw et al. |
| 6,887,220 B2 | 5/2005 | Hogendijk |
| 6,902,546 B2 | 6/2005 | Ferguson |
| 6,905,483 B2 | 6/2005 | Newby et al. |
| 6,913,595 B2 | 7/2005 | Mastorakis |
| 6,916,311 B2 | 7/2005 | Vojtasek |
| 6,921,386 B2 | 7/2005 | Shue et al. |
| 6,921,391 B1 | 7/2005 | Barker et al. |
| 6,929,624 B1 | 8/2005 | Del Castillo |
| 6,939,325 B2 | 9/2005 | Haining |
| 6,942,652 B1 | 9/2005 | Pressly, Sr. et al. |
| 6,953,448 B2 | 10/2005 | Moulton et al. |
| 6,958,054 B2 | 10/2005 | Fitzgerald |
| 6,958,055 B2 | 10/2005 | Donnan et al. |
| 6,960,191 B2 | 11/2005 | Howlett et al. |
| 6,972,002 B2 | 12/2005 | Thorne |
| 6,974,438 B2 | 12/2005 | Shekalim |
| 6,994,693 B2 | 2/2006 | Tal |
| 7,001,396 B2 | 2/2006 | Glazier et al. |
| 7,004,927 B2 | 2/2006 | Ferguson et al. |
| 7,008,404 B2 | 3/2006 | Nakajima |
| 7,018,372 B2 | 3/2006 | Casey et al. |
| 7,018,390 B2 | 3/2006 | Turovskiy et al. |
| 7,025,746 B2 | 4/2006 | Tal |
| 7,029,467 B2 | 4/2006 | Currier et al. |
| 7,033,335 B2 | 4/2006 | Haarala et al. |
| 7,044,935 B2 | 5/2006 | Shue et al. |
| 7,060,055 B2 | 6/2006 | Wilkinson et al. |
| 7,090,656 B1 | 8/2006 | Botich et al. |
| 7,094,243 B2 | 8/2006 | Mulholland et al. |
| 7,097,633 B2 | 8/2006 | Botich et al. |
| 7,125,396 B2 | 10/2006 | Leinsing et al. |
| 7,125,397 B2 | 10/2006 | Woehr et al. |
| 7,141,040 B2 | 11/2006 | Lichtenberg |
| 7,153,276 B2 | 12/2006 | Barker et al. |
| 7,163,520 B2 | 1/2007 | Bernard et al. |
| 7,169,159 B2 | 1/2007 | Green et al. |
| 7,179,244 B2 | 2/2007 | Smith et al. |
| 7,186,239 B2 | 3/2007 | Woehr |
| 7,191,900 B2 | 3/2007 | Opie et al. |
| 7,192,433 B2 | 3/2007 | Osypka et al. |
| 7,204,813 B2 | 4/2007 | Shue et al. |
| 7,214,211 B2 | 5/2007 | Woehr et al. |
| 7,264,613 B2 | 9/2007 | Woehr et al. |
| 7,291,130 B2 | 11/2007 | McGurk |
| 7,303,547 B2 | 12/2007 | Pressly, Sr. et al. |
| 7,303,548 B2 | 12/2007 | Rhad et al. |
| 7,314,462 B2 | 1/2008 | O'Reagan et al. |
| 7,331,966 B2 | 2/2008 | Soma et al. |
| 7,344,516 B2 | 3/2008 | Erskine |
| 7,354,422 B2 | 4/2008 | Riesenberger et al. |
| 7,374,554 B2 | 5/2008 | Menzi et al. |
| 7,381,205 B2 | 6/2008 | Thommen |
| 7,396,346 B2 | 7/2008 | Nakajima |
| 7,413,562 B2 | 8/2008 | Ferguson et al. |
| 7,422,572 B2 | 9/2008 | Popov et al. |
| 7,458,954 B2 | 12/2008 | Ferguson et al. |
| 7,465,294 B1 | 12/2008 | Madimirsky |
| 7,468,057 B2 | 12/2008 | Ponzi |
| 7,470,254 B2 | 12/2008 | Basta et al. |
| 7,491,176 B2 | 2/2009 | Mann |
| 7,494,010 B2 | 2/2009 | Opie et al. |
| 7,500,965 B2 | 3/2009 | Menzi et al. |
| 7,507,222 B2 | 3/2009 | Cindrich et al. |
| 7,513,887 B2 | 4/2009 | Halseth et al. |
| 7,513,888 B2 | 4/2009 | Sircom et al. |
| 7,524,306 B2 | 4/2009 | Botich et al. |
| 7,530,965 B2 | 5/2009 | Villa et al. |
| 7,534,227 B2 | 5/2009 | Kulli |
| 7,534,231 B2 | 5/2009 | Kuracina et al. |
| 7,544,170 B2 | 6/2009 | Williams et al. |
| 7,556,617 B2 | 7/2009 | Voorhees, Jr. et al. |
| 7,566,323 B2 | 7/2009 | Chang |
| D601,243 S | 9/2009 | Bierman et al. |
| 7,597,681 B2 | 10/2009 | Sutton et al. |
| 7,608,057 B2 | 10/2009 | Woehr et al. |
| D604,839 S | 11/2009 | Crawford et al. |
| 7,611,485 B2 | 11/2009 | Ferguson |
| 7,611,487 B2 | 11/2009 | Woehr et al. |
| 7,611,499 B2 | 11/2009 | Woehr et al. |
| 7,618,395 B2 | 11/2009 | Ferguson |
| 7,625,360 B2 | 12/2009 | Woehr et al. |
| 7,628,769 B2 | 12/2009 | Grandt et al. |
| 7,632,243 B2 | 12/2009 | Bialecki et al. |
| 7,645,263 B2 | 1/2010 | Angel et al. |
| 7,654,988 B2 | 2/2010 | Moulton et al. |
| 7,658,725 B2 | 2/2010 | Bialecki et al. |
| D612,043 S | 3/2010 | Young et al. |
| 7,678,080 B2 | 3/2010 | Shue et al. |
| 7,682,358 B2 | 3/2010 | Gullickson et al. |
| 7,691,088 B2 | 4/2010 | Howell |
| 7,691,090 B2 | 4/2010 | Belley et al. |
| 7,691,093 B2 | 4/2010 | Brimhall |
| 7,695,458 B2 | 4/2010 | Belley et al. |
| 7,699,807 B2 | 4/2010 | Faust et al. |
| D615,197 S | 5/2010 | Koh et al. |
| 7,708,721 B2 | 5/2010 | Khaw |
| 7,713,243 B2 | 5/2010 | Hillman |
| 7,717,875 B2 | 5/2010 | Knudson et al. |
| 7,722,567 B2 | 5/2010 | Tal |
| 7,722,569 B2 | 5/2010 | Soderholm et al. |
| D617,893 S | 6/2010 | Bierman et al. |
| 7,731,687 B2 | 6/2010 | Menzi et al. |
| 7,731,691 B2 | 6/2010 | Cote et al. |
| 7,736,332 B2 | 6/2010 | Carlyon et al. |
| 7,736,337 B2 | 6/2010 | Diep et al. |
| 7,736,339 B2 | 6/2010 | Woehr et al. |
| 7,736,342 B2 | 6/2010 | Abriles et al. |
| 7,740,615 B2 | 6/2010 | Shaw et al. |
| 7,744,574 B2 | 6/2010 | Pederson et al. |
| 7,753,877 B2 | 7/2010 | Bialecki et al. |
| 7,753,887 B2 | 7/2010 | Botich et al. |
| 7,762,984 B2 | 7/2010 | Kumoyama et al. |
| 7,762,993 B2 | 7/2010 | Perez |
| 7,766,879 B2 | 8/2010 | Tan et al. |
| 7,776,052 B2 | 8/2010 | Greenberg et al. |
| 7,785,296 B2 | 8/2010 | Muskatello et al. |
| 7,794,424 B2 | 9/2010 | Paskar |
| 7,798,994 B2 | 9/2010 | Brimhall |
| 7,803,142 B2 | 9/2010 | Longson et al. |
| 7,828,773 B2 | 11/2010 | Swisher et al. |
| 7,828,774 B2 | 11/2010 | Harding et al. |
| 7,833,201 B2 | 11/2010 | Carlyon et al. |
| 7,850,644 B2 | 12/2010 | Gonzalez et al. |
| 7,857,770 B2 | 12/2010 | Raulerson et al. |
| D634,843 S | 3/2011 | Kim et al. |
| 7,896,862 B2 | 3/2011 | Long et al. |
| 7,905,857 B2 | 3/2011 | Swisher |
| 7,914,488 B2 | 3/2011 | Dickerson |
| 7,914,492 B2 | 3/2011 | Heuser |
| 7,922,696 B2 | 4/2011 | Tai et al. |
| 7,922,698 B2 | 4/2011 | Riesenberger et al. |
| 7,927,314 B2 | 4/2011 | Kuracina et al. |
| 7,935,080 B2 | 5/2011 | Howell et al. |
| 7,959,613 B2 | 6/2011 | Rhad et al. |
| 7,972,313 B2 | 7/2011 | Woehr et al. |

(56) References Cited

U.S. PATENT DOCUMENTS

| | | |
|---|---|---|
| 7,972,324 B2 | 7/2011 | Quint |
| D643,531 S | 8/2011 | van der Weiden |
| 8,029,470 B2 | 10/2011 | Whiting et al. |
| 8,029,472 B2 | 10/2011 | Leinsing et al. |
| 8,048,031 B2 | 11/2011 | Shaw et al. |
| 8,048,039 B2 | 11/2011 | Carlyon et al. |
| 8,057,404 B2 | 11/2011 | Fujiwara et al. |
| 8,062,261 B2 | 11/2011 | Adams |
| 8,075,529 B2 | 12/2011 | Nakajima et al. |
| 8,079,979 B2 | 12/2011 | Moorehead |
| D653,329 S | 1/2012 | Lee-Sepsick |
| 8,100,858 B2 | 1/2012 | Woehr et al. |
| 8,105,286 B2 | 1/2012 | Anderson et al. |
| 8,105,315 B2 | 1/2012 | Johnson et al. |
| 8,123,727 B2 | 2/2012 | Luther et al. |
| 8,152,758 B2 | 4/2012 | Chan et al. |
| 8,162,881 B2 | 4/2012 | Lilley, Jr. et al. |
| 8,167,851 B2 | 5/2012 | Sen |
| 8,177,753 B2 | 5/2012 | Vitullo et al. |
| RE43,473 E | 6/2012 | Newby et al. |
| 8,192,402 B2 | 6/2012 | Anderson et al. |
| 8,202,251 B2 | 6/2012 | Bierman et al. |
| 8,202,253 B1 | 6/2012 | Wexler |
| 8,206,343 B2 | 6/2012 | Racz |
| 8,211,070 B2 | 7/2012 | Woehr et al. |
| 8,221,387 B2 | 7/2012 | Shelso et al. |
| 8,226,612 B2 | 7/2012 | Nakajima |
| 8,235,945 B2 | 8/2012 | Baid |
| 8,251,923 B2 | 8/2012 | Carrez et al. |
| 8,251,950 B2 | 8/2012 | Albert et al. |
| D667,111 S | 9/2012 | Robinson |
| 8,257,322 B2 | 9/2012 | Koehler et al. |
| 8,273,054 B2 | 9/2012 | St. Germain et al. |
| 8,286,657 B2 | 10/2012 | Belley et al. |
| 8,298,186 B2 | 10/2012 | Popov |
| 8,303,543 B2 | 11/2012 | Abulhaj |
| 8,308,685 B2 | 11/2012 | Botich et al. |
| 8,308,691 B2 | 11/2012 | Woehr et al. |
| D672,456 S | 12/2012 | Lee-Sepsick |
| 8,323,249 B2 | 12/2012 | White et al. |
| 8,328,762 B2 | 12/2012 | Woehr et al. |
| 8,328,837 B2 | 12/2012 | Binmoeller |
| 8,333,735 B2 | 12/2012 | Woehr et al. |
| 8,337,424 B2 | 12/2012 | Palmer et al. |
| 8,337,463 B2 | 12/2012 | Woehr et al. |
| 8,337,471 B2 | 12/2012 | Baid |
| D675,318 S | 1/2013 | Luk et al. |
| 8,361,020 B2 | 1/2013 | Stout |
| 8,361,038 B2 | 1/2013 | McKinnon et al. |
| 8,376,994 B2 | 2/2013 | Woehr et al. |
| 8,377,006 B2 | 2/2013 | Tal et al. |
| 8,382,721 B2 | 2/2013 | Woehr et al. |
| 8,388,583 B2 | 3/2013 | Stout et al. |
| 8,403,886 B2 | 3/2013 | Bialecki et al. |
| 8,412,300 B2 | 4/2013 | Sonderegger |
| 8,414,539 B1 | 4/2013 | Kuracina et al. |
| 8,419,688 B2 | 4/2013 | Woehr et al. |
| 8,444,605 B2 | 5/2013 | Kuracina et al. |
| 8,454,536 B2 | 6/2013 | Raulerson et al. |
| 8,460,247 B2 | 6/2013 | Woehr et al. |
| 8,469,928 B2 | 6/2013 | Stout et al. |
| 8,496,628 B2 | 7/2013 | Erskine |
| D687,548 S | 8/2013 | Hayashi |
| 8,506,533 B2 | 8/2013 | Carlyon et al. |
| 8,509,340 B2 | 8/2013 | Michelitsch |
| 8,517,959 B2 | 8/2013 | Kurosawa et al. |
| 8,529,515 B2 | 9/2013 | Woehr et al. |
| 8,535,271 B2 | 9/2013 | Fuchs et al. |
| 8,540,728 B2 | 9/2013 | Woehr et al. |
| 8,545,454 B2 | 10/2013 | Kuracina et al. |
| 8,568,372 B2 | 10/2013 | Woehr et al. |
| 8,574,203 B2 | 11/2013 | Stout et al. |
| 8,579,881 B2 | 11/2013 | Agro et al. |
| 8,585,651 B2 | 11/2013 | Asai |
| 8,585,660 B2 | 11/2013 | Murphy |
| 8,591,467 B2 | 11/2013 | Walker et al. |
| 8,591,468 B2 | 11/2013 | Woehr et al. |
| 8,597,249 B2 | 12/2013 | Woehr et al. |
| 8,622,931 B2 | 1/2014 | Teague et al. |
| 8,622,958 B2 | 1/2014 | Jones et al. |
| 8,622,972 B2 | 1/2014 | Nystrom et al. |
| D700,318 S | 2/2014 | Amoah et al. |
| 8,647,301 B2 | 2/2014 | Bialecki et al. |
| 8,647,313 B2 | 2/2014 | Woehr et al. |
| 8,647,324 B2 | 2/2014 | DeLegge et al. |
| 8,652,104 B2 | 2/2014 | Goral et al. |
| 8,657,790 B2 | 2/2014 | Tal et al. |
| 8,672,888 B2 | 3/2014 | Tal |
| 8,679,063 B2 | 3/2014 | Stout et al. |
| 8,690,833 B2 | 4/2014 | Belson |
| 8,715,242 B2 | 5/2014 | Helm, Jr. |
| 8,721,546 B2 | 5/2014 | Belson |
| 8,728,030 B2 | 5/2014 | Woehr |
| 8,728,035 B2 | 5/2014 | Warring et al. |
| 8,740,859 B2 | 6/2014 | McKinnon et al. |
| 8,740,964 B2 | 6/2014 | Hartley |
| 8,747,387 B2 | 6/2014 | Belley et al. |
| 8,753,317 B2 | 6/2014 | Osborne et al. |
| 8,764,711 B2 | 7/2014 | Kuracina et al. |
| D710,495 S | 8/2014 | Wu et al. |
| 8,814,833 B2 | 8/2014 | Farrell et al. |
| D713,957 S | 9/2014 | Woehr et al. |
| D714,436 S | 9/2014 | Lee-Sepsick |
| 8,827,965 B2 | 9/2014 | Woehr et al. |
| 8,845,584 B2 | 9/2014 | Ferguson et al. |
| D715,931 S | 10/2014 | Watanabe et al. |
| 8,864,714 B2 | 10/2014 | Harding et al. |
| 8,900,192 B2 | 12/2014 | Anderson et al. |
| 8,932,257 B2 | 1/2015 | Woehr |
| 8,932,258 B2 | 1/2015 | Blanchard et al. |
| 8,932,259 B2 | 1/2015 | Stout et al. |
| 8,945,011 B2 | 2/2015 | Sheldon et al. |
| 8,951,230 B2 | 2/2015 | Tanabe et al. |
| 8,956,327 B2 | 2/2015 | Bierman et al. |
| 8,974,426 B2 | 3/2015 | Corcoran et al. |
| 8,979,802 B2 | 3/2015 | Woehr |
| 8,986,227 B2 | 3/2015 | Belson |
| D726,908 S | 4/2015 | Yu et al. |
| 8,998,852 B2 | 4/2015 | Blanchard et al. |
| 9,005,169 B2 | 4/2015 | Gravesen et al. |
| 9,011,351 B2 | 4/2015 | Hoshinouchi |
| 9,011,381 B2 | 4/2015 | Yamada et al. |
| D728,781 S | 5/2015 | Pierson et al. |
| 9,022,979 B2 | 5/2015 | Woehr |
| 9,033,927 B2 | 5/2015 | Maan et al. |
| D733,289 S | 6/2015 | Blanchard et al. |
| 9,044,583 B2 | 6/2015 | Vaillancourt |
| D735,321 S | 7/2015 | Blanchard |
| 9,089,671 B2 | 7/2015 | Stout et al. |
| 9,089,674 B2 | 7/2015 | Ginn et al. |
| 9,095,683 B2 | 8/2015 | Hall et al. |
| 9,101,746 B2 | 8/2015 | Stout et al. |
| 9,108,021 B2 | 8/2015 | Hyer et al. |
| 9,114,231 B2 | 8/2015 | Woehr et al. |
| 9,114,241 B2 | 8/2015 | Stout et al. |
| 9,126,012 B2 | 9/2015 | McKinnon et al. |
| 9,138,252 B2 | 9/2015 | Bierman et al. |
| 9,138,545 B2 | 9/2015 | Shaw et al. |
| 9,138,559 B2 | 9/2015 | Odland et al. |
| RE45,776 E | 10/2015 | Root et al. |
| D740,410 S | 10/2015 | Korkuch et al. |
| 9,149,625 B2 | 10/2015 | Woehr et al. |
| 9,149,626 B2 | 10/2015 | Woehr et al. |
| 9,155,863 B2 | 10/2015 | Isaacson et al. |
| 9,162,036 B2 | 10/2015 | Caples et al. |
| 9,162,037 B2 | 10/2015 | Belson et al. |
| 9,180,275 B2 | 11/2015 | Helm |
| D746,445 S | 12/2015 | Lazarus |
| 9,205,231 B2 | 12/2015 | Call et al. |
| 9,216,109 B2 | 12/2015 | Badawi et al. |
| 9,220,531 B2 | 12/2015 | Datta et al. |
| 9,220,871 B2 | 12/2015 | Thorne et al. |
| 9,220,882 B2 | 12/2015 | Belley et al. |
| D748,254 S | 1/2016 | Freigang et al. |

(56) References Cited

U.S. PATENT DOCUMENTS

| | | |
|---|---|---|
| 9,227,038 B2 | 1/2016 | Woehr |
| 9,242,071 B2 | 1/2016 | Morgan et al. |
| 9,242,072 B2 | 1/2016 | Morgan et al. |
| RE45,896 E | 2/2016 | Stout et al. |
| D748,774 S | 2/2016 | Caron |
| D748,777 S | 2/2016 | Uenishi et al. |
| D749,214 S | 2/2016 | Uenishi et al. |
| D749,727 S | 2/2016 | Wapler et al. |
| D751,194 S | 3/2016 | Yu et al. |
| D752,737 S | 3/2016 | Ohashi |
| 9,289,237 B2 | 3/2016 | Woehr et al. |
| 9,308,352 B2 | 4/2016 | Teoh et al. |
| 9,308,354 B2 | 4/2016 | Farrell et al. |
| 9,320,870 B2 | 4/2016 | Woehr |
| D755,368 S | 5/2016 | Efinger et al. |
| 9,352,119 B2 | 5/2016 | Burkholz et al. |
| 9,352,127 B2 | 5/2016 | Yeh et al. |
| 9,352,129 B2 | 5/2016 | Nardeo et al. |
| 9,358,364 B2 | 6/2016 | Isaacson et al. |
| 9,370,641 B2 | 6/2016 | Woehr et al. |
| 9,381,324 B2 | 7/2016 | Fuchs et al. |
| 9,399,116 B2 | 7/2016 | Goral et al. |
| 9,408,569 B2 | 8/2016 | Andreae et al. |
| 9,421,345 B2 | 8/2016 | Woehr et al. |
| 9,427,549 B2 | 8/2016 | Woehr et al. |
| D775,330 S | 12/2016 | Blennow et al. |
| 9,522,254 B2 | 12/2016 | Belson |
| D776,259 S | 1/2017 | Eldredge |
| 9,545,495 B2 | 1/2017 | Goral et al. |
| 9,554,817 B2 | 1/2017 | Goldfarb et al. |
| D779,059 S | 2/2017 | Nino et al. |
| D779,661 S | 2/2017 | McKnight et al. |
| 9,579,486 B2 | 2/2017 | Burkholz et al. |
| 9,586,027 B2 | 3/2017 | Tisci et al. |
| 9,592,367 B2 | 3/2017 | Harding et al. |
| 9,616,201 B2 | 4/2017 | Belson |
| 9,623,210 B2 | 4/2017 | Woehr |
| 9,675,784 B2 | 6/2017 | Belson |
| 9,687,633 B2 | 6/2017 | Teoh |
| D791,311 S | 7/2017 | Yantz |
| 9,707,378 B2 | 7/2017 | Leinsing et al. |
| 9,717,523 B2 | 8/2017 | Feng et al. |
| 9,717,887 B2 | 8/2017 | Tan |
| 9,737,252 B2 | 8/2017 | Teoh et al. |
| 9,750,532 B2 | 9/2017 | Toomey et al. |
| 9,750,928 B2 | 9/2017 | Burkholz et al. |
| 9,757,540 B2 | 9/2017 | Belson |
| 9,764,085 B2 | 9/2017 | Teoh |
| 9,764,117 B2 | 9/2017 | Bierman et al. |
| 9,775,972 B2 | 10/2017 | Christensen et al. |
| 9,782,568 B2 | 10/2017 | Belson |
| 9,789,279 B2 | 10/2017 | Burkholz et al. |
| 9,795,766 B2 | 10/2017 | Teoh |
| 9,844,646 B2 | 12/2017 | Knutsson |
| 9,861,792 B2 | 1/2018 | Hall et al. |
| 9,872,971 B2 | 1/2018 | Blanchard |
| D810,282 S | 2/2018 | Ratjen |
| D815,737 S | 4/2018 | Bergstrom et al. |
| 9,950,139 B2 | 4/2018 | Blanchard et al. |
| 9,962,525 B2 | 5/2018 | Woehr |
| 10,004,878 B2 | 6/2018 | Ishida |
| 10,086,171 B2 | 10/2018 | Belson |
| 10,232,146 B2 | 3/2019 | Braithwaite et al. |
| 10,328,239 B2 | 6/2019 | Belson |
| 10,357,635 B2 | 7/2019 | Korkuch et al. |
| 10,384,039 B2 | 8/2019 | Ribelin et al. |
| 10,426,931 B2 | 10/2019 | Blanchard et al. |
| D870,271 S | 12/2019 | Kheradpir et al. |
| D870,883 S | 12/2019 | Harding et al. |
| 10,493,262 B2 | 12/2019 | Tran et al. |
| 10,525,236 B2 | 1/2020 | Belson |
| 10,688,280 B2 | 6/2020 | Blanchard et al. |
| 10,688,281 B2 | 6/2020 | Blanchard et al. |
| 10,722,685 B2 | 7/2020 | Blanchard et al. |
| 10,806,906 B2 | 10/2020 | Warring et al. |
| 11,389,626 B2 | 7/2022 | Tran et al. |
| 11,400,260 B2 | 8/2022 | Huang et al. |
| 2001/0014786 A1 | 8/2001 | Greene et al. |
| 2001/0020153 A1 | 9/2001 | Howell |
| 2002/0052576 A1 | 5/2002 | Massengale |
| 2002/0077595 A1 | 6/2002 | Hundertmark et al. |
| 2002/0103446 A1 | 8/2002 | McFann et al. |
| 2002/0107526 A1 | 8/2002 | Greenberg et al. |
| 2002/0128604 A1 | 9/2002 | Nakajima |
| 2002/0165497 A1 | 11/2002 | Greene |
| 2002/0177812 A1 | 11/2002 | Moulton et al. |
| 2003/0032922 A1 | 2/2003 | Moorehead |
| 2003/0032936 A1 | 2/2003 | Lederman |
| 2003/0060760 A1 | 3/2003 | Botich et al. |
| 2003/0073956 A1 | 4/2003 | Hoffman et al. |
| 2003/0120214 A1 | 6/2003 | Howell |
| 2003/0153874 A1 | 8/2003 | Tal |
| 2003/0187396 A1 | 10/2003 | Ponzi |
| 2003/0204186 A1 | 10/2003 | Geistert |
| 2004/0019329 A1 | 1/2004 | Erskine |
| 2004/0034383 A1 | 2/2004 | Belson |
| 2004/0044302 A1 | 3/2004 | Bernard et al. |
| 2004/0044313 A1 | 3/2004 | Nakajima |
| 2004/0092879 A1 | 5/2004 | Kraus et al. |
| 2004/0106903 A1 | 6/2004 | Shue et al. |
| 2004/0111059 A1 | 6/2004 | Howlett et al. |
| 2004/0122373 A1 | 6/2004 | Botich et al. |
| 2004/0176758 A1 | 9/2004 | Yassinzadeh |
| 2004/0193118 A1 | 9/2004 | Bergeron |
| 2004/0215146 A1 | 10/2004 | Lampropoulos et al. |
| 2004/0236288 A1 | 11/2004 | Howell et al. |
| 2004/0243061 A1 | 12/2004 | McGurk |
| 2004/0267204 A1 | 12/2004 | Brustowicz |
| 2005/0004524 A1 | 1/2005 | Newby et al. |
| 2005/0004532 A1 | 1/2005 | Woehr et al. |
| 2005/0010095 A1 | 1/2005 | Stewart et al. |
| 2005/0020940 A1 | 1/2005 | Opie et al. |
| 2005/0021002 A1 | 1/2005 | Deckman et al. |
| 2005/0027256 A1 | 2/2005 | Barker et al. |
| 2005/0033137 A1 | 2/2005 | Oral et al. |
| 2005/0040061 A1 | 2/2005 | Opie et al. |
| 2005/0075606 A1 | 4/2005 | Botich et al. |
| 2005/0107769 A1 | 5/2005 | Thommen |
| 2005/0119619 A1 | 6/2005 | Haining |
| 2005/0131350 A1 | 6/2005 | Shaw et al. |
| 2005/0165355 A1 | 7/2005 | Fitzgerald |
| 2005/0197623 A1 | 9/2005 | Leeflang et al. |
| 2005/0245847 A1 | 11/2005 | Schaeffer |
| 2005/0256505 A1 | 11/2005 | Long et al. |
| 2005/0273057 A1 | 12/2005 | Popov |
| 2006/0025721 A1 | 2/2006 | Duffy et al. |
| 2006/0036219 A1 | 2/2006 | Alvin |
| 2006/0079787 A1 | 4/2006 | Whiting et al. |
| 2006/0084964 A1 | 4/2006 | Knudson et al. |
| 2006/0155245 A1 | 7/2006 | Woehr |
| 2006/0161115 A1 | 7/2006 | Fangrow |
| 2006/0167405 A1 | 7/2006 | King et al. |
| 2006/0200080 A1 | 9/2006 | Abulhaj |
| 2006/0229563 A1 | 10/2006 | O'Reagan et al. |
| 2006/0264834 A1 | 11/2006 | Vaillancourt |
| 2007/0043422 A1 | 2/2007 | Shmulewitz et al. |
| 2007/0060999 A1 | 3/2007 | Randall et al. |
| 2007/0083162 A1 | 4/2007 | O'Reagan et al. |
| 2007/0083188 A1 | 4/2007 | Grandt et al. |
| 2007/0100284 A1 | 5/2007 | Leinsing et al. |
| 2007/0123803 A1 | 5/2007 | Fujiwara et al. |
| 2007/0142779 A1 | 6/2007 | Duane et al. |
| 2007/0179446 A1 | 8/2007 | Carrez et al. |
| 2007/0191777 A1 | 8/2007 | King |
| 2007/0193903 A1 | 8/2007 | Opie et al. |
| 2007/0225647 A1 | 9/2007 | Luther et al. |
| 2007/0233007 A1 | 10/2007 | Adams |
| 2007/0244438 A1 | 10/2007 | Perez |
| 2007/0255221 A1 | 11/2007 | Nakajima |
| 2007/0276288 A1 | 11/2007 | Khaw |
| 2008/0039796 A1 | 2/2008 | Nakajima |
| 2008/0065011 A1 | 3/2008 | Marchand et al. |
| 2008/0082082 A1 | 4/2008 | Carlyon et al. |
| 2008/0097330 A1 | 4/2008 | King et al. |

(56) References Cited

U.S. PATENT DOCUMENTS

| | | |
|---|---|---|
| 2008/0108911 A1 | 5/2008 | Palmer et al. |
| 2008/0108944 A1 | 5/2008 | Woehr et al. |
| 2008/0108974 A1 | 5/2008 | Yee Roth |
| 2008/0125709 A1 | 5/2008 | Chang et al. |
| 2008/0131300 A1 | 6/2008 | Junod et al. |
| 2008/0132846 A1 | 6/2008 | Shue et al. |
| 2008/0147010 A1 | 6/2008 | Nakajima et al. |
| 2008/0243165 A1 | 10/2008 | Mauch et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0300574 A1 | 12/2008 | Belson et al. |
| 2009/0018567 A1 | 1/2009 | Escudero et al. |
| 2009/0030380 A1 | 1/2009 | Binmoeller |
| 2009/0036836 A1 | 2/2009 | Nystrom et al. |
| 2009/0048566 A1 | 2/2009 | Ferguson et al. |
| 2009/0131872 A1 | 5/2009 | Popov |
| 2009/0157006 A1 | 6/2009 | Nardeo et al. |
| 2009/0221961 A1 | 9/2009 | Tal et al. |
| 2009/0292243 A1 | 11/2009 | Harding et al. |
| 2009/0299291 A1 | 12/2009 | Baid |
| 2010/0010441 A1 | 1/2010 | Belson |
| 2010/0010447 A1 | 1/2010 | Luther et al. |
| 2010/0016838 A1 | 1/2010 | Butts et al. |
| 2010/0036331 A1 | 2/2010 | Sen |
| 2010/0056910 A1 | 3/2010 | Yanuma |
| 2010/0057183 A1 | 3/2010 | Mangiardi et al. |
| 2010/0087787 A1 | 4/2010 | Woehr et al. |
| 2010/0094116 A1 | 4/2010 | Silverstein |
| 2010/0094310 A1 | 4/2010 | Warring et al. |
| 2010/0137815 A1 | 6/2010 | Kuracina et al. |
| 2010/0168674 A1 | 7/2010 | Shaw et al. |
| 2010/0204654 A1 | 8/2010 | Mulholland et al. |
| 2010/0204660 A1 | 8/2010 | McKinnon et al. |
| 2010/0204675 A1 | 8/2010 | Woehr et al. |
| 2010/0210934 A1 | 8/2010 | Belson |
| 2010/0238705 A1 | 9/2010 | Kim et al. |
| 2010/0246707 A1 | 9/2010 | Michelitsch |
| 2010/0331732 A1 | 12/2010 | Raulerson et al. |
| 2011/0004162 A1 | 1/2011 | Tai |
| 2011/0009827 A1 | 1/2011 | Bierman et al. |
| 2011/0015573 A1 | 1/2011 | Maan et al. |
| 2011/0021994 A1 | 1/2011 | Anderson et al. |
| 2011/0125097 A1 | 5/2011 | Shaw et al. |
| 2011/0137252 A1 | 6/2011 | Oster et al. |
| 2011/0196315 A1 | 8/2011 | Chappel |
| 2011/0207157 A1 | 8/2011 | Gautier et al. |
| 2011/0218496 A1 | 9/2011 | Bierman |
| 2011/0251559 A1 | 10/2011 | Tal et al. |
| 2011/0276002 A1 | 11/2011 | Bierman |
| 2011/0282285 A1 | 11/2011 | Blanchard et al. |
| 2011/0288482 A1 | 11/2011 | Farrell et al. |
| 2011/0306933 A1 | 12/2011 | Djordjevic et al. |
| 2011/0319838 A1 | 12/2011 | Goral et al. |
| 2012/0053523 A1 | 3/2012 | Harding |
| 2012/0071857 A1 | 3/2012 | Goldfarb et al. |
| 2012/0078231 A1 | 3/2012 | Hoshinouchi |
| 2012/0101440 A1 | 4/2012 | Kamen et al. |
| 2012/0123332 A1 | 5/2012 | Erskine |
| 2012/0123354 A1 | 5/2012 | Woehr |
| 2012/0157854 A1 | 6/2012 | Kurrus et al. |
| 2012/0179104 A1 | 7/2012 | Woehr et al. |
| 2012/0184896 A1 | 7/2012 | DeLegge et al. |
| 2012/0197200 A1 | 8/2012 | Belson |
| 2012/0220942 A1 | 8/2012 | Hall et al. |
| 2012/0220956 A1 | 8/2012 | Kuracina et al. |
| 2012/0259293 A1 | 10/2012 | Bialecki et al. |
| 2012/0271232 A1 | 10/2012 | Katsurada et al. |
| 2012/0296282 A1 | 11/2012 | Koehler et al. |
| 2012/0316500 A1 | 12/2012 | Bierman et al. |
| 2012/0323181 A1 | 12/2012 | Shaw et al. |
| 2013/0030391 A1 | 1/2013 | Baid |
| 2013/0158506 A1 | 6/2013 | Harris et al. |
| 2013/0184645 A1 | 7/2013 | Baid |
| 2013/0204206 A1 | 8/2013 | Morgan et al. |
| 2013/0204226 A1 | 8/2013 | Keyser |
| 2013/0218082 A1 | 8/2013 | Hyer et al. |
| 2013/0304030 A1 | 11/2013 | Gray et al. |
| 2013/0310764 A1 | 11/2013 | Burkholz et al. |
| 2013/0324930 A1 | 12/2013 | Fuchs et al. |
| 2014/0012203 A1 | 1/2014 | Woehr et al. |
| 2014/0031752 A1 | 1/2014 | Blanchard et al. |
| 2014/0039461 A1 | 2/2014 | Anderson et al. |
| 2014/0058329 A1 | 2/2014 | Walker et al. |
| 2014/0058336 A1 | 2/2014 | Burkholz et al. |
| 2014/0058357 A1 | 2/2014 | Keyser et al. |
| 2014/0073928 A1 | 3/2014 | Yamashita et al. |
| 2014/0074034 A1 | 3/2014 | Tanabe et al. |
| 2014/0088509 A1 | 3/2014 | Sonderegger et al. |
| 2014/0094774 A1 | 4/2014 | Blanchard |
| 2014/0094836 A1 | 4/2014 | Feng et al. |
| 2014/0114239 A1 | 4/2014 | Dib et al. |
| 2014/0128775 A1 | 5/2014 | Andreae et al. |
| 2014/0135702 A1 | 5/2014 | Woehr et al. |
| 2014/0135703 A1 | 5/2014 | Yeh et al. |
| 2014/0143999 A1 | 5/2014 | Goral et al. |
| 2014/0180250 A1 | 6/2014 | Belson |
| 2014/0188003 A1 | 7/2014 | Belson |
| 2014/0194853 A1 | 7/2014 | Morgan et al. |
| 2014/0214005 A1 | 7/2014 | Belson |
| 2014/0221977 A1 | 8/2014 | Belson |
| 2014/0236099 A1 | 8/2014 | Nakagami et al. |
| 2014/0243734 A1 | 8/2014 | Eubanks et al. |
| 2014/0249488 A1 | 9/2014 | Woehr |
| 2014/0257359 A1 | 9/2014 | Fegels et al. |
| 2014/0276224 A1 | 9/2014 | Ranganathan et al. |
| 2014/0276432 A1 | 9/2014 | Bierman et al. |
| 2014/0276434 A1 | 9/2014 | Woehr et al. |
| 2014/0303561 A1 | 10/2014 | Li |
| 2014/0323988 A1 | 10/2014 | Magnani et al. |
| 2014/0336582 A1 | 11/2014 | Tisci et al. |
| 2014/0357983 A1 | 12/2014 | Toomey et al. |
| 2014/0358123 A1 | 12/2014 | Ueda et al. |
| 2014/0364809 A1 | 12/2014 | Isaacson et al. |
| 2014/0371715 A1 | 12/2014 | Farrell et al. |
| 2014/0371720 A1 | 12/2014 | Urmey |
| 2014/0378867 A1 | 12/2014 | Belson |
| 2015/0025467 A1 | 1/2015 | Woehr |
| 2015/0038909 A1 | 2/2015 | Christensen et al. |
| 2015/0038910 A1 | 2/2015 | Harding et al. |
| 2015/0038943 A1 | 2/2015 | Warring et al. |
| 2015/0051584 A1 | 2/2015 | Korkuch et al. |
| 2015/0080801 A1 | 3/2015 | Tanabe et al. |
| 2015/0080810 A1 | 3/2015 | Henderson et al. |
| 2015/0088095 A1 | 3/2015 | Luther et al. |
| 2015/0094659 A1 | 4/2015 | Schraga |
| 2015/0119806 A1 | 4/2015 | Blanchard et al. |
| 2015/0119852 A1 | 4/2015 | Wexler |
| 2015/0126932 A1 | 5/2015 | Knutsson |
| 2015/0151086 A1 | 6/2015 | Teoh |
| 2015/0151088 A1 | 6/2015 | Lim et al. |
| 2015/0190168 A1 | 7/2015 | Bierman et al. |
| 2015/0190570 A1 | 7/2015 | Teoh |
| 2015/0190617 A1 | 7/2015 | Anderson et al. |
| 2015/0202414 A1 | 7/2015 | Hwang |
| 2015/0202421 A1 | 7/2015 | Ma et al. |
| 2015/0224267 A1 | 8/2015 | Farrell et al. |
| 2015/0231364 A1 | 8/2015 | Blanchard et al. |
| 2015/0238705 A1 | 8/2015 | Gravesen et al. |
| 2015/0290431 A1 | 10/2015 | Hall et al. |
| 2015/0306347 A1 | 10/2015 | Yagi |
| 2015/0306356 A1 | 10/2015 | Gill |
| 2015/0328434 A1 | 11/2015 | Gaur |
| 2015/0328438 A1 | 11/2015 | Baid |
| 2015/0335858 A1 | 11/2015 | Woehr et al. |
| 2015/0359473 A1 | 12/2015 | Garrett et al. |
| 2016/0008580 A1 | 1/2016 | Woehr et al. |
| 2016/0015943 A1 | 1/2016 | Belson et al. |
| 2016/0015945 A1 | 1/2016 | Warring et al. |
| 2016/0022312 A1 | 1/2016 | Tang et al. |
| 2016/0022963 A1 | 1/2016 | Belson |
| 2016/0030716 A1 | 2/2016 | Mallin et al. |
| 2016/0045715 A1 | 2/2016 | Galgano et al. |
| 2016/0089513 A1 | 3/2016 | Ishida |

(56) References Cited

U.S. PATENT DOCUMENTS

| | | |
|---|---|---|
| 2016/0106959 A1 | 4/2016 | Woehr |
| 2016/0114136 A1 | 4/2016 | Woehr |
| 2016/0114137 A1 | 4/2016 | Woehr et al. |
| 2016/0158503 A1 | 6/2016 | Woehr |
| 2016/0158526 A1 | 6/2016 | Woehr |
| 2016/0175563 A1 | 6/2016 | Woehr et al. |
| 2016/0184557 A1 | 6/2016 | Call et al. |
| 2016/0199575 A1 | 7/2016 | Belley et al. |
| 2016/0206852 A1 | 7/2016 | Morgan et al. |
| 2016/0206858 A1 | 7/2016 | Ishida |
| 2016/0220161 A1 | 8/2016 | Goral et al. |
| 2016/0220786 A1 | 8/2016 | Mitchell et al. |
| 2016/0256667 A1 | 9/2016 | Ribelin et al. |
| 2016/0296729 A1 | 10/2016 | Fuchs et al. |
| 2016/0310704 A1 | 10/2016 | Ng et al. |
| 2016/0331937 A1 | 11/2016 | Teoh |
| 2016/0331938 A1 | 11/2016 | Blanchard et al. |
| 2016/0354580 A1 | 12/2016 | Teoh et al. |
| 2016/0361490 A1 | 12/2016 | Phang et al. |
| 2016/0361519 A1 | 12/2016 | Teoh et al. |
| 2017/0000982 A1 | 1/2017 | Ishida |
| 2017/0035992 A1 | 2/2017 | Harding et al. |
| 2017/0043132 A1 | 2/2017 | Ishida |
| 2017/0087338 A1 | 3/2017 | Belson |
| 2017/0136217 A1 | 5/2017 | Riesenberger et al. |
| 2017/0203050 A1 | 7/2017 | Bauer et al. |
| 2017/0209668 A1 | 7/2017 | Belson |
| 2017/0246429 A1 | 8/2017 | Tan et al. |
| 2017/0259036 A1 | 9/2017 | Belson |
| 2017/0361071 A1 | 12/2017 | Belson |
| 2018/0028780 A1 | 2/2018 | Blanchard et al. |
| 2018/0071509 A1 | 3/2018 | Tran et al. |
| 2018/0099123 A1 | 4/2018 | Woehr |
| 2018/0126125 A1 | 5/2018 | Hall et al. |
| 2018/0133437 A1 | 5/2018 | Blanchard |
| 2018/0229003 A1 | 8/2018 | Blanchard et al. |
| 2018/0229004 A1 | 8/2018 | Blanchard et al. |
| 2019/0022358 A1 | 1/2019 | Belson |
| 2019/0192829 A1 | 6/2019 | Belson et al. |
| 2019/0201667 A1 | 7/2019 | Braithwaite et al. |
| 2019/0240459 A1 | 8/2019 | Belson |
| 2019/0275303 A1 | 9/2019 | Tran et al. |
| 2019/0307986 A1 | 10/2019 | Belson |
| 2019/0351193 A1 | 11/2019 | Hall |
| 2019/0351196 A1 | 11/2019 | Ribelin et al. |
| 2020/0001051 A1 | 1/2020 | Huang et al. |
| 2020/0094037 A1 | 3/2020 | Tran et al. |
| 2020/0261696 A1 | 8/2020 | Blanchard |
| 2020/0261703 A1 | 8/2020 | Belson et al. |
| 2020/0316347 A1 | 10/2020 | Belson |
| 2021/0308428 A1 | 10/2021 | Blanchard et al. |
| 2021/0402155 A1 | 12/2021 | Hall et al. |

FOREIGN PATENT DOCUMENTS

| | | |
|---|---|---|
| CN | 1319023 A | 10/2001 |
| CN | 1523970 A | 8/2004 |
| CN | 1871043 A | 11/2006 |
| CN | 101242868 A | 8/2008 |
| CN | 101293122 A | 10/2008 |
| CN | 101417159 A | 4/2009 |
| CN | 101784300 A | 7/2010 |
| CN | 102099075 A | 6/2011 |
| CN | 102939129 A | 2/2013 |
| CN | 104689456 A | 6/2015 |
| CN | 105073174 A | 11/2015 |
| CN | 105188826 A | 12/2015 |
| CN | 105705191 A | 6/2016 |
| DE | 20210394 U1 | 9/2002 |
| EP | 0314470 A2 | 5/1989 |
| EP | 47764 A1 | 3/1991 |
| EP | 45857 A1 | 3/1992 |
| EP | 515710 A1 | 12/1992 |
| EP | 567321 A2 | 10/1993 |
| EP | 652020 A2 | 5/1995 |
| EP | 0730880 A1 | 9/1996 |
| EP | 747075 A2 | 12/1996 |
| EP | 750916 A2 | 1/1997 |
| EP | 778043 A1 | 6/1997 |
| EP | 800790 A2 | 10/1997 |
| EP | 832663 A2 | 4/1998 |
| EP | 910988 A1 | 4/1999 |
| EP | 1075850 A2 | 2/2001 |
| EP | 1378263 A2 | 1/2004 |
| EP | 1457229 A1 | 9/2004 |
| EP | 1611916 A1 | 1/2006 |
| EP | 2272432 A1 | 1/2011 |
| GB | 2529270 A | 2/2016 |
| JP | 2003-159334 A | 6/2003 |
| JP | 2004-130074 A | 4/2004 |
| JP | 2004-223252 A | 8/2004 |
| JP | 2005-137888 A | 6/2005 |
| JP | 2009-500129 A | 1/2009 |
| JP | 2010-088521 A | 4/2010 |
| JP | 2013-529111 A | 7/2013 |
| JP | 2018-118079 A | 8/2018 |
| JP | 6692869 B2 | 5/2020 |
| WO | 83/01575 A1 | 5/1983 |
| WO | 1992013584 A1 | 8/1992 |
| WO | 92/22344 A1 | 12/1992 |
| WO | 1994006681 A2 | 3/1994 |
| WO | 95/19193 A1 | 7/1995 |
| WO | 95/23003 A1 | 8/1995 |
| WO | 96/32981 A1 | 10/1996 |
| WO | 1996040359 A1 | 12/1996 |
| WO | 97/05912 A2 | 2/1997 |
| WO | 97/21458 A1 | 6/1997 |
| WO | 1997045151 A1 | 12/1997 |
| WO | 98/24494 A1 | 6/1998 |
| WO | 1998030268 A1 | 7/1998 |
| WO | 1998053875 A1 | 12/1998 |
| WO | 1999008742 A1 | 2/1999 |
| WO | 1999026682 A1 | 6/1999 |
| WO | 00/06226 A1 | 2/2000 |
| WO | 00/12160 A1 | 3/2000 |
| WO | 2000012167 A1 | 3/2000 |
| WO | 00/47256 A1 | 8/2000 |
| WO | 00/67829 A1 | 11/2000 |
| WO | 2001007103 A1 | 2/2001 |
| WO | 01/26725 A1 | 4/2001 |
| WO | 02/41932 A2 | 5/2002 |
| WO | 02/066093 A2 | 8/2002 |
| WO | 03/11381 A1 | 2/2003 |
| WO | 03/043686 A1 | 5/2003 |
| WO | 03/047675 A2 | 6/2003 |
| WO | 2004/018031 A2 | 3/2004 |
| WO | 2005002659 A1 | 1/2005 |
| WO | 2004106203 A3 | 3/2005 |
| WO | 2005/074412 A2 | 8/2005 |
| WO | 2005/087306 A1 | 9/2005 |
| WO | 2006062996 A2 | 6/2006 |
| WO | 2007006055 A2 | 1/2007 |
| WO | 2007/032343 A1 | 3/2007 |
| WO | 2007094841 A1 | 8/2007 |
| WO | 2007098355 A1 | 8/2007 |
| WO | 2007098359 A1 | 8/2007 |
| WO | 2008005618 A2 | 1/2008 |
| WO | 2008030999 A2 | 3/2008 |
| WO | 2008/131300 A2 | 10/2008 |
| WO | 2008/137956 A2 | 11/2008 |
| WO | 2009/001309 A1 | 12/2008 |
| WO | 2008147600 A1 | 12/2008 |
| WO | 2009031161 A1 | 3/2009 |
| WO | 2009114837 A2 | 9/2009 |
| WO | 2009/124990 A1 | 10/2009 |
| WO | 2010015676 A1 | 2/2010 |
| WO | 2010/048449 A2 | 4/2010 |
| WO | 2010/132608 A2 | 11/2010 |
| WO | 2011036574 A1 | 3/2011 |
| WO | 2011143621 A1 | 11/2011 |
| WO | 2012106266 A1 | 8/2012 |
| WO | 2012154277 A1 | 11/2012 |
| WO | 2012166746 A1 | 12/2012 |
| WO | 2012174109 A1 | 12/2012 |

(56) References Cited

FOREIGN PATENT DOCUMENTS

| | | | |
|---|---|---|---|
| WO | 2013119557 A1 | 8/2013 | |
| WO | 2013126446 A1 | 8/2013 | |
| WO | 2013187827 A1 | 12/2013 | |
| WO | 2014006403 A1 | 1/2014 | |
| WO | 2014029424 A1 | 2/2014 | |
| WO | 2014074417 A2 | 5/2014 | |
| WO | 2014081942 A1 | 5/2014 | |
| WO | 2014/123848 A1 | 8/2014 | |
| WO | 2014120741 A1 | 8/2014 | |
| WO | 2014133617 A1 | 9/2014 | |
| WO | 2014140257 A1 | 9/2014 | |
| WO | 2014140265 A1 | 9/2014 | |
| WO | 2014/165783 A1 | 10/2014 | |
| WO | 2014158908 A1 | 10/2014 | |
| WO | 2014182421 A1 | 11/2014 | |
| WO | 2014197656 A1 | 12/2014 | |
| WO | 2014204593 A1 | 12/2014 | |
| WO | 2015017136 A1 | 2/2015 | |
| WO | 2015024904 A1 | 2/2015 | |
| WO | 2015035393 A1 | 3/2015 | |
| WO | 2015058136 A1 | 4/2015 | |
| WO | 15108913 A1 | 7/2015 | |
| WO | 2015/168655 A2 | 11/2015 | |
| WO | 15164912 A1 | 11/2015 | |
| WO | WO-2015168655 A2 * | 11/2015 | ........ A61M 25/0097 |
| WO | 2016/037127 A1 | 3/2016 | |
| WO | 16178974 A1 | 11/2016 | |
| WO | 2018/049413 A1 | 3/2018 | |
| WO | 2018170349 A1 | 9/2018 | |
| WO | WO-2018170349 A1 * | 9/2018 | ........ A61M 25/0113 |
| WO | 2019173641 A1 | 9/2019 | |

OTHER PUBLICATIONS

U.S. Appl. No. 14/866,738, filed Sep. 25, 2015 Notice of Allowance dated Sep. 24, 2020.
U.S. Appl. No. 15/154,384, filed May 13, 2016 Final Office Action dated Dec. 24, 2020.
U.S. Appl. No. 15/862,380, filed Jan. 4, 2018 Final Office Action dated Oct. 26, 2020.
U.S. Appl. No. 15/869,872, filed Jan. 12, 2018 Advisory Action dated Sep. 23, 2020.
U.S. Appl. No. 16/292,076, filed Mar. 4, 2019 Corrected Notice of Allowance dated Feb. 25, 2021.
U.S. Appl. No. 16/292,076, filed Mar. 4, 2019 Notice of Allowance dated Feb. 4, 2021.
U.S. Appl. No. 16/295,906, filed Mar. 7, 2019 Final Office Action dated Dec. 22, 2020.
U.S. Appl. No. 16/296,087, filed Mar. 7, 2019 Restriction Requirement dated Feb. 8, 2021.
U.S. Appl. No. 16/529,602, filed Aug. 1, 2019 Notice of Allowance dated Jan. 19, 2021.
U.S. Appl. No. 29/654,521, filed Jun. 25, 2018 Notice of Allowability dated Sep. 30, 2020.
U.S. Appl. No. 29/654,527, filed Jun. 25, 2018 Notice of Allowability dated Sep. 30, 2020.
U.S. Appl. No. 16/296,087, filed Mar. 7, 2019 Final Office Action dated Sep. 10, 2021.
U.S. Appl. No. 16/450,800, filed Jun. 24, 2019 Notice of Allowance dated Nov. 3, 2021.
U.S. Appl. No. 16/490,023, filed Aug. 29, 2019 Non-Final Office Action dated Oct. 4, 2021.
U.S. Appl. No. 14/099,050, filed Dec. 6, 2013 Advisory Action dated Jun. 1, 2017.
U.S. Appl. No. 14/099,050, filed Dec. 6, 2013 Final Office Action dated Jan. 30, 2017.
U.S. Appl. No. 14/099,050, filed Dec. 6, 2013 Non-Final Office Action dated Dec. 22, 2015.
U.S. Appl. No. 14/099,050, filed Dec. 6, 2013 Non-Final Office Action dated Jul. 19, 2016.
U.S. Appl. No. 14/099,050, filed Dec. 6, 2013 Notice of Allowance dated Sep. 14, 2017.
U.S. Appl. No. 14/099,050, filed Dec. 6, 2013 Notice of Panel Decision dated Aug. 1, 2017.
U.S. Appl. No. 14/167,149, filed Jan. 29, 2014 Non-Final Office Action dated Oct. 21, 2015.
U.S. Appl. No. 14/167,149, filed Jan. 29, 2014 Notice of Allowance dated Jul. 6, 2016.
U.S. Appl. No. 14/174,071, filed Feb. 6, 2014 Final Office Action dated Dec. 2, 2016.
U.S. Appl. No. 14/174,071, filed Feb. 6, 2014 Non-Final Office Action dated Jul. 29, 2016.
U.S. Appl. No. 14/174,071, filed Feb. 6, 2014 Non-Final Office Action dated Mar. 31, 2016.
U.S. Appl. No. 14/192,541, filed Feb. 27, 2014 Non-Final Office Action dated Jul. 20, 2016.
U.S. Appl. No. 14/192,541, filed Feb. 27, 2014 Notice of Allowance dated Dec. 6, 2016.
U.S. Appl. No. 14/192,541, filed Feb. 27, 2014 Notice of Corrected Allowability dated Mar. 8, 2017.
U.S. Appl. No. 14/250,093, filed Apr. 10, 2014 Advisory Action dated May 19, 2017.
U.S. Appl. No. 14/250,093, filed Apr. 10, 2014 Examiner's Answer dated Jun. 20, 2018.
U.S. Appl. No. 14/250,093, filed Apr. 10, 2014 Final Office Action dated Mar. 9, 2017.
U.S. Appl. No. 14/250,093, filed Apr. 10, 2014 Final Office Action dated Nov. 6, 2017.
U.S. Appl. No. 14/250,093, filed Apr. 10, 2014 Non-Final Office Action dated Nov. 16, 2016.
U.S. Appl. No. 14/250,093, filed Apr. 10, 2014 Notice of Allowance dated Aug. 19, 2020.
U.S. Appl. No. 14/250,093, filed Apr. 10, 2014 Panel Decision dated Jul. 14, 2017.
U.S. Appl. No. 14/250,093, filed Apr. 10, 2014 Patent Board Decision dated Jun. 8, 2020.
U.S. Appl. No. 14/477,717, filed Sep. 4, 2014, Notice of allowance dated Feb. 17, 2015.
U.S. Appl. No. 14/477,717, filed Sep. 4, 2014, Office action dated Dec. 18, 2014.
U.S. Appl. No. 14/585,800, filed Dec. 30, 2014 Final Office Action dated May 11, 2018.
U.S. Appl. No. 14/585,800, filed Dec. 30, 2014 Non-Final Office Action dated May 16, 2016.
U.S. Appl. No. 14/585,800, filed Dec. 30, 2014 Non-Final Office Action dated Nov. 29, 2016.
U.S. Appl. No. 14/585,800, filed Dec. 30, 2014 Non-Final Office Action dated Nov. 3, 2017.
U.S. Appl. No. 14/585,800, filed Dec. 30, 2014 Non-Final Office Action dated Oct. 8, 2015.
U.S. Appl. No. 14/585,800, filed Dec. 30, 2014 Notice of Allowance dated Feb. 25, 2019.
U.S. Appl. No. 14/585,800, filed Dec. 30, 2014 Notice of Allowance dated Jul. 3, 2017.
U.S. Appl. No. 14/702,580, filed May 1, 2015 Advisory Action dated Nov. 13, 2017.
U.S. Appl. No. 14/702,580, filed May 1, 2015 Final Office Action dated Sep. 1, 2017.
U.S. Appl. No. 14/702,580, filed May 1, 2015 Non-Final Office Action dated May 3, 2017.
U.S. Appl. No. 14/702,580, filed May 1, 2015 Notice of Allowance dated Decembers, 2017.
U.S. Appl. No. 14/750,658, filed Jun. 25, 2016 Non-Final Office Action dated Mar. 9, 2017.
U.S. Appl. No. 14/750,658, filed Jun. 25, 2016 Notice of Allowance dated Jul. 20, 2017.
U.S. Appl. No. 14/846,387, filed Sep. 4, 2015 Advisory Action dated May 10, 2018.
U.S. Appl. No. 14/846,387, filed Sep. 4, 2015 Final Office Action dated Mar. 22, 2018.
U.S. Appl. No. 14/846,387, filed Sep. 4, 2015 Non-Final Office Action dated Sep. 22, 2017.

(56) References Cited

OTHER PUBLICATIONS

U.S. Appl. No. 14/846,387, filed Sep. 4, 2015 Notice of Allowance dated Oct. 29, 2018.
U.S. Appl. No. 14/866,441, filed Sep. 25, 2015 Advisory Action dated Dec. 22, 2016.
U.S. Appl. No. 14/866,441, filed Sep. 25, 2015 Final Office Action dated Jun. 5, 2018.
U.S. Appl. No. 14/866,441, filed Sep. 25, 2015 Final Office Action dated Sep. 23, 2016.
U.S. Appl. No. 14/866,441, filed Sep. 25, 2015 Non-Final Office Action dated Apr. 7, 2017.
U.S. Appl. No. 14/866,441, filed Sep. 25, 2015 Non-Final Office Action dated Mar. 14, 2016.
U.S. Appl. No. 14/866,441, filed Sep. 25, 2015 Notice of Allowance dated Oct. 17, 2018.
U.S. Appl. No. 14/866,738, filed Sep. 25, 2015 Final Office Action dated Feb. 24, 2017.
U.S. Appl. No. 14/866,738, filed Sep. 25, 2015 Non-Final Office Action dated Nov. 6, 2017.
U.S. Appl. No. 14/866,738, filed Sep. 25, 2015 Non-Final Office Action dated Oct. 31, 2016.
U.S. Appl. No. 14/866,738, filed Sep. 25, 2015 Notice of Panel Decision dated Jun. 23, 2017.
U.S. Appl. No. 14/866,738, filed Sep. 25, 2015 Patent Board Decision dated Jul. 13, 2020.
U.S. Appl. No. 14/876,735, filed Oct. 6, 2015 Non-Final Office Action dated Mar. 30, 2017.
U.S. Appl. No. 15/154,384, filed May 13, 2016 Final Office Action dated Nov. 27, 2019.
U.S. Appl. No. 15/154,384, filed May 13, 2016 Non-Final Office Action dated Jun. 26, 2020.
U.S. Appl. No. 15/154,384, filed May 13, 2016 Non-Final Office Action dated Jun. 28, 2019.
U.S. Appl. No. 15/154,384, filed May 13, 2016 Restriction Requirment dated Jan. 25, 2019.
U.S. Appl. No. 15/154,808, filed May 13, 2016 Advisory Action dated Oct. 26, 2018.
U.S. Appl. No. 15/154,808, filed May 13, 2016 Final Office Action dated Aug. 16, 2018.
U.S. Appl. No. 15/154,808, filed May 13, 2016 Non-Final Office Action dated Apr. 6, 2018.
U.S. Appl. No. 15/154,808, filed May 13, 2016 Notice of Allowance dated Apr. 16, 2019.
U.S. Appl. No. 15/154,808, filed May 13, 2016 Restriction Requirement dated Jan. 3, 2018.
U.S. Appl. No. 15/377,880, filed Dec. 13, 2016 Final Office Action dated Oct. 19, 2018.
U.S. Appl. No. 15/377,880, filed Dec. 13, 2016 Non-Final Office Action dated May 14, 2018.
U.S. Appl. No. 15/481,773, filed Apr. 7, 2017 Final Office Action dated Jan. 10, 2019.
U.S. Appl. No. 15/481,773, filed Apr. 7, 2017 Non-Final Office Action dated Jun. 29, 2018.
U.S. Appl. No. 15/608,802, filed May 30, 2017 Non-Final Office Action dated Jun. 6, 2019.
U.S. Appl. No. 15/692,915, filed Aug. 31, 2017 Non-Final Office Action dated Jan. 29, 2018.
U.S. Appl. No. 15/702,537, filed Sep. 12, 2017 Final Office Action dated Mar. 8, 2019.
U.S. Appl. No. 15/702,537, filed Sep. 12, 2017 Non-Final Office Action dated Nov. 29, 2018.
U.S. Appl. No. 15/702,537, filed Sep. 12, 2017 Notice of Allowance dated Jul. 31, 2019.
U.S. Appl. No. 15/727,528, filed Oct. 6, 2017 Final Office Action dated Jan. 28, 2020.
U.S. Appl. No. 15/727,528, filed Oct. 6, 2017 Non-Final Office Action dated Sep. 20, 2019.
U.S. Appl. No. 15/727,528, filed Oct. 6, 2017 Restriction Requirement dated Aug. 7, 2019.
U.S. Appl. No. 15/727,528, filed Oct. 6, 2017 Notice of Allowance dated Mar. 27, 2020.
U.S. Appl. No. 15/862,380, filed Jan. 4, 2018 Non-Final Office Action dated Jul. 9, 2020.
U.S. Appl. No. 15/862,380, filed Jan. 4, 2018 Restriction Requirement dated Dec. 23, 2019.
U.S. Appl. No. 15/869,872, filed Jan. 12, 2018 Final Office Action dated Jun. 25, 2020.
U.S. Appl. No. 15/869,872, filed Jan. 12, 2018 Non-Final Office Action dated Apr. 10, 2020.
U.S. Appl. No. 15/951,931, filed Apr. 12, 2018 Non-Final Office Action dated Nov. 19, 2019.
U.S. Appl. No. 15/951,931, filed Apr. 12, 2018 Notice of Allowance dated Feb. 20, 2020.
U.S. Appl. No. 15/951,931, filed Apr. 12, 2018 Notice of Allowability dated Apr. 16, 2020.
U.S. Appl. No. 15/951,954, filed Apr. 12, 2018 Non-Final Office Action dated Nov. 4, 2019.
U.S. Appl. No. 15/951,954, filed Apr. 12, 2018 Notice of Allowability dated Apr. 7, 2020.
U.S. Appl. No. 16/138,523, filed Sep. 21, 2018 Notice of Allowance dated Mar. 26, 2020.
U.S. Appl. No. 16/292,076, filed Mar. 4, 2019 Non-Final Office Action dated Aug. 10, 2020.
U.S. Appl. No. 16/295,906, filed Mar. 7, 2019 Non-Final Office Action dated Sep. 4, 2020.
U.S. Appl. No. 29/536,043, filed Aug. 12, 2015 Final Office Action dated Mar. 26, 2018.
U.S. Appl. No. 29/536,043, filed Aug. 12, 2015 Non-Final Office Action dated Aug. 31, 2017.
U.S. Appl. No. 29/545,436, filed Nov. 12, 2015 Final Office Action dated Mar. 26, 2018.
U.S. Appl. No. 29/545,436, filed Nov. 12, 2015 Non-Final Office Action dated Sep. 12, 2017.
U.S. Appl. No. 29/654,521, filed Jun. 25, 2018 Notice of Allowance dated Aug. 17, 2020.
U.S. Appl. No. 29/654,521, filed Jun. 25, 2018 Restriction Requirement dated Apr. 8, 2020.
U.S. Appl. No. 29/654,527, filed Jun. 25, 2018 Notice of Allowance dated Aug. 18, 2020.
U.S. Appl. No. 29/654,527, filed Jun. 25, 2018 Restriction Requirement dated Mar. 10, 2020.
U.S. Appl. No. 29/658,136, filed Jul. 27, 2018 Non-Final Office Action dated Sep. 9, 2020.
U.S. Appl. No. 29/658,136, filed Jul. 27, 2018 Restriction Requirement dated May 11, 2020.
Waltimire, B. and Rasor, J.S., Midline catheter: Virtually bloodless insertion technique and needle safety tube minimize potential for transmission of bloodborne disease. Sponsored by national Foundation for Infectious Diseases. 5th National forum on AIDS, Hepatitis, and other blood-borne diseases. Atlanta, GA, Mar. 1992.
JP 2016-107046 filed May 30, 2016 Office Action dated Jul. 28, 2016.
JP 2016-563441 filed Oct. 19, 2016 Office Action dated Jan. 25, 2019.
JP 2018-039302 filed Mar. 6, 2018 Office Action dated Feb. 20, 2019.
Menlo Care, Landmark™ Aquavene® Catheters Brochure, 1992.
Menlo Care, Landmark® Midline Catheter Maintenance and Reference Guide (1993).
Menlo Care, Landmark® Midline Catheters Brochure, 1991.
Menlo Care, Landmark® Venous Access Device Insertion Instructions (1992).
Menlo Care, Publications on Aquavene® Technology, Aug. 1992.
Notice of allowance dated Jan. 29, 2014 for U.S. Appl. No. 12/307,519.
Notice of allowance dated Jun. 10, 2015 for U.S. Appl. No. 11/577,491.
Office action dated Mar. 10, 2011 for U.S. Appl. No. 12/307,519.
Office action dated Mar. 15, 2011 for U.S. Appl. No. 11/577,491.
Office action dated Mar. 27, 2013 for U.S. Appl. No. 13/358,099.
Office action dated Aug. 2, 2010 for U.S. Appl. No. 11/577,491.
Office action dated Aug. 18, 2014 for U.S. Appl. No. 11/577,491.

(56) References Cited

OTHER PUBLICATIONS

Office action dated Oct. 25, 2010 for U.S. Appl. No. 12/307,519.
Office action dated Nov. 4, 2013 for U.S. Appl. No. 12/307,519.
Office action dated Mar. 12, 2015 for U.S. Appl. No. 11/577,491.
PCT/CN2017/075370 filed Mar. 1, 2017 International Search Report and Written Opinion dated Nov. 30, 2017.
PCT/US15/28950 filed May 1, 2015 International Search Report and Written Opinion dated Oct. 19, 2015.
PCT/US2011/036530 filed May 13, 2011 International Search Report dated Oct. 6, 2011.
PCT/US2011/036530 filed May 13, 2011 Written Opinion of the International Searching Authority dated Oct. 6, 2011.
PCT/US2012/026618 International Preliminary Report on Patentability dated Aug. 27, 2013.
PCT/US2012/026618 International Search Report and Written Opinion dated Jun. 25, 2012.
PCT/US2013/073577 filed Dec. 6, 2013 International Search Report and Written Opinion dated Feb. 24, 2014.
PCT/US2014/013557 filed Jan. 29, 2014 International search report and written opinion dated Apr. 14, 2014.
PCT/US2015/048676 filed Sep. 4, 2015 International search report and written opinion dated Dec. 4, 2015.
PCT/US2016/032449 filed May 13, 2016 International Search Report and Written Opinion dated Oct. 5, 2016.
PCT/US2016/032534 filed May 13, 2016 International Search Report and Written Opinion dated Oct. 5, 2016.
PCT/US2017/051214 filed Sep. 12, 2017 International Search Report and Written Opinion dated Nov. 13, 2017.
PR Newswire, Luther Medical Products, Inc. Receives Approval to Supply Improved Neonatal Product to Japan, Aug. 20, 1998.
Rasor, Julia S, Review of Catheter-related infection rates: comparison of conventional catheter materials with Aquavene®, JVAN vol. 1, No. 3, Spring 1991.
RU 2017141812 filed Nov. 30, 2017 Office Action dated Jan. 31, 2018.
SG 11201709185X filed Nov. 8, 2017 Office Action dated Oct. 5, 2018.
SG 11201709193S filed Nov. 8, 2017 Office Action dated Oct. 5, 2018.
U.S. Appl. No. 12/598,053, filed Apr. 20, 2010 Notice of allowance dated Jan. 16, 2014.
U.S. Appl. No. 12/598,053, filed Apr. 20, 2010 Office action dated Aug. 28, 2013.
U.S. Appl. No. 12/598,053, filed Apr. 20, 2010 Office action dated Dec. 4, 2012.
U.S. Appl. No. 12/598,053, filed Apr. 20, 2010 Office action dated May 8, 2013.
U.S. Appl. No. 12/598,053, filed Apr. 20, 2010 Office action dated Oct. 24, 2013.
U.S. Appl. No. 13/107,781, filed May 13, 2011 Final Office Action dated Jul. 18, 2014.
U.S. Appl. No. 13/107,781, filed May 13, 2011 Non-Final Office Action dated Dec. 30, 2013.
U.S. Appl. No. 13/405,096, filed Feb. 24, 2012 Advisory Action dated Apr. 18, 2014.
U.S. Appl. No. 13/405,096, filed Feb. 24, 2012 Final Office Action dated Jan. 31, 2014.
U.S. Appl. No. 13/405,096, filed Feb. 24, 2012 Non-Final Office Action dated Aug. 20, 2013.
U.S. Appl. No. 13/405,096, filed Feb. 24, 2012 Non-Final Office Action dated Nov. 18, 2014.
U.S. Appl. No. 13/405,096, filed Feb. 24, 2012 Notice of Allowance dated Mar. 11, 2015.
U.S. Appl. No. 14/044,623, filed Oct. 2, 2013 Notice of Allowance dated Nov. 6, 2014.
Access Scientific, The PICC Wand® Product Data Sheet, Revision F, May 22, 2012.
Access Scientific, The Powerwand® Extended Dwell Catheter Brochure (http://accessscientific.com/media/4Fr-POWERWAND-Brochure.pdf) last accessed Sep. 25, 2015.
BD Angiocath™ Autoguard™ Shielded IV Catheter Brochure, © 2001.
BD Medical Systems, I.V. Catheter Family Brochure (2006).
BD Saf-T-Intima™ Integrated Safety IV Catheter Brochure, © 2001.
Becton Dickinson, Insyte® AutoGuard™ Shielded I.V. Catheter Brochure, 1998.
CA 2,799,360 filed May 13, 2011 Office Action dated Jun. 7, 2017.
CN 201180029526.7 filed Dec. 14, 2012 First Office Action dated Apr. 21, 2014.
CN 2012800008866.6 filed Aug. 14, 2013 Second Office Action dated Aug. 17, 2015.
CN 201280008866.6 filed Aug. 14, 2013 First Office Action dated Dec. 31, 2014.
CN 201280008866.6 filed Aug. 14, 2013 Third Office Action dated Jan. 25, 2016.
CN 201380073657.4 filed Aug. 21, 2015 Office Action dated Jun. 28, 2017.
CN 201380073657.4 filed Aug. 21, 2015 Office Action dated Mar. 2, 2018.
CN 201480019467.9 filed Sep. 29, 2015 Office Action dated Apr. 6, 2017.
CN 201510079782.7 filed Feb. 13, 2015 Office Action dated Dec. 30, 2016.
CN 201510079782.7 filed Feb. 13, 2015 Office Action dated Feb. 5, 2018.
CN 201510079782.7 filed Feb. 13, 2015 Office Action dated Sep. 19, 2017.
CN 201580022407.7 filed Nov. 2, 2016 Office Action dated Jan. 31, 2019.
CN 201580022407.7 filed Nov. 2, 2016 Office Action dated Sep. 16, 2019.
Cook Medical "Lunderquist Extra-Stiff wire guide" (2012).
Endovascular Today "Coiled Stainless Steel Guidewires" Buyer's Guide pp. 13-20, (2012).
EP 07783404.2 filed Jan. 19, 2009 Office Action dated Apr. 16, 2019.
EP 07783404.2 filed Jan. 19, 2009 Office Action dated Mar. 7, 2018.
EP 11781384.0 filed Sep. 21, 2012 Extended European Search Report dated Oct. 31, 2017.
EP 12782187.4 filed Sep. 10, 2013 European search report and written opinion dated Aug. 30, 2016.
EP 12782187.4 filed Sep. 10, 2013 European search report and written opinion dated Dec. 17, 2015.
EP 12782187.4 filed Sep. 10, 2013 Office Action dated Apr. 24, 2018.
EP 12782187.4 filed Sep. 10, 2013 Office Action dated Nov. 28, 2018.
EP 13876666.2 filed Sep. 7, 2015 Extended European Search Report dated Sep. 20, 2016.
EP 15785819.2 filed Dec. 2, 2016 Extended European Search Report dated Dec. 4, 2017.
EP 16797029.2 filed Nov. 21, 2017 Extended European Search Report dated May 3, 2018.
EP 16797029.2 filed Nov. 21, 2017 Office Action dated Mar. 27, 2020.
EP 16797047.4 filed Dec. 6, 2017 Supplemental European Search Report dated Jan. 9, 2019.
EP 19181963.0 filed Jun. 24, 2019 Extended European Search Report dated Jul. 16, 2019.
EP17849786.3 filed Apr. 12, 2019 Extended European Search Report dated May 13, 2020.
European office action dated Apr. 21, 2008 for EP Application No. 06800027.2.
European office action dated Aug. 6, 2012 for EP Application No. 07783404.2.
European office action dated Oct. 5, 2010 for EP Application No. 07783404.2.
European search report and opinion dated Jul. 10, 2009 for EP Application No. 07783404.2.
Hadaway, Lynn C., A Midline Alternative to Central and Peripheral Venous Access, Caring Magazine, May 1990, pp. 45-50.

(56) References Cited

OTHER PUBLICATIONS

International search report and written opinion dated Apr. 2, 2012 for PCT/US2012/023192.
International search report and written opinion dated Oct. 23, 2008 for PCT/US2007/068393.
JP 2013-510353 filed Oct. 31, 2012 Office Action dated Dec. 15, 2016.
JP 2015-560173 filed Aug. 28, 2015 Office Action dated Aug. 2, 2018.
JP 2015-560173 filed Aug. 28, 2015 Office Action dated Sep. 19, 2017.
JP 2016-107046 filed May 30, 2016 Office Action dated Apr. 26, 2017.
U.S. Appl. No. 15/154,384, filed May 13, 2016 Notice of Allowance dated Apr. 29, 2021.
U.S. Appl. No. 15/154,384, filed May 13, 2016 Notice of Allowance dated Mar. 17, 2021.
U.S. Appl. No. 15/862,380, filed Jan. 4, 2018 Notice of Allowance dated Jun. 16, 2021.
U.S. Appl. No. 16/295,906, filed Mar. 7, 2019 Notice of Allowance dated Mar. 4, 2021.
U.S. Appl. No. 16/296,087, filed Mar. 7, 2019 Non-Final Office Action dated Mar. 26, 2021.
U.S. Appl. No. 16/389,719, filed Apr. 19, 2019 Final Office Action dated Jun. 14, 2021.
U.S. Appl. No. 16/389,719, filed Apr. 19, 2019 Non-Final Office Action dated Mar. 19, 2021.
U.S. Appl. No. 16/450,800, filed Jun. 24, 2019 Non-Final Office Action dated Jul. 9, 2021.
U.S. Appl. No. 16/490,023, filed Aug. 29, 2019 Restriction Requirement dated May 4, 2021.
U.S. Appl. No. 16/529,622, filed Aug. 1, 2019 Non-Final Office Action dated May 7, 2021.
U.S. Appl. No. 16/529,622, filed Aug. 1, 2019 Notice of Allowance dated Aug. 23, 2021.
U.S. Appl. No. 29/658,136, filed Jul. 27, 2018 Notice of Allowance dated Mar. 23, 2021.
U.S. Appl. No. 15/869,872, filed Jan. 12, 2018 Notice of Allowance dated Dec. 24, 2021.
U.S. Appl. No. 16/296,087, filed Mar. 7, 2019 Notice of Allowance dated Mar. 8, 2022.
U.S. Appl. No. 16/490,023, filed Aug. 29, 2019 Notice of Allowance dated Mar. 14, 2022.
U.S. Appl. No. 16/868,461, filed May 6, 2020 Final Office Action dated May 25, 2022.
U.S. Appl. No. 16/868,461, filed May 6, 2020 Non-Final Office Action dated Feb. 15, 2022.
EP 22159383.3 filed Mar. 1, 2022 Extended European Search Report dated May 30, 2022.
U.S. Appl. No. 16/696,844, filed Nov. 26, 2019 Non-Final Office Action dated Aug. 1, 2022.
U.S. Appl. No. 16/867,349, filed May 5, 2020 Non-Final Office Action dated Jun. 16, 2022.
PCT/US2019/052225 filed Sep. 20, 2019 International Search Report and Written Opinion dated Jun. 25, 2020.
PCT/US2020/046860 filed Aug. 18, 2020 International Search Report and Written Opinion dated Nov. 18, 2020.
U.S. Appl. No. 17/164,653, filed Feb. 1, 2021, Restriction Requirement dated Sep. 7, 2022.
U.S. Appl. No. 17/164,653, filed Feb. 1, 2021, Notice of Allowance dated Nov. 1, 2022.
U.S. Appl. No. 17/337,273, filed Jun. 2, 2021 Notice of Allowance dated Oct. 5, 2022.

\* cited by examiner

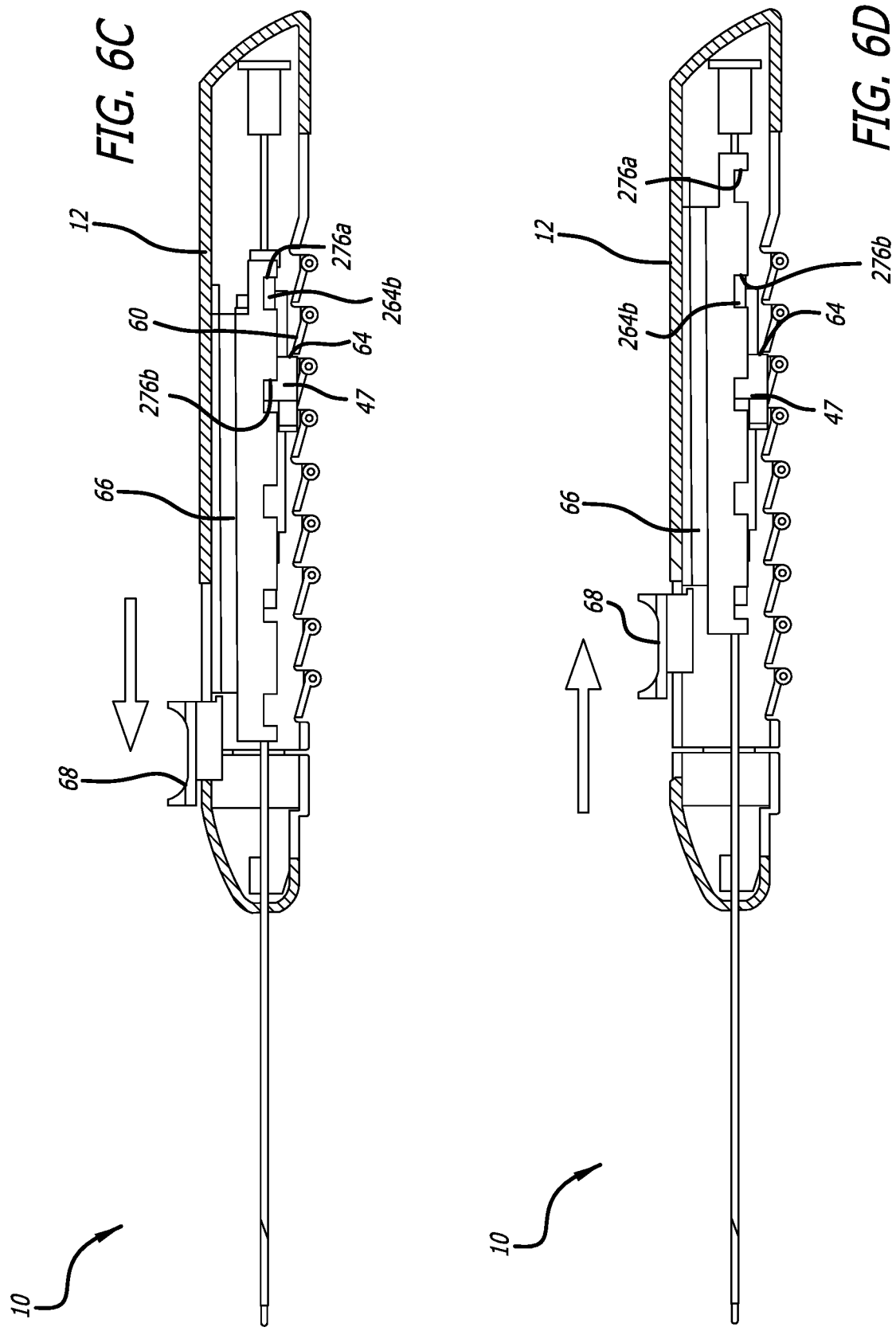

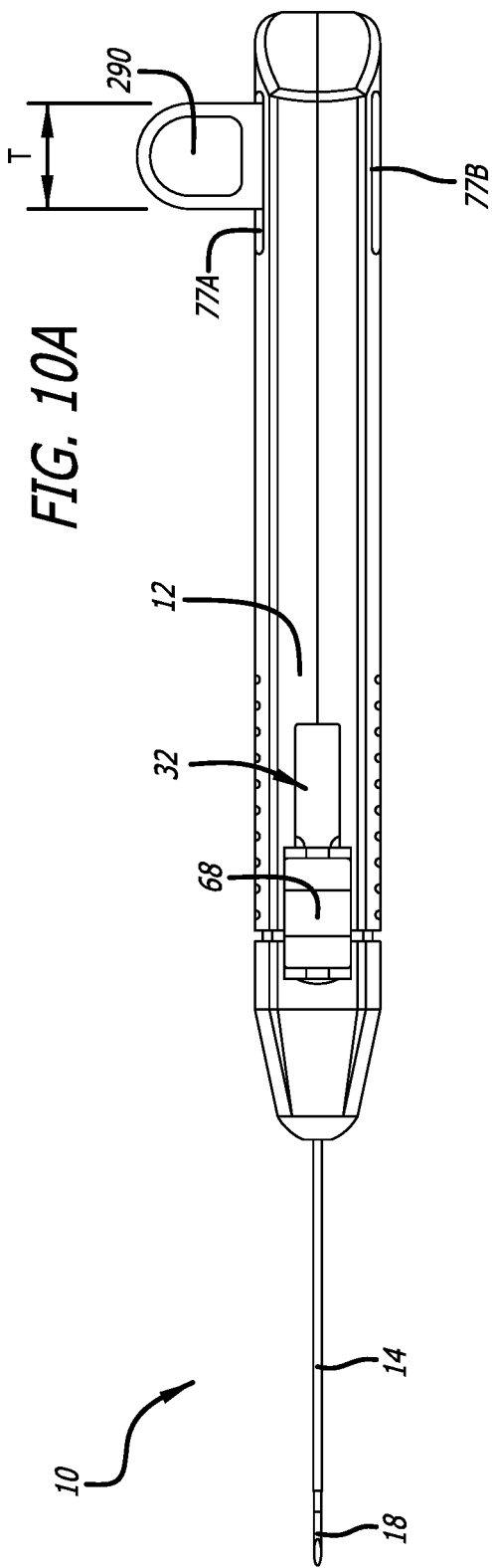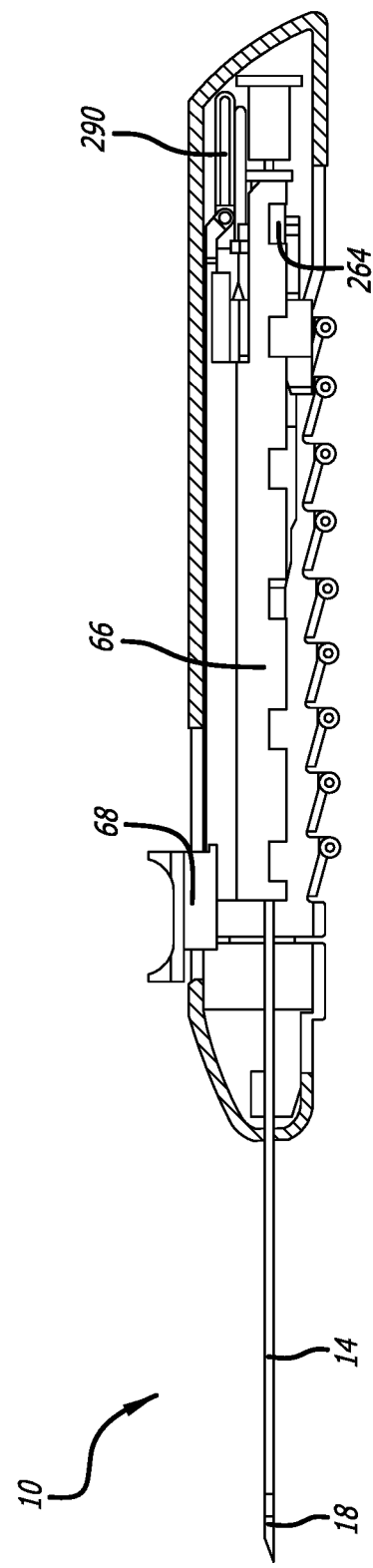

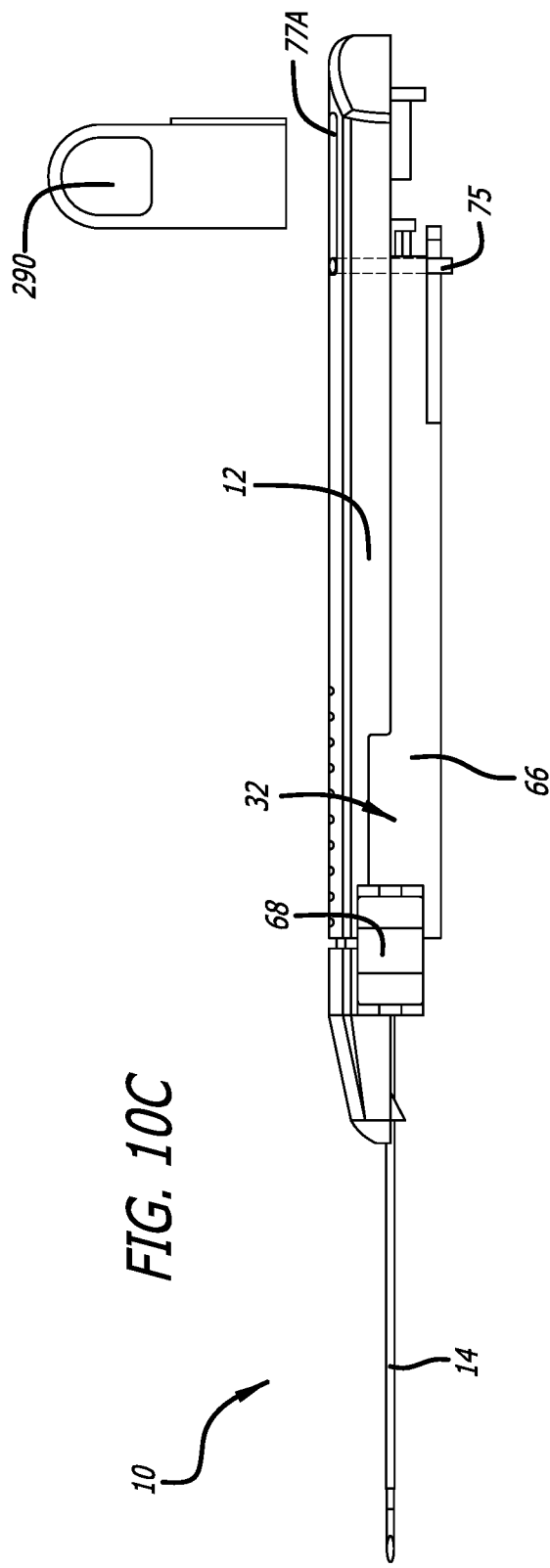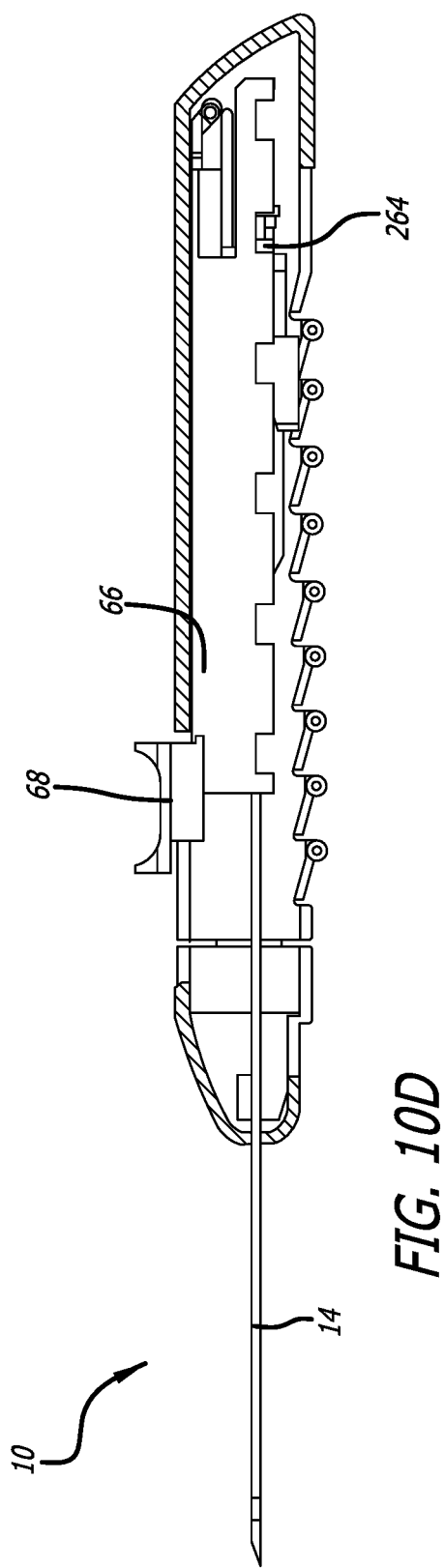

MIDLINE CATHETER PLACEMENT DEVICE

PRIORITY

This application claims the benefit of priority to U.S. Provisional Application No. 62/888,946, filed Aug. 19, 2019, which is incorporated by reference in its entirety into this application.

BACKGROUND

Midline catheters are generally used for parenteral nutrition, intravenous ("IV") fluid replacement and the administration of analgesics and antibiotics. Midline catheters are inserted at the bedside using sterile techniques and can remain in place for several weeks. The insertion (venipuncture) can be performed above and below the antecubital fossa in the cephalic, basilic, or brachial veins. The catheter tip is advanced 3 inches to 8 inches with the tip terminating below the axilla and proximal central veins.

The potential advantages of a midline catheter are the reduced frequency of repeated venipunctures for labs/restarts, decreased incidence of catheter related infections, extended implant/indwell duration, improved clinical outcomes, patient satisfaction and associated cost savings. Placing the catheter tip in the larger diameter veins in the upper arm compared to the smaller veins provide improved drug delivery therapy and hemodilution. Midline catheters can be used for infusing contrast media at higher flow rates that are typically done by central venous ("CV") catheters such as peripherally inserted central venous catheter ("PICC") applications.

Prior midline catheter devices typically include an integral guidewire. The guidewire is advanced through the lumen of the needle and into the vein after the needle accesses the vein. Often an ultrasonic probe or imaging device is used to locate the needle in the desired location. The catheter is then advanced over the guidewire into the vein. The needle and guidewire are then detached and separated from the catheter which remains in place in the vein.

These prior devices generally require the guidewire to be fully deployed by moving a sliding member into a locked/detent position. To advance the catheter, the user must put down the ultrasonic probe and use both hands to advance the catheter and complete the final steps of the procedure. This results in a loss of the visualization of the vein and the location of the catheter relative to the vein.

Catheter placement and advancement is dependent on holding the device in a stationary position with one hand while manipulating the catheter advancing mechanism in the other hand without the use of the ultrasonic imaging to assist in proper placement of the catheter. Once the catheter is fully advanced, the user must re-position the ultrasonic probe to re-establish the image and confirm proper placement of the catheter. The operation requires a series of sequential steps with specialized training. The additional exchange of hand positions from the ultrasonic probe to the device and back to the probe adds complexity to the procedure and risks the success of the proper placement of the catheter.

What is needed, therefore is a catheter placement device that streamlines the steps involved in catheter placement, as well as being operated with a single hand, while still providing the same functionality of current catheter placement devices.

SUMMARY

Briefly summarized, embodiments disclosed herein are directed to extended dwell peripheral IV catheter ("PIVC") devices that provide a longer length "mini-midline" catheter. The catheter would be placed similarly to a PIVC, without the need for a guidewire and would only require one-handed operation. Placement would be carried out under ultrasound imaging guidance and can access deeper vessels or facilitate difficult venous access ("DVA") procedures. The catheter would be able to successfully extend the dwell time for patients requiring medium/long term IV therapy, for example between 5 and 30 days.

Disclosed herein is a catheter placement device including, a housing, a needle extending from a distal end of the housing, a catheter assembly disposed coaxially over the needle, including a catheter supported by a catheter hub, and a safety assembly including a first indexing finger, and an actuator assembly configured to transition longitudinally between a first position and a second position, the actuator assembly including, an actuator button extending through an elongate opening in the housing, and an actuator body including a plurality of actuator abutments, wherein the first indexing finger engages a first actuator abutment of the plurality of actuator abutments and the actuator assembly distally advances the catheter assembly in a stepwise manner as the actuator assembly moves between the first position and the second position.

In some embodiments, the first indexing finger is integrally molded with the safety assembly to form a single structure, the first indexing finger configured to flexibly deform as the actuator body moves from the second position to the first position. The first indexing finger is supported by a collar and is formed as a separate structure from the safety assembly, the collar being coupled to the safety assembly, and the first indexing finger configured to flexibly deform as the actuator body moves from the second position to the first position. The housing includes a plurality of housing tabs that engage the safety assembly to prevent proximal movement thereof. The housing includes a plurality of housing abutments that engage a second indexing finger extending from the safety assembly to prevent proximal movement thereof.

In some embodiments, the actuator body includes a top wall, a first side wall, and a second side wall that define an inverse channel through which the catheter assembly moves along a longitudinal axis. One of the first side wall or the second side wall includes a plurality of notches that define the plurality of actuator abutments. One of the first side wall or the second side wall includes a plurality of apertures that define the plurality of actuator abutments. The housing includes a first door and a second door disposed at a distal end thereof and configured to pivot through a horizontal plane between an open position and a closed position. The housing includes a first housing half and a second housing half joined along a longitudinally vertical plane, the first door hingedly coupled to the first housing half and the second door hingedly coupled to the second housing half.

In some embodiments, the housing includes a first hinged door disposed at a distal end thereof and configured to pivot through a vertical plane. The housing includes a first housing half and a second housing half joined along a longitudinally horizontal plane, the first door hingedly coupled to the first housing half. In some embodiments, the catheter placement device further includes a lockout device that transitions between a locked position and an unlocked position, the locked position allowing a movement of the catheter relative to the needle and restricting distal advancement of the catheter assembly in the stepwise manner. The movement of the catheter relative to the needle is restricted to less than a longitudinal distance between the first actuator abutment and a second actuator abutment, adjacent to the first actuator abutment. The movement of the catheter relative to the needle is restricted to less than half a longitudinal distance between the first actuator abutment and a second actuator abutment, adjacent to the first actuator abutment. The movement of the catheter relative to the needle is restricted to a distance of between 1 mm to 3 mm.

In some embodiments, the lockout device includes a lockout button including an engagement arm having a first aperture defining a first diameter, and a second aperture defining a second diameter, the second diameter being larger than the first diameter, the first aperture communicating with the second aperture to define a keyhole shape that receives an anchor portion of the safety assembly therethrough. The lockout button transitions between the locked position and an unlocked position, the anchor portion is disposed within the first aperture in the locked position and the second aperture in the unlocked position. The anchor portion includes a flange that extends radially from a proximal end of the anchor portion, the flange defining a diameter that is larger than the first diameter and smaller than the second diameter, the flange abuts against the engagement arm when the lockout button is in the locked position.

In some embodiments, the lockout device includes a lockout collar slidably engaged with an outer surface of the housing and transitions longitudinally between the locked position and the unlocked position. The lockout collar encircles a longitudinal axis of the housing, the lockout collar covering a portion of the elongate opening in the locked position to restrict movement of the actuator assembly. The lockout collar is disposed between the actuator button and a first protrusion in the locked position, and between the first protrusion and a second protrusion in the unlocked position. The lockout device includes a lockout slider disposed on the actuator button and slides perpendicular to a longitudinal axis to engage a notch, when in the locked position. A longitudinal width of the slider is less than a longitudinal width of the notch to allow movement of the actuator button in the locked position and restrict distal advancement of the catheter assembly in the stepwise manner.

In some embodiments, the lockout slider in the unlocked position aligns with the actuator button to disengage the notch and allow the actuator assembly to move between the first position and the second position. The lockout device includes a lockout tab interposed between the actuator assembly and the housing in the locked position, which restricts movement of the actuator assembly. The lockout tab extends through a slot in the housing, the tab defining a longitudinal width that is less than a longitudinal length of the slot.

Also disclosed is a method of inserting a catheter including, providing a catheter insertion device having a housing, a needle extending from a distal end of the housing, an actuator assembly including an actuator button and an actuator body, a catheter assembly disposed coaxially over the needle having, a catheter supported by a catheter hub and a safety assembly, and a lockout device transitionable between a locked position and an unlocked position, the locked position permitting movement of the catheter relative to the needle and inhibiting advancement of the catheter in a stepwise manner, actuating the actuator button with the lockout device in the locked position to move the catheter relative to the needle, transitioning the lockout device from the locked position to the unlocked position, inserting the needle into a patient to access a vasculature thereof, and actuating the actuator button from a first position to a second position to advance the catheter in the stepwise manner relative to the needle.

In some embodiments, the actuator body includes a plurality of actuator abutments, and the safety assembly includes an indexing finger, the indexing finger engaging an actuator abutment of the plurality of actuator abutments as the actuator button moves from the first position to the second position, and the indexing finger deflecting as the actuator button moves from the second position to the first position.

Also disclosed is a method of advancing a catheter over a needle including, providing a catheter placement device having a housing including a plurality of housing tabs and a needle extending from a distal end thereof. The catheter placement device further having a catheter assembly including a catheter disposed coaxially over the needle and engaging a first housing tab of the plurality of housing tabs, an actuator assembly configured to move between a first position and a second position to advance the catheter assembly from the first housing tab to a second housing tab adjacent to the first housing tab, and a lockout device transitionable between a locked position and an unlocked position. The locked position restricts movement of the catheter assembly between the first housing tab and the second housing tab, and the unlocked position permits movement of the catheter assembly between the first housing tab and the second housing tab. The method further includes actuating the actuator button with the lockout device in the locked position to move the catheter relative to the needle while preventing the catheter assembly from advancing from the first housing tab to the second housing tab, transitioning the lockout device from the locked position to the unlocked position, inserting the needle into a patient to access a vasculature thereof, and actuating the actuator button from the first position to the second position to advance the catheter assembly from the first housing tab to the second housing tab.

In some embodiments, the lockout device is one of a lockout button, a lockout collar, a lockout slider and a lockout tab. The housing includes a first hinged door and a second hinged door, each disposed at the distal end of the housing and configured to pivot to an open position to release the catheter hub.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 6C-6D show cutaway side views of the catheter insertion device of FIG. 6A, in accordance with embodiments disclosed herein.

FIGS. 10A-10D show various views of a catheter insertion device including a lockout device, in accordance with embodiments disclosed herein.

DESCRIPTION

Figure 1:
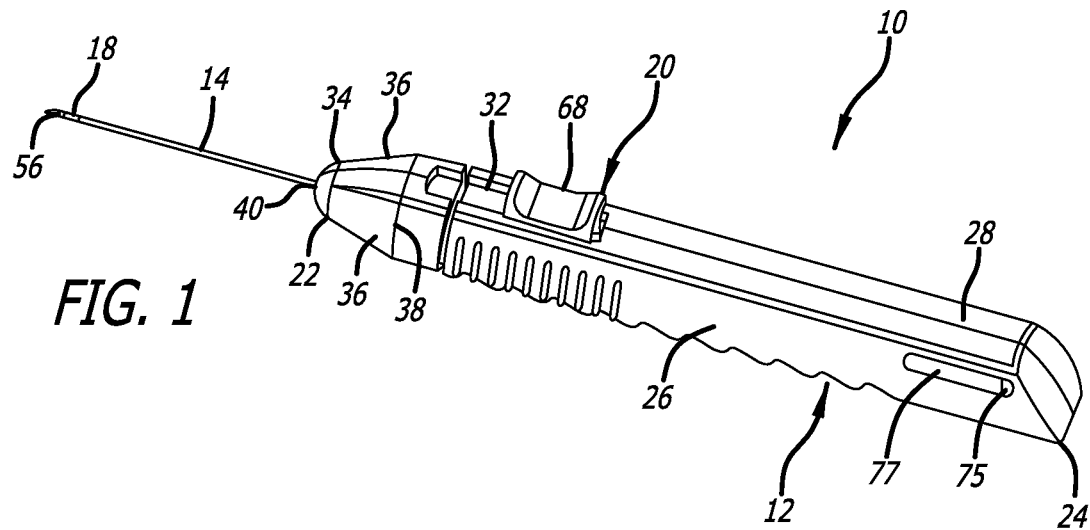
FIG. 1 shows a perspective view of a catheter insertion device showing the actuator in a starting position, in accordance with embodiments disclosed herein.

Reference will now be made to figures wherein like structures will be provided with like reference designations. It is understood that the drawings are diagrammatic and schematic representations of exemplary embodiments of the present invention, and are neither limiting nor necessarily drawn to scale.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

For clarity it is to be understood that the word "proximal" refers to a direction relatively closer to a user using the device to be described herein, while the word "distal" refers to a direction relatively further from the user. For example, with respect to "proximal," a "proximal portion" or a "proximal end portion" of, for example, a catheter disclosed herein includes a portion of the catheter intended to be near a user when the catheter is used on a patient. Likewise, a "proximal length" of, for example, the catheter includes a length of the catheter intended to be near the user when the catheter is used on the patient. A "proximal end" of, for example, the catheter includes an end of the catheter intended to be near the user when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter. Also, the words "including," "has," and "having," as used herein, including the claims, shall have the same meaning as the word "comprising."

The terms "needle" and "cannula" can be used herein interchangeably to refer to a member having a sharpened or beveled end for insertion into an injection site on a subject. In one embodiment, the needle can be a thin hollow tubular member.

Figure 4A:
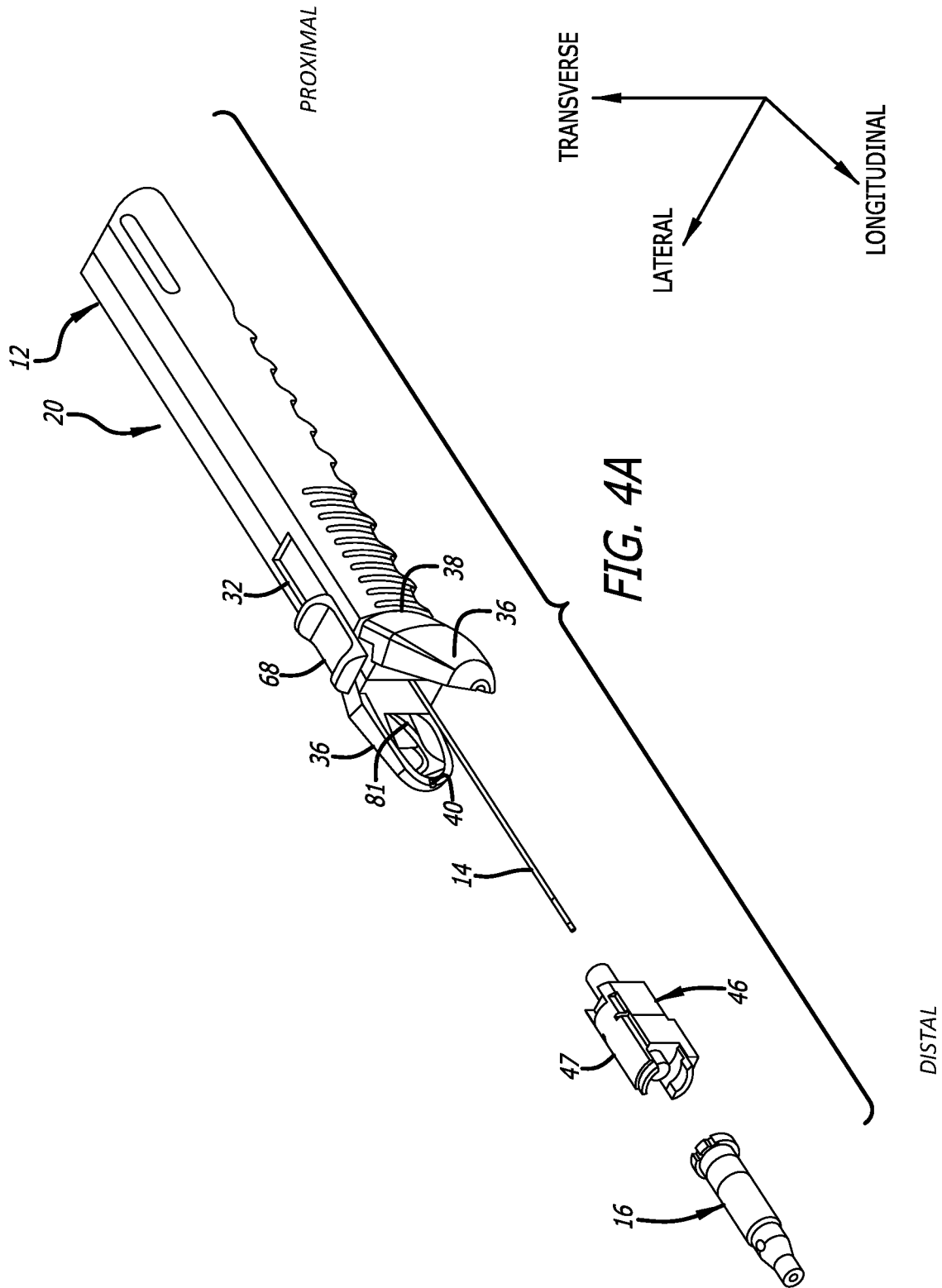
FIGS. 4A-4B show perspective exploded views of the catheter hub and safety assembly separated from the housing of a catheter insertion device, in accordance with embodiments disclosed herein.

As used herein, and as shown in FIG. 4A, the longitudinal axis extends parallel to an axial length of the catheter, a lateral axis extends normal to the longitudinal axis, and a transverse axis extends normal to both the longitudinal and lateral axes. As used herein, the "axial" means along or parallel to the longitudinal axis of the needle and the "radial" direction is a direction perpendicular to the axial direction. The forward direction is the direction toward the distal end of the device. The backward direction is the direction toward the proximal end of the device. Unless defined otherwise, all technical and scientific terms used herein have the same meaning as commonly understood by those of ordinary skill in the art.

Embodiments disclosed herein are directed to a catheter placement device, also termed "catheter insertion device," with a streamlined operation and the ability to be placed with a single hand, allowing a user to also operate an ultrasound probe, or the like, to maintain visualization.

Figure 2:
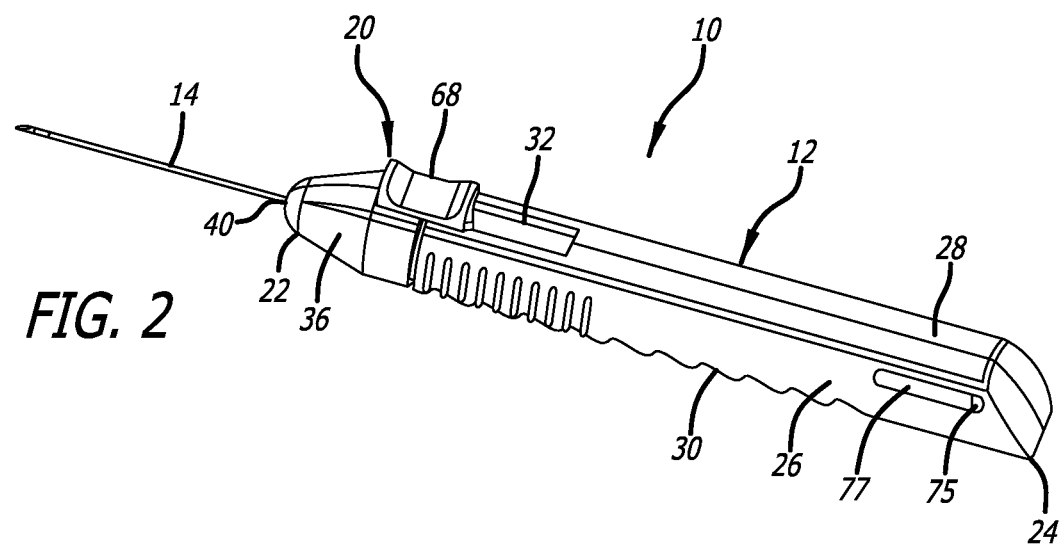
FIG. 2 shows a perspective view of the catheter insertion device of FIG. 1 showing the actuator in the forward actuated position, in accordance with embodiments disclosed herein.
Figure 3:
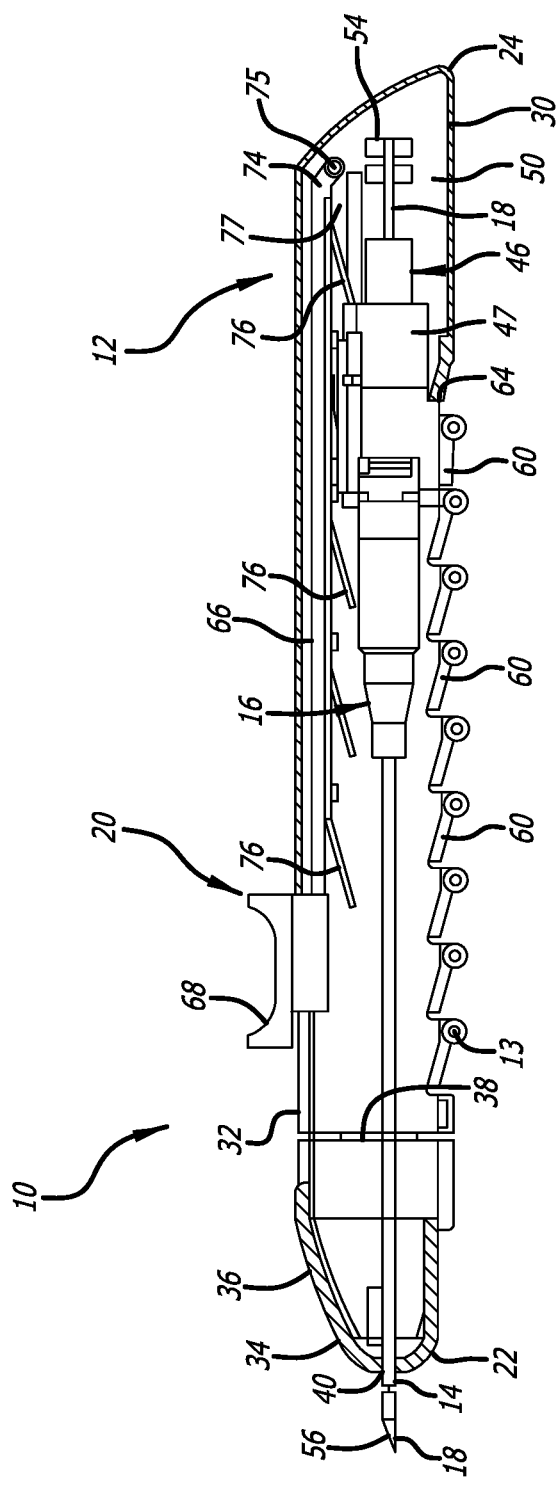
FIG. 3 shows a cutaway side view of the catheter insertion device of FIG. 1 showing the catheter and hub in the starting position, and with the introducer needle extending from the distal end of the catheter insertion device, in accordance with embodiments disclosed herein.

In reference to FIGS. 1-3, the catheter insertion device 10 generally includes a main body or housing 12, a catheter assembly, including a catheter 14 having a catheter hub 16 and a safety assembly 46, an introducer needle 18, and an actuator assembly 20. The actuator assembly 20 forms a shuttling or indexing assembly and mechanism to index and advance the catheter 14 over the end of the needle 18 in a stepwise manner by cycling through a plurality of stages. Each stage consisting of moving the actuator assembly 20 from a first position to a second position and back to the first position to advance the catheter assembly a given distance in a distal direction.

The housing 12 of the insertion device 10 has a longitudinal dimension with a distal end 22 and a proximal end 24. In an embodiment, the housing 12 can be formed from two housing halves that are joined together by a suitable attachment mechanism. For example, a first housing half and a second housing half can be aligned by one or more pins (not shown) protruding from a first housing half, which can correspond with one or more recesses 13 on a second housing half (FIG. 3). However, other configurations of pins and recesses, or similar attachment mechanisms including clips, lugs, notches, protrusions, combinations thereof, or the like are also contemplated. The housing 12 has a dimension for supporting the introducer needle 18 and catheter 14 during use and to enable the user to manipulate the device in positioning the catheter. Also shown in FIG. 3, the introducer needle 18 is hollow and has a proximal end fixed within an interior cavity 50 of the housing 12 by a post 54 or other support. The needle 18 extends from a distal end of the housing 12 through the opening 40 to a point that is distal of the distal end 22 of the housing 12.

The housing 12 can define an interior cavity 50 forming a longitudinal passage. In an embodiment, the housing 12 has curved side walls 26, a flat top wall 28 and a flat bottom wall 30. The flat bottom wall 30 is generally provided to allow the device to be placed on a flat surface in a stable position with reduced risk of falling off the surface. It will be appreciated that the shape of the device 10 can vary without limitation depending on the particular use to provide comfortable and convenient use by the operator.

In an embodiment, an elongated opening 32 is formed in the top wall 28 for receiving a portion of the actuator assembly 20 therethrough. The housing 12 can further include a tip portion ("tip") 34 having converging sides that defines the distal end 22 of the housing 12. As shown in FIG. 4A, two hinged doors 36 of tip 34 are hingedly connected to the walls 26 by a respective hinge 38. The hinged doors 36 can transition between a closed position (FIG. 1) and an open position (FIG. 4A) to access the interior cavity 50 of the housing 12 and allow removal of the catheter 14, catheter hub 16, safety assembly 46, or combinations thereof, from the housing 12. An outlet opening 40 in tip 34 enables the catheter 14 and introducer needle 18 to extend from the distal end of the housing 12 when the hinged doors 36 are in the closed configuration. The converging surfaces of tip 34 enable the device to be positioned at a low angle with respect to the skin of the patient to assist in inserting the catheter 14 and introducer needle 18 into the patient with reduced risk of kinking or folding of the catheter 14.

Further details of the catheter insertion device 10 can be found in International Patent Publication WO 2018/170349, which is incorporated by reference in its entirety into this application.

Figure 4B:
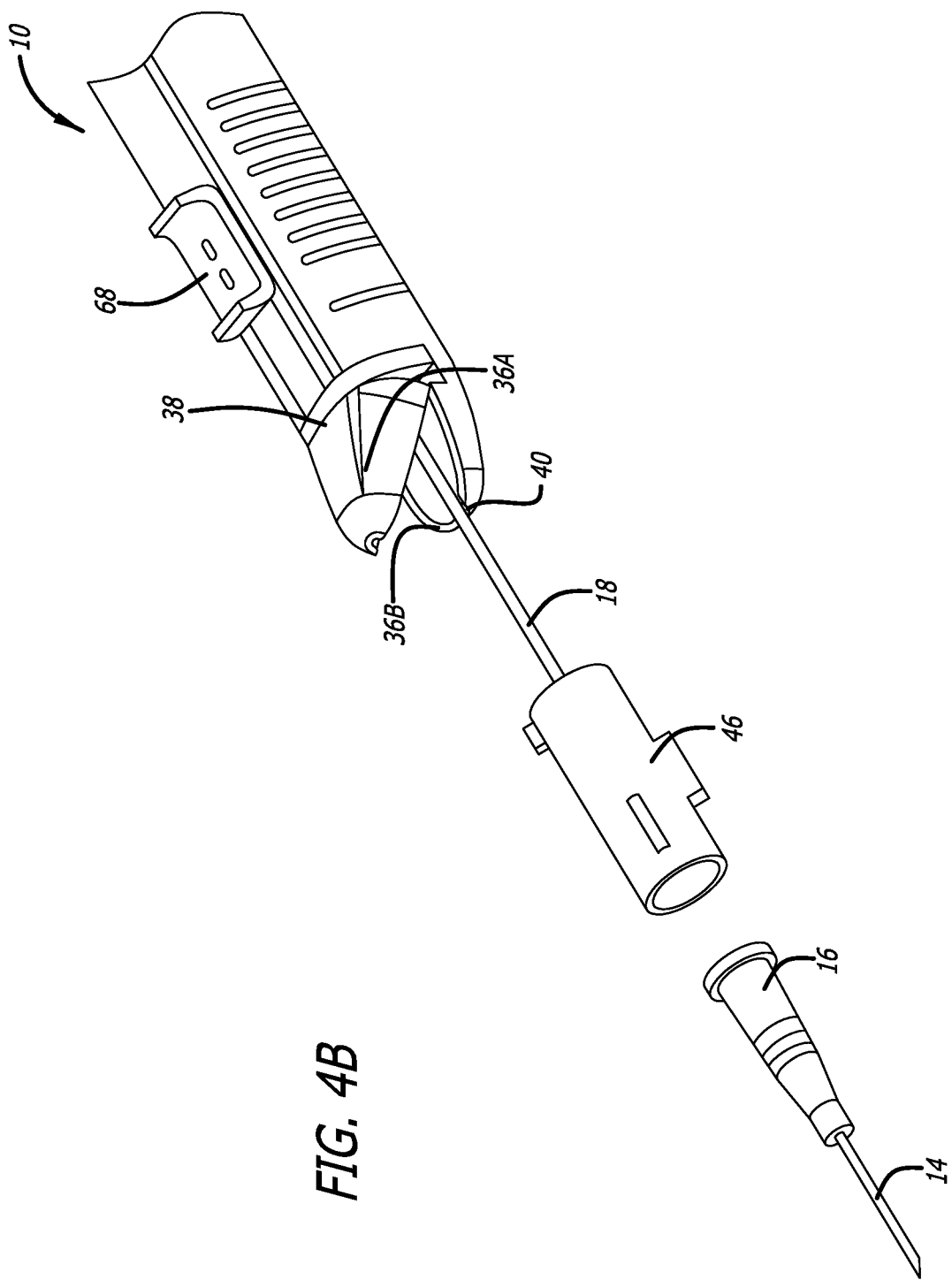

As shown in FIGS. 3-4B, in an embodiment, the actuator assembly 20 that forms the shuttling or indexing assembly, advances a catheter assembly, which includes the catheter 14, catheter hub 16, safety assembly 46, or combinations thereof, in a distal direction and in a stepwise manner through a series of stages. Each stage comprising of a back and a forward movement of the actuator assembly 20. A forward movement of the actuator assembly 20 causes an actuator tab 76 to engage a portion of the catheter assembly and urge the catheter assembly in a distal direction. At the completion of each forward stroke, the button 68 is pulled back and an adjacent tab 76 of the actuator body 66 is readied for the next forward stroke, by engaging the portion of the catheter assembly. As shown in FIG. 3, the housing can include a plurality of flexible tabs ("housing tabs") 60. Each tab of the housing tabs 60 can be configured to deflect to allow the catheter assembly, or portion thereof, to pass distally. Once the catheter assembly has advanced distally of a deflected tab 60, the tab 60 can return to the undeflected configuration. With each backward stroke, a housing tab 60 can engage the body 47 of the needle safety assembly 46 to prevent proximal movement of the catheter assembly. As shown, the starting position of the device 10 can be a retracted position (FIG. 1). However it will be appreciated that the starting position may also be an extended position (FIG. 2), the actuator assembly 20 can then be cycled through the backward and forward movement of each stage to advance the catheter assembly forward to a distal end of the housing 12.

Once the safety assembly body 47 and catheter hub 16 are advanced to a forward position, proximate a distal end 22 of housing 12, the hinged doors 36 are pivoted to the open position as shown in FIG. 4A to release catheter hub 16 and safety assembly 46, from the housing 12. In an embodiment, the doors 36 can transition to the open position by rotating through a longitudinally horizontal plane, as shown in FIG. 4A. The catheter hub 16 is advanced to contact cam surfaces 81 on the inner surface of the doors 36 to transition the doors 36 to the open position. The housing 12 can then be withdrawn proximally from catheter hub 16 to withdraw introducer needle 18 from catheter 14. The safety assembly body 47 slides over the distal end 56 of the introducer needle 18 to enclose the sharp tip and prevent an accidental needle stick injuries. The catheter hub 16 is released and separated from safety assembly 46 when the body 47 of safety assembly 46 is actuated by the withdrawing of introducer needle 18. Housing 12, with the attached introducer needle 18 and safety assembly body 47 can then be discarded. Optionally a seal forms a valve that closes a proximal end of the catheter hub 16 to control blood backflow and to allow attachment of an extension set or other devices.

As shown in FIG. 4B, in an embodiment, a first hinged door 36A can be hingedly coupled with a top wall 28 and a second hinged door 36B can be hingedly coupled with a bottom wall 30. As such, one of the first hinged door 36A or second hinged door 36B transitions to the open position by rotating through a longitudinally vertical plane, as shown in FIG. 4B. In an embodiment, a first door 36A can be hingedly coupled to the housing 12 and a second door 36B can be coupled to the housing 12 in a fixed relationship relative to the housing 12, e.g. attached thereto by adhesive, bonding, welding, etc. Advantageously, the second door 36 configured as such can provide a supporting structure for the needle 18 at the outlet opening 40 of tip 34. In an embodiment, the second door 36B is formed as integrally molded with the housing 12 to form a single structure. In an embodiment, the first door 36A can be coupled in a fixed relationship relative to the housing 12 and the second door 36B can be hinged coupled to the housing 12.

Advantageously, the hinging mechanisms of the doors 36 can simplify fabrication and/or assembly of the catheter insertion device 10 by following the bi-lateral symmetry of the device construction. For example, as shown in FIG. 4A, where the housing 12 is formed from two housing halves that are joined together along a longitudinally vertical plane, the hinged doors 36 can be coupled with the side walls 26.

Similarly, as shown in FIG. 4B, where the housing 12 is formed by joining two halves along a longitudinally horizontal plane, the hinged doors 36 can be coupled with the top and bottom walls 28, 30 to facilitate fabrication and assembly.

As shown in FIGS. 5A-5E, in an embodiment, the housing 12 includes a plurality of rigid abutments ("housing abutments") 260. Further, the actuator body 66 includes a plurality of rigid abutments ("actuator abutments") 276. As shown in FIGS. 5B-5E, the catheter assembly can include one or more indexing fingers 264. The indexing finger 264 can extend from a side wall of the safety assembly body 47 and can be angled towards a proximal end. The indexing finger 264 can be configured to elastically deflect inward towards a central axis, and can be biased to an outward position as shown in FIGS. 5B-5E.

In an embodiment, the safety assembly body 47 includes a first indexing finger 264A extending from a first side of the body 47 and a second indexing finger 264B extending from a second side of the body 47. In an embodiment, the first and second sides are opposite each other, although other configurations are contemplated. The first indexing finger 264A extends towards the actuator abutments 276 of the actuator body 66, and the second indexing finger 264B extends toward the housing abutments 260 of the housing 12.

Figure 5A:
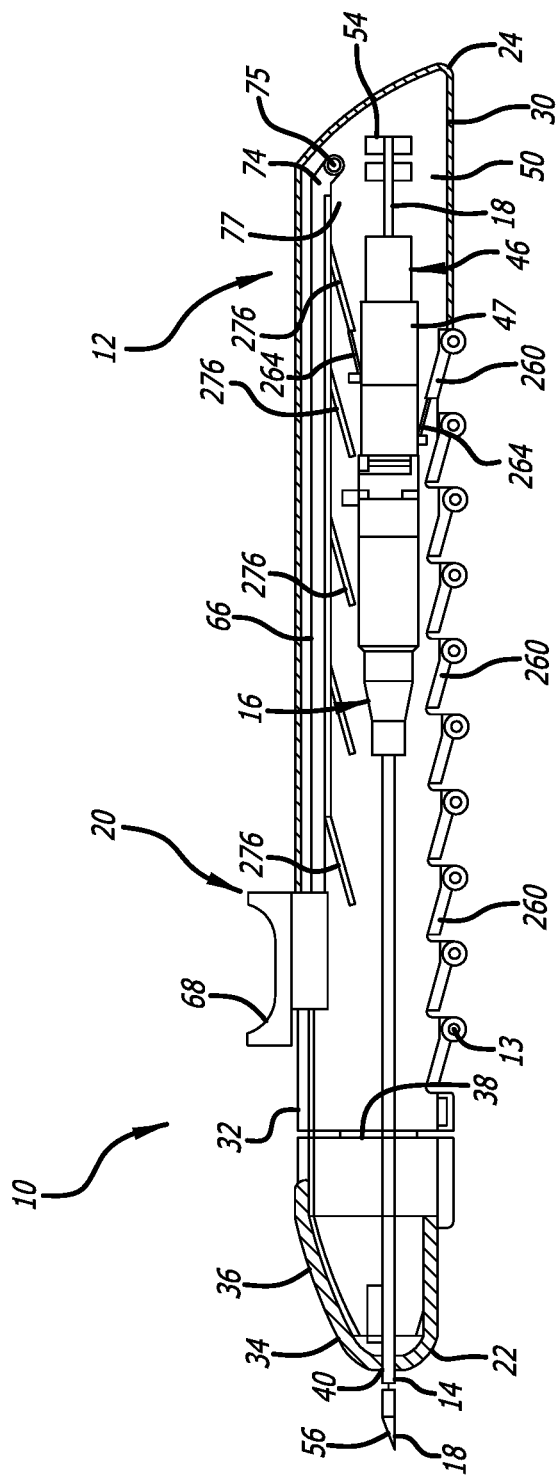
FIG. 5A shows a cutaway side view of a catheter insertion device showing the catheter and hub in the starting position, and with the introducer needle extending from the distal end of the catheter insertion device, in accordance with embodiments disclosed herein.

In use, the button 68 of the actuator assembly 20 is initially in the retracted position as shown in FIG. 5A, and the user can slide the button 68 forward to a second, extended position. An abutment 276 disposed toward the proximal end of the actuator body 66 engages the first indexing finger 264A disposed on an upper surface of the safety body 47 and slides the catheter assembly forward a distance corresponding to the distance of travel of the actuator button 68. The housing abutments 260 on the bottom wall 30 of the housing 12 are positioned to complement the spacing and location of the actuator abutments 276.

The forward movement of the safety body 47 toward the distal end 22 of the housing 12 causes the second indexing finger 264B to deflect until a proximal end thereof travels distally of a housing abutment 260. The indexing finger 264B, which is biased outwardly, then engages the housing abutment 260 to retain the body 47 in the advanced position and prevent the body 47 from sliding back toward the proximal end 24 of the housing 12. The advancing movement of the body 47 advances the catheter forward over the fixed introducer needle 18.

The button 68 can then slide backward toward the retracted position where the first indexing finger 264A deflects and slides over an adjacent actuator abutment 276 to engage a distally facing contact point thereon. Thus completing a stage cycle that advances the catheter assembly by a step of the stepwise advancement. The button 68 can then slide forward again to repeat the cycle where the first indexing finger 264A and the second indexing finger 264B can engage consecutive actuator abutments 276 and housing abutments 260 to advance the catheter 14 in a stepwise manner.

In an embodiment, the button 68 can slide between the retracted position and the extended position by manual manipulation by the user. In an embodiment, the catheter insertion device 10 can include a one or more biasing members, e.g. a spring, to transition the button 68 and actuator assembly between the retracted position and the extending position. For example, from the extended position to the retracted position, or from the retracted position to the extended position. Advantageously, the biasing member can facilitate one-handed use of the catheter insertion device 10 by automatically resetting the actuator assembly to one of the retracted or extended positions, ready for manual manipulation of the actuator assembly 20 in a subsequent step.

Figure 5B:
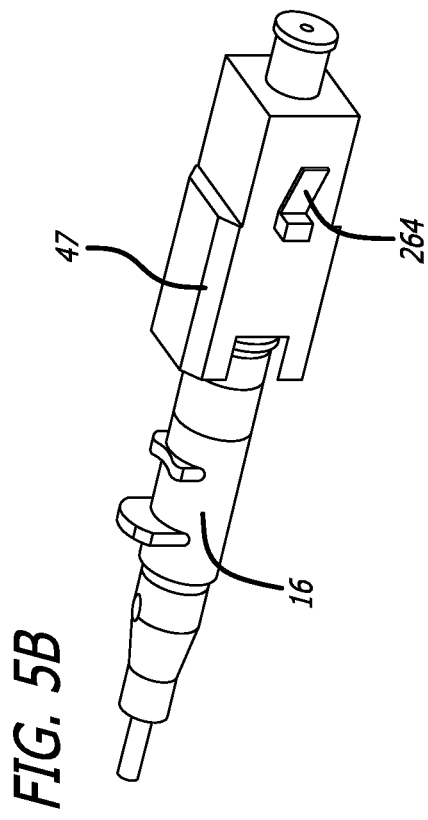
FIGS. 5B-5E show various views of a catheter hub and safety assembly, in accordance with embodiments disclosed herein.
Figure 5C:
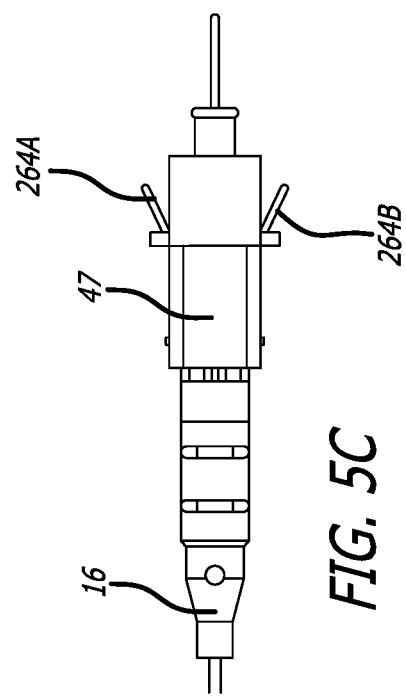
Figure 5D:
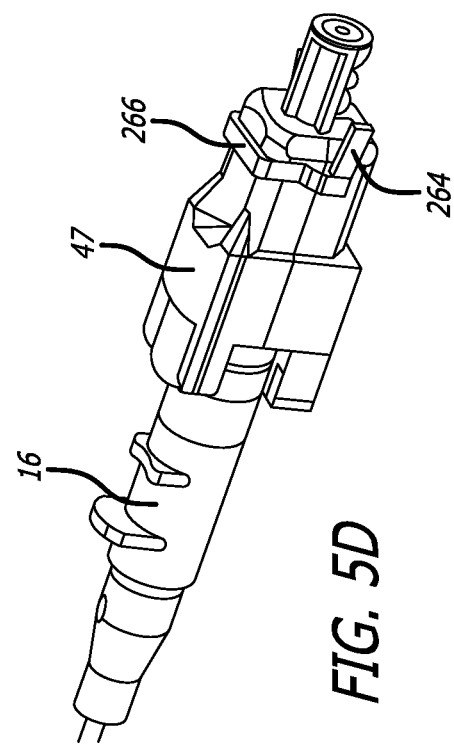
Figure 5E:
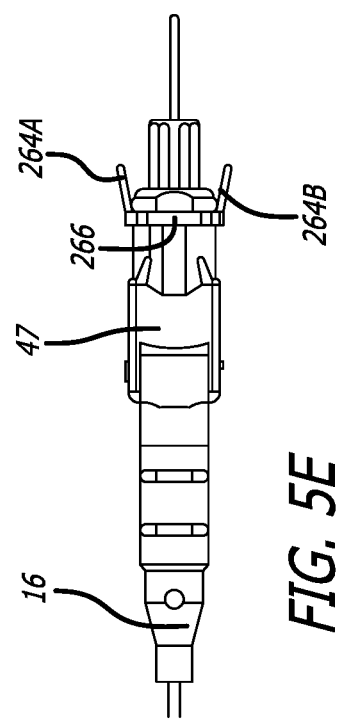

In an embodiment, as shown in FIGS. 5B-5C, the indexing fingers 264 are integrally molded with the safety body 47 to form a single structure. In an embodiment, as shown in FIGS. 5C-5D, the indexing fingers 264 are formed as a separate structure from that of the safety body 47 and coupled thereto. In an embodiment, the indexing finger 264 can be formed from the same material as the safety body 47 or from a different material. Exemplary materials include plastic, polymers, metals, alloys, or any suitably resilient material. As shown in FIGS. 5C-D, the indexing fingers 264 extend from a collar 266. The collar 266 can extend at least partially around a portion of the safety assembly body 47. In an embodiment, the collar 266 extends from a first side to a second side of the safety assembly body 47. In an embodiment the collar 266 encircles the safety assembly body 47 to surround the longitudinal axis of the body 47. In an embodiment, the safety body 47 includes one or more recesses configured to retain a portion of the collar 266, indexing finger 264, or combinations thereof, to further secure the collar 266/indexing fingers 264 thereto.

Advantageously, the catheter insertion device 10 including rigid actuator abutments 276, housing abutments 260, and flexible indexing fingers 264 requires less moving parts. This simplifies manufacture and assembly of the catheter insertion device 10 as well as providing a more robust operation of the catheter insertion device 10. Further, by forming the indexing fingers as part of the safety body 47, the manufacture and assembly of the catheter insertion device 10 is further simplified. In the alternative that the indexing fingers are formed as a separate structure, and optionally of a separate material, the amount of spring forces or resistance to deflection, can be more accurately defined or modified. This allows the catheter insertion device 10 to balance the actuator button 68 and catheter advancement forces.

As shown in FIGS. 6A-6D, in an embodiment, the catheter insertion device 10 can include a combination of flexible housing tabs 60 and rigid actuator abutments 276. Other combinations are also contemplated for example rigid housing abutments 260 and flexible actuator tabs 76. As described herein, the catheter insertion device 10 includes a housing 12 and an actuator assembly 20 that includes a button 68 coupled to an actuator body 66. The actuator body 66 extends proximally, substantially to a proximal end of the housing 12, and includes a top wall 228, a first side wall 226A, and a second side wall 226B. The top wall 228 extends below the top wall 28 of the housing 12 and above the catheter assembly, which includes the catheter 14, catheter hub 16, and safety assembly 46. The first side wall 226A, and the second side wall 226B extend from the top wall 228, inside of the side walls 26 of the housing 12, and outside of the catheter assembly. The top wall 228, first side wall 226A, and second side wall 226B can create an inverse channel within which the catheter assembly can travel along a longitudinal axis. Optionally, the actuator body 66 can include a rounded or chamfered portion to fit snuggly within the interior cavity 50 of the housing 12.

In an embodiment, one of the first side wall 226A and the second side wall 226B can include a plurality of notches 274 extending upwards from a lower edge of the side wall to define an abutment surface 276 on a distally facing surface of the notch 274. As shown, the notches 274 define a substantially rectangular shape when viewed from a side profile, however it will be appreciated that notches 274 can also define other shapes, such as triangular or semi-circular, and still remain within the scope of the present invention. In an embodiment, the side walls 226A, 226B can include a plurality of apertures disposed therein to define the distally facing abutment surfaces 276.

Figure 6A:
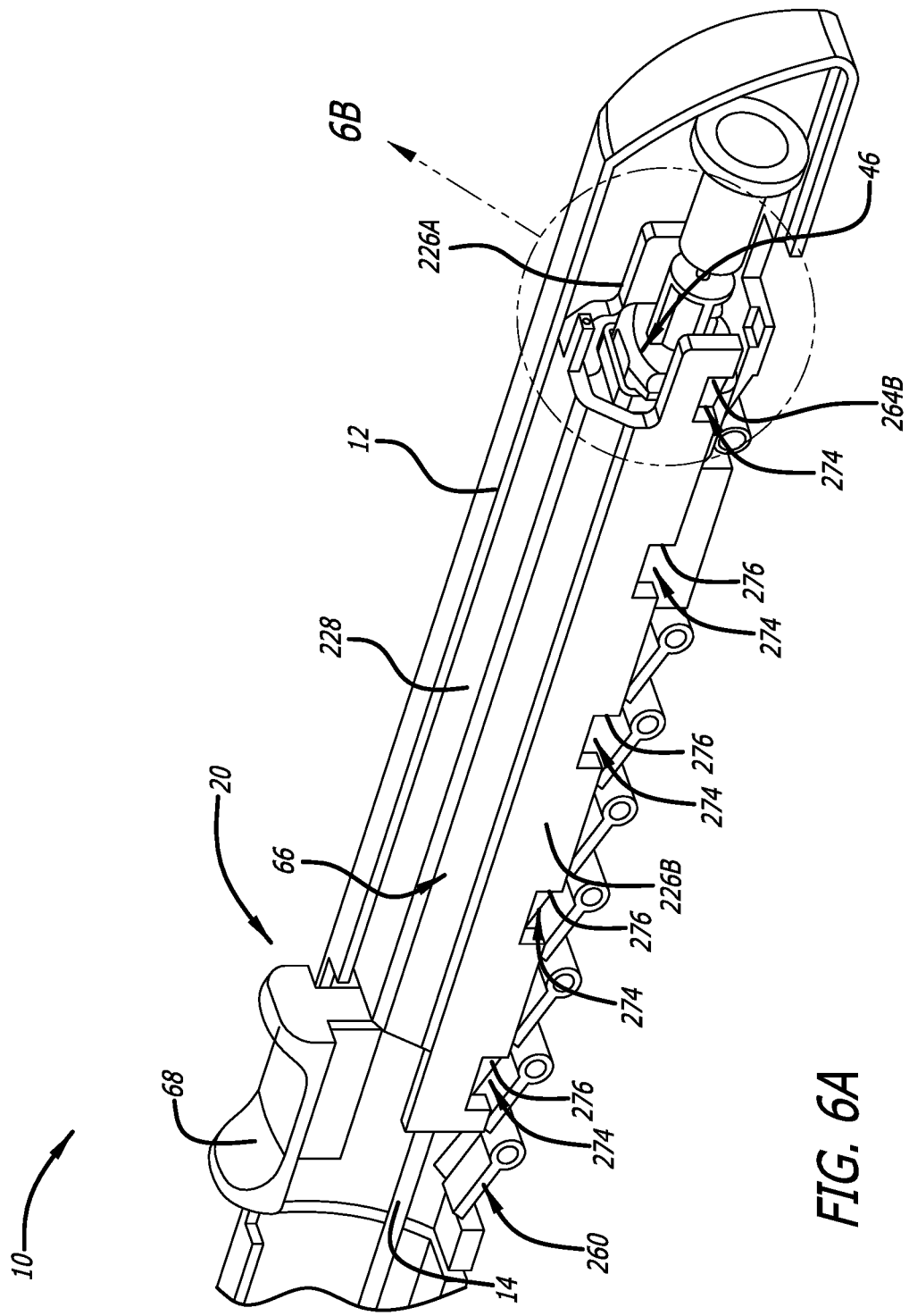
FIG. 6A shows a perspective cutaway view of a proximal portion of a catheter insertion device, in accordance with embodiments disclosed herein.
Figure 6B:
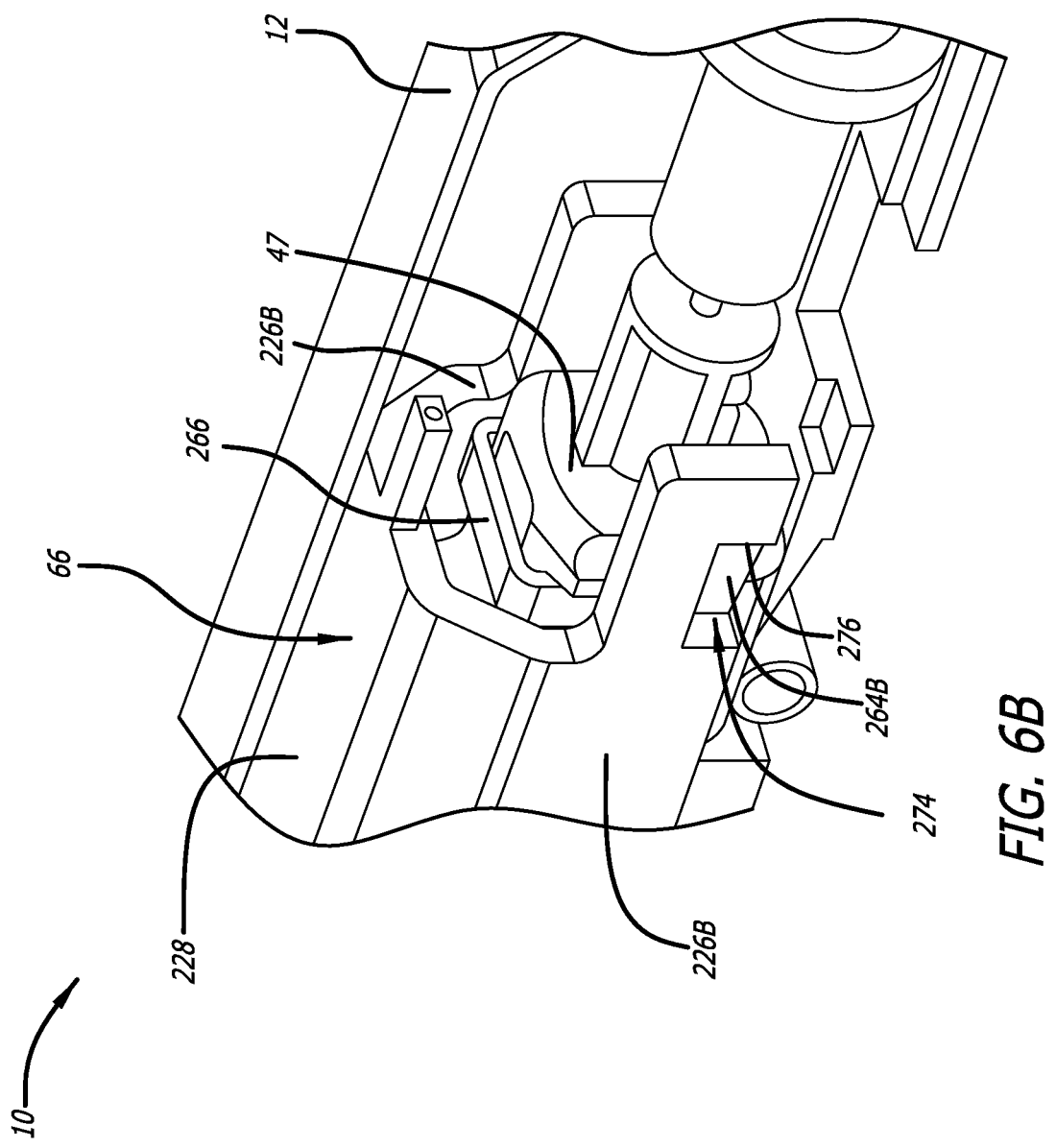
FIG. 6B shows a close up view of the catheter insertion device of FIG. 6A, in accordance with embodiments disclosed herein.

FIG. 6B shows a close up view of the proximal end of the catheter insertion device 10 shown in FIG. 6A. As shown, the safety assembly body 47 includes a collar 266 that supports the first indexing finger 264A and the second indexing finger 264B. In an embodiment, the indexing fingers 264A, 264B can also be formed as a single piece with the safety body 47, as described herein. The collar 266 engages a portion of the safety body 47 and supports the indexing fingers 264A, 264B in an outwardly biased position. The first indexing finger 264A extends from a first side portion of the safety body 47, and the second indexing finger 264B extends from a second side portion of the safety body 47, opposite the first side portion. The indexing fingers 264A, 264B are aligned with the plurality of notches 274 so that a proximal tip of the indexing fingers 264 engage a distally facing abutment surface 276. The housing 12 further includes a plurality of housing tabs 60 that engage a lower portion of the safety body 47 to prevent proximal movement thereof, as described herein.

In use, the catheter insertion device 10 includes an actuator button 68 disposed in the retracted, starting position, for example, as shown in FIG. 5A. A user can manipulate the actuator button 68 to move the actuator assembly 20 in a distal direction from the starting position, to an extended position (FIG. 6C). As shown in FIG. 6C, a proximal abutment surface 276, of the first side wall 226A engages the first indexing fingers 264A, and a proximal abutment surface 276, e.g. a first abutment surface 276a, of the second side wall 226B engages the second indexing finger 264B. Advancing the actuator assembly 20 to the extended position distally advances the catheter assembly. The catheter assembly is advanced distally of a proximal tab 60. The tab 60 deflects downwards to allow the catheter assembly to pass, before returning to the undeflected position to engage surface 64 on the safety assembly 46. This prevents proximal movement of the catheter assembly.

As shown in FIG. 6D, the actuator assembly 20 is then moved proximally, from the extended position to the retracted, starting position. As the actuator body 66 moves proximally, the first indexing finger 264A and the second indexing finger 264B deflect to allow a portion of the side walls 226A, 226B to pass until an adjacent notch 274 aligns with the indexing fingers 264A, 264B allowing the indexing fingers to engage an adjacent abutment surface 276, e.g. a second abutment surface 276b. The cycle then repeats to advance the catheter assembly distally in a stepwise manner.

Advantageously, embodiments including the actuator body 66 defining an inverse channel require relatively less moving parts to facilitate manufacture and assembly. Further, the actuator body 66 provides a channel within which the catheter assembly can travel. The device 10 also provides dual contact points between the actuator assembly 20 and the safety assembly 46 that are disposed evenly about a central axis. These features provide an even application of force and prevents the catheter assembly, or portions thereof, from pivoting relative to the longitudinal axis during distal advancement. This prevents the indexing mechanism from jamming and provides a more robust operation.

In an embodiment, the catheter insertion device 10 can include a lockout device. As described in more detail herein, the lockout device can include one of a button, collar, slider or tab. In general, the lockout device can selectively restrict the stepwise advancement mechanism to inhibit the catheter insertion device 10 from advancing beyond an initial stage, while still allowing some movement of the catheter 14 relative to the needle 18. This allows a user to break any adhesion between the catheter 14 and the needle 18 that may have occurred during manufacture, prior to deployment of the catheter 14. The user can then selectively unlock the lockout device to allow the catheter insertion device 10 to cycle through a first stage. Breaking the adhesion ensures a smooth, uniform advancement through each stage of the stepwise advancement.

Figure 7A:
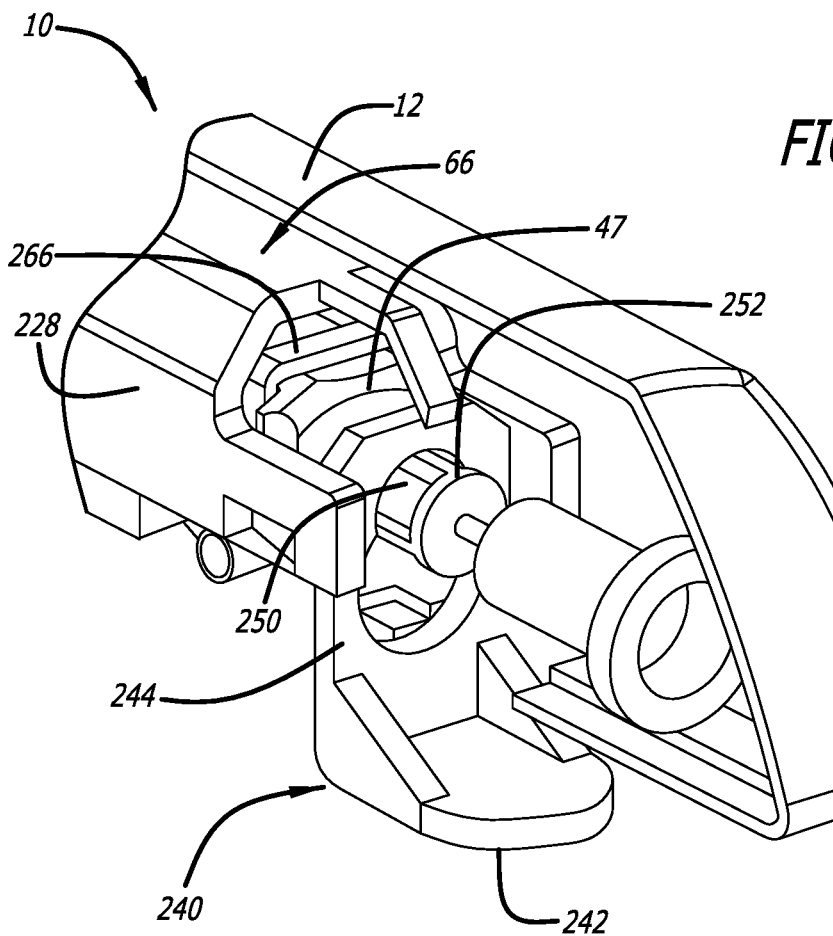
FIG. 7A shows a perspective cutaway view of a catheter insertion device including a lockout device, in accordance with embodiments disclosed herein.
Figure 7B:
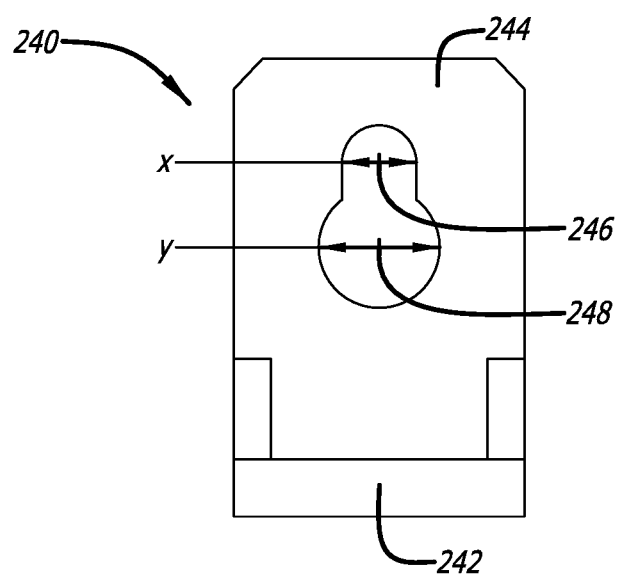
FIG. 7B shows a proximal end view of the lockout device of FIG. 7A, in accordance with embodiments disclosed herein.

As shown in FIGS. 7A-7B, in an embodiment, the catheter insertion device 10 includes a lockout button 240 that includes an actuator surface 242 coupled with an engagement arm 244, and can transition between a locked position (e.g. FIG. 7A) and an unlocked position. The engagement surface 244 includes a first, substantially circular aperture 246 defining a first diameter (x) and a second, substantially circular aperture 248 defining a second diameter (y). As shown in FIG. 7B, the first aperture 246 and second aperture 248 can communicate to define a "keyhole" shaped aperture. As shown in FIG. 7A, the safety assembly body 47 includes a cylindrical anchor portion 250, extending proximally therefrom, and defining a substantially circular cross-section. The cross-section of the anchor 250 defines a diameter that is the same or less than the diameter (x) of the first aperture 246. The anchor 250 also includes a flange 252 extending radially from a proximal end of the anchor portion 250. The flange 252 defines a diameter that is larger than the diameter (x) of the first aperture 246 but smaller than the diameter (y) of the second aperture 248.

As shown in FIG. 7A, the lockout button 240 is deployed in the locked position where the anchor 250 is disposed within the first aperture 246 and the flange 252 abuts against the engagement arm 244. In this position the longitudinal movement of the safety assembly 46, as well as catheter 14 and catheter hub 16, are restricted.

In an embodiment, the longitudinal movement of the safety assembly 46 is restricted to a distance that is less than the longitudinal distance between adjacent housing abutments 260, adjacent actuator abutments 276, adjacent housing tabs 60, or adjacent actuator tabs 76. In an embodiment, the longitudinal movement of the safety assembly 46 is restricted to a distance that is substantially half the longitudinal distance between adjacent housing abutments 260, adjacent actuator abutments 276, adjacent housing tabs 60, or adjacent actuator tabs 76. In an embodiment, the longitudinal movement of the safety assembly 46 is restricted to a longitudinal distance of between 1 mm to 3 mm, however greater or lesser distances are also contemplated.

With the lockout button 240 in the locked position a user is able to move the actuator assembly 20 so as to move the catheter 14 relative to the needle 18, but is not able to move the catheter assembly 20 beyond a first step of the stepwise advancement, i.e. not as far as the next tab 60, or abutment 260. This movement breaks loose any adhesion between the catheter 14 and the needle 18 that may have formed during manufacture, assembly, transport or storage. When the user is ready to advance the catheter, the lockout button 240 can be transitioned to the unlocked position, where the anchor 250 is disposed within the second aperture 248 and the flange 252 can pass through the aperture 248. This allows the actuator assembly 20 to advance the catheter assembly in a stepwise manner, as described herein. It will be appreciated that the configuration and location of the lockout button 240 and apertures 246, 248 can vary from that shown in FIGS.

7A-7B without departing from the spirit of the invention. For example, the orientation of the apertures 246, 248 can be reversed so that the unlocked position of the lockout button 240 is an extended position and a locked position is a retracted position. Similarly, the location of the button 240 can extend from a lower, upper, or side surface of the housing 12.

Advantageously, the lockout button 240 allows the user to break loose any adhesion between the catheter 14 and the needle 18 that may have formed during assembly, transport or storage. This loosens the movement between the catheter 14 and the needle 18 prior to use and ensures a smooth, uniform and controlled action when the catheter 14 is deployed.

As shown in FIGS. 8A-8D, in an embodiment, the catheter insertion device 10 includes a lockout collar 280 that restricts movement of the actuator button 68, the actuator assembly, and the catheter assembly engaged therewith. The lockout collar 280 is disposed on an outer surface of the housing 12 and encircles the housing 12 about the longitudinal axis. In an embodiment, the collar 280 encircles a portion of the housing 12 such that it can be detached from the catheter insertion device 10 by sliding the collar 280 perpendicular to the longitudinal axis. The housing 12 includes one or more protrusions, for example a first protrusion 282 and a second protrusion 284, extending from an outer surface thereof. The lockout collar 280 can slide relative to the first protrusion 282 and a second protrusion 284 to transition between a locked position and an unlocked position.

Figure 8A:
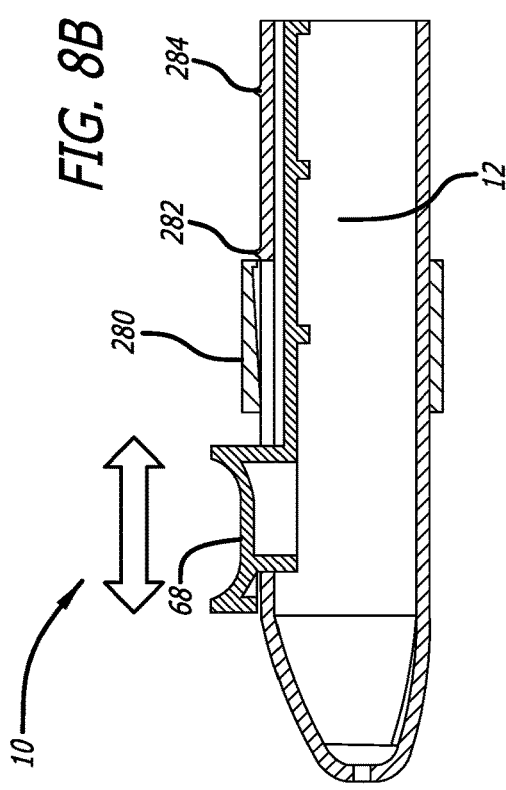
FIGS. 8A-8D show various views of a catheter insertion device including a lockout device, in accordance with embodiments disclosed herein.
Figure 8B:
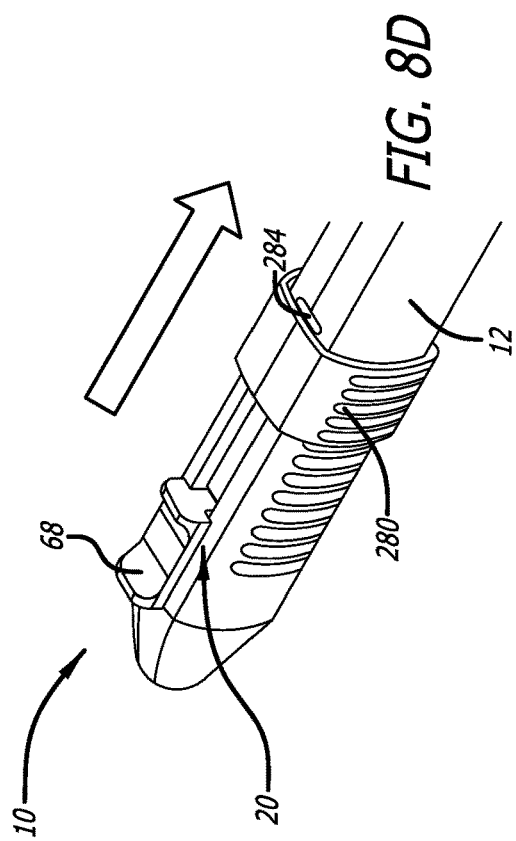
Figure 8C:
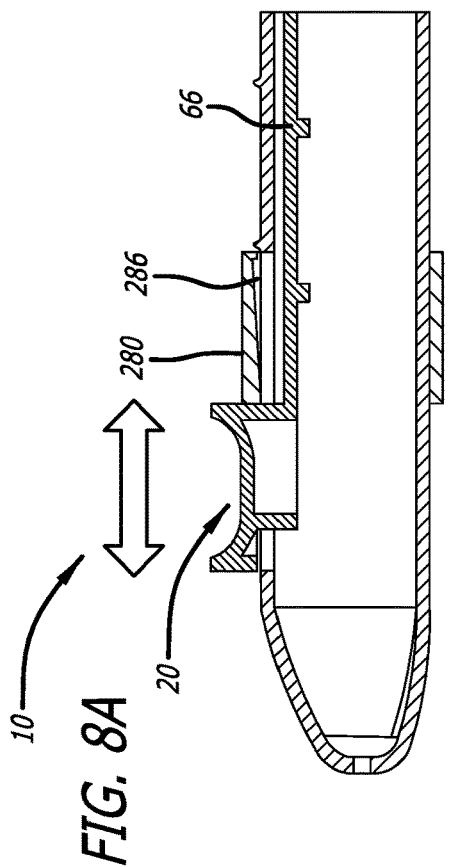
Figure 8D:
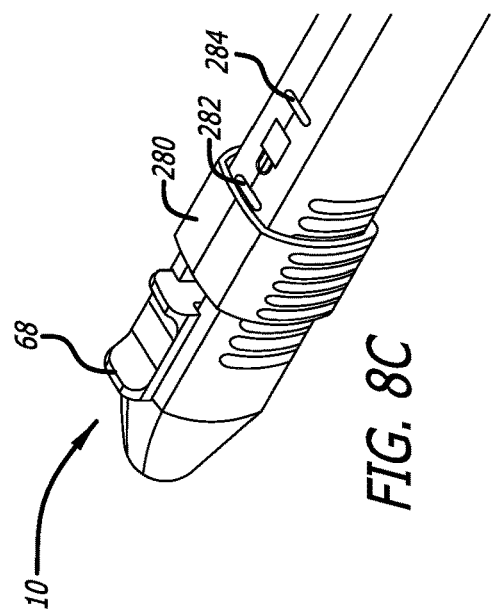

As shown in FIGS. 8A-8B, the lockout collar 280 can be disposed in a locked position where the collar 280 is disposed between the first protrusion 282 and the actuator button 68 so as to cover at least a portion of the opening 32. In the locked position, the longitudinal movement of the actuator assembly 20, and the catheter assembly engaged therewith, is restricted.

In an embodiment, the longitudinal movement of the actuator assembly 20 is restricted to a distance that is less than the length of the opening 32. In an embodiment, the longitudinal movement of the actuator assembly 20 is restricted to a distance that is substantially half of the length of the opening 32. In an embodiment, the longitudinal movement of the actuator assembly 20 is restricted to a distance that is less than the longitudinal distance between adjacent housing abutments 260, adjacent actuator abutments 276, adjacent housing tabs 60, or adjacent actuator tabs 76. In an embodiment, the longitudinal movement of the actuator assembly 20 is restricted to a distance that is substantially half of the longitudinal distance between adjacent housing abutments 260, adjacent actuator abutments 276, adjacent housing tabs 60, or adjacent actuator tabs 76. In an embodiment, the longitudinal movement of the actuator assembly 20 is restricted to a distance of between about 1 mm to about 3 mm, however greater or lesser distances are also contemplated.

With the lockout collar 280 in the locked position, a user is able to move the actuator assembly 20 so as to move the catheter 14 relative to the needle 18, but is not able to move the catheter assembly beyond a first step of the stepwise advancement, i.e. not as far as the next housing tab 60, or housing abutment 260. This movement breaks loose any adhesion between the catheter 14 and the needle 18 that may have formed during assembly, transport or storage. When the user is ready to advance the catheter 14, the lockout collar 280 can be removed, or slid to the unlocked position, i.e. between the first protrusion 282 and the second protrusion 284 where the collar 280 does not cover the opening 32. This allows the actuator assembly 20 to advance the catheter assembly in a stepwise manner, as described herein.

In an embodiment, the first protrusion 282 is disposed at one of a distal end or a proximal end of the opening 32 and configured to restrict movement of the collar 280 relative to the housing along a longitudinal axis to maintain the lockout collar 280 in the locked position. When ready for use, the user can slide the lockout collar 280 over the first protrusion 282 to the "unlocked" position. In an embodiment, the collar 280 further includes a skive 286 on an inner surface of the collar 280 to facilitate moving the lockout collar 280 over the first protrusion 282.

The second protrusion 284 can be positioned a distance from the first protrusion 282 so that the lockout collar 280 can be received therebetween. In an embodiment, the first protrusion 282 and the second protrusion 284 protrude a similar height from the outer surface of the housing 12. Optionally, the lockout collar 280 can be slid past the second protrusion 284 and be removed from the catheter insertion device 10. In an embodiment, the second protrusion 284 protrudes further from the outer surface of the housing 12 than the first protrusion 282, and prevents the lockout collar 280 from being removed from the catheter insertion device 10. Optionally, the lockout collar 280 includes a contrasting color, tactile features, gripping features, alphanumeric symbols, icons, or combinations thereof, to distinguish the lockout collar 280 from that of the housing 12 and notify the user that the catheter insertion device 10 is in the locked or unlocked position.

As shown in FIGS. 8A-8D, the lockout collar 280, first protrusion 282, and second protrusion 284 are disposed between the actuator button 68 and a proximal end of the catheter insertion device 10 such that the collar 280 is slid in a proximal direction to the "unlocked" position. It will be appreciated, however, that the orientation of the actuator button 68, lockout collar 280, first protrusion 282, and second protrusion 284 can be disposed in other configurations without departing from the spirit of the invention. For example, the collar 280 can be slid in a distal direction to move from the locked position to the unlocked position and optionally be removed from the catheter insertion device 10.

Figure 9A:
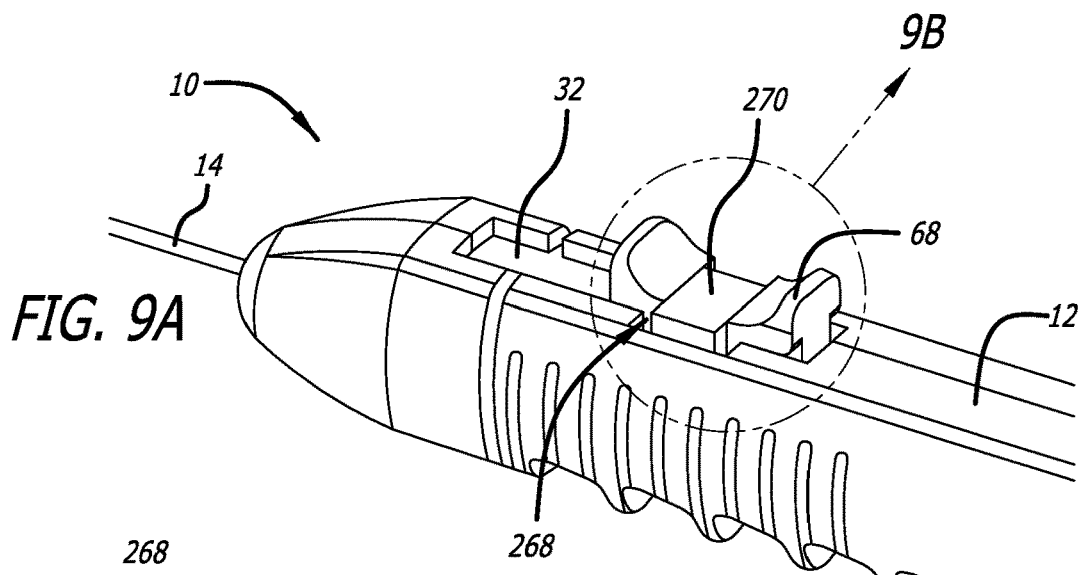
FIGS. 9A-9C show various views of a catheter insertion device including a lockout device, in accordance with embodiments disclosed herein.
Figure 9B:
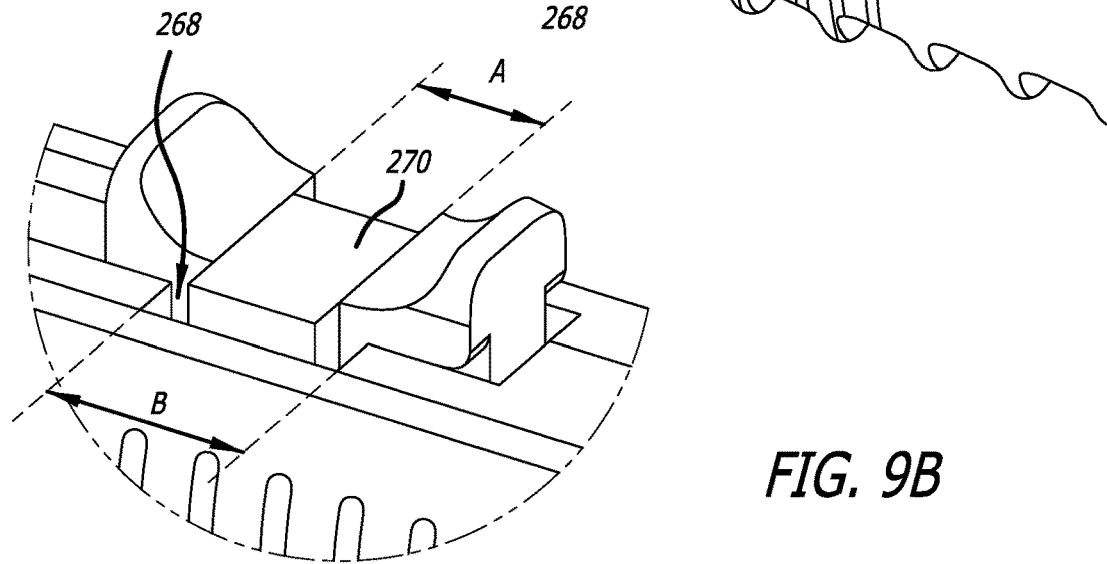
Figure 9C:
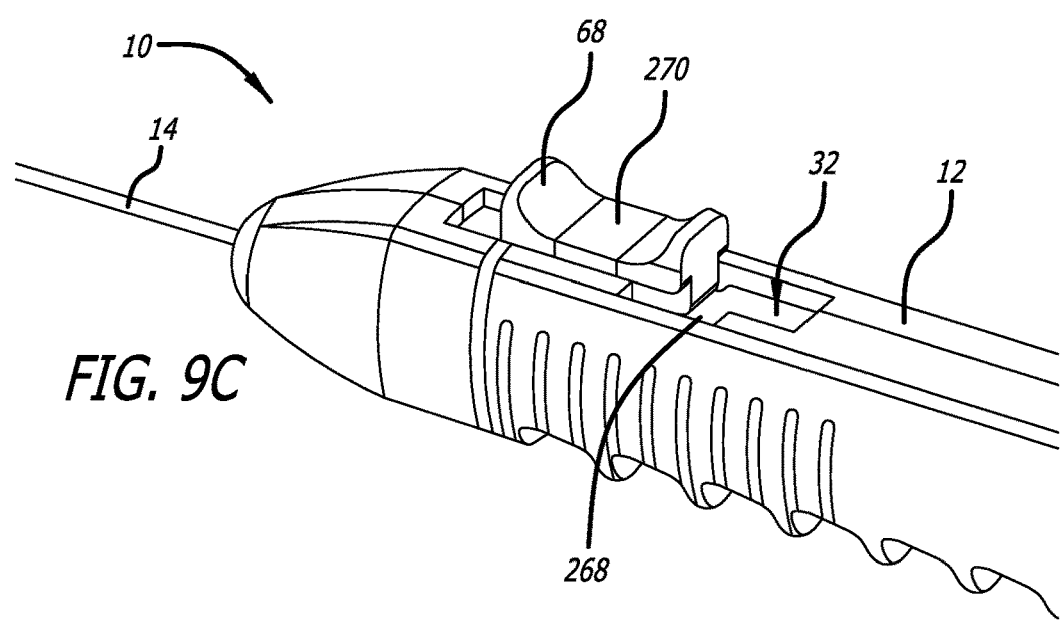

As shown in FIGS. 9A-9C, in an embodiment, the catheter insertion device 10 can include a lockout slider 270 that can transition between a locked position, to restrict the movement of the actuator button 68 (FIG. 9A), and an unlocked position to allow the actuator assembly to move along the elongate opening 32 (FIG. 9C). In an embodiment, the lockout slider 270 can be slid perpendicular to the longitudinal axis, i.e. the direction of travel of the actuator assembly 20, to engage notch 268. However, it will be appreciated that other orientations of slider 270 and notch 268 are also contemplated.

A longitudinal width of the slider 270 can define a first width (a). A longitudinal width of the notch 268 can define a second width (b). In an embodiment, the width of the slide (a) is less than a width of the notch (b). The notch 268 can engage the slider 270 to restrict the movement of the actuator assembly 20. As shown in FIG. 9A, the lockout slider 270 is deployed in the locked position where the slider 270 engages notch 268. In this position the longitudinal movement of the safety actuator assembly 20 and the catheter assembly engaged therewith, are restricted.

In an embodiment, the longitudinal movement of the actuator assembly 20 is restricted to a distance that is less than the length of the opening 32. In an embodiment, the longitudinal movement of the actuator assembly 20 is restricted to a distance that is substantially half of the length of the opening 32. In an embodiment, the longitudinal movement of the actuator assembly 20 is restricted to a distance that is less than the longitudinal distance between adjacent housing abutments 260, adjacent actuator abutments 276, adjacent housing tabs 60, or adjacent actuator tabs 76. In an embodiment, the longitudinal movement of the actuator assembly 20 is restricted to a distance that is substantially half of the longitudinal distance between adjacent housing abutments 260, adjacent actuator abutments 276, adjacent housing tabs 60, or adjacent actuator tabs 76. In an embodiment, the longitudinal movement of the actuator assembly 20 is restricted to a distance of between about 1 mm to about 3 mm, however greater or lesser distances are also contemplated.

With the lockout slider 270 in the locked position a user is able to move the actuator assembly 20 so as to move the catheter 14 relative to the needle 18, but is not able to move the catheter assembly beyond a first step of the stepwise advancement, i.e. not as far as the next housing tab 60, or housing abutment 260. This movement breaks loose any adhesion between the catheter 14 and the needle 18 that may have formed during assembly, transport or storage. When the user is ready to advance the catheter, the lockout slider 270 can be moved to the unlocked position, where the actuator assembly 20 can advance the catheter assembly in a stepwise manner, as described herein.

FIGS. 10A-10D show an embodiment of the catheter insertion device 10 including a lockout tab 290. FIG. 10A shows a plan view of the catheter insertion device 10 and FIG. 10B shows a cutaway side view of the catheter insertion device 10 with the lockout tab 290 in the "locked" position, i.e. disposed within guide slot 77 of housing 12. To note, a proximal end 74 of the actuator body 66 includes a guide pin 75 that is received within slot 77 to stabilize the proximal end 74 of the actuator body 66. Further details of which can be found in WO 2018/170349, which is incorporated by reference in its entirety herein.

FIG. 10C shows a cutaway plan view of the catheter insertion device 10 and FIG. 10D shows a cutaway side view of the catheter insertion device 10 with the lockout tab 290 in the "unlocked" position, i.e. removed from slot 77. In an embodiment, the catheter insertion device 10 includes a first slot 77A disposed on a first of the housing 12 and a second slot 77B disposed on a second side of the housing 12, opposite the first side. In an embodiment, the lockout tab 290 can be disposed through either of the first slot 77A or the second slot 77B. In an embodiment, the lockout tab 290 can be disposed through both of the first and second slots 77A, 77B.

As shown in FIG. 10B, in the "locked" position, the lockout tab 290 is disposed between a proximal end of the actuator assembly 20 and an inner surface of the housing 12, i.e. between the guide pin 75 and a proximal edge of the slot 77, to restrict movement of the actuator assembly 20, and catheter 14. The longitudinal width (t) of the lockout tab 290 can be less than the longitudinal length of the slots 77A, 77B, and can be modified to vary the amount of restriction imposed on the actuator assembly 20.

In an embodiment, the longitudinal movement of the actuator assembly 20 is restricted to a distance that is less than the longitudinal length of the first slot 77A or the second slot 77B. In an embodiment, the longitudinal movement of the actuator assembly 20 is restricted to a distance that is substantially half of the longitudinal length of the first slot 77A or the second slot 77B. In an embodiment, the longitudinal movement of the actuator assembly 20 is restricted to a distance that is less than the longitudinal distance between adjacent housing abutments 260, adjacent actuator abutments 276, adjacent housing tabs 60, or adjacent actuator tabs 76. In an embodiment, the longitudinal movement of the actuator assembly 20 is restricted to a distance that is substantially half of the longitudinal distance between adjacent housing abutments 260, adjacent actuator abutments 276, adjacent housing tabs 60, or adjacent actuator tabs 76. In an embodiment, the longitudinal movement of the actuator assembly 20 is restricted to a distance of between about 1 mm to about 3 mm, however greater or lesser distances are also contemplated.

With the lockout button 240 in the locked position a user is able to move the actuator assembly 20 so as to move the catheter 14 relative to the needle 18, but is not able to move the catheter assembly beyond a first step of the stepwise advancement, i.e. not as far as the next tab 60, or abutment 260. This movement breaks loose any adhesion between the catheter 14 and the needle 18 that may have formed during manufacture, assembly, transport or storage. When the user is ready to advance the catheter, the lockout tab 290 can be removed. This allows the actuator assembly 20 to advance the catheter assembly in a stepwise manner, as described herein. Optionally, the lockout device, e.g. the lockout tab 290, can include a contrasting color, tactile features, gripping features, alphanumeric symbols, icons, or combinations thereof, to distinguish the lockout tab 290 from that of the housing 12 and notify the user that the catheter insertion device 10 is in the locked or unlocked position.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A catheter placement device, comprising:
   a housing;
   a needle extending from a distal end of the housing;
   a catheter assembly disposed coaxially over the needle, including a catheter supported by a catheter hub, and a safety assembly including a first indexing finger; and
   an actuator assembly configured to transition longitudinally between a first position and a second position, the actuator assembly comprising:
   an actuator button extending through an elongate opening in the housing; and
   an actuator body including a plurality of actuator abutments,
   wherein the first indexing finger engages a first actuator abutment of the plurality of actuator abutments and the actuator assembly distally advances the catheter assembly in a stepwise manner as the actuator assembly moves between the first position and the second position, and
   wherein the first indexing finger is integrally molded with the safety assembly to form a single structure, the first indexing finger configured to flexibly deform as the actuator body moves from the second position to the first position.

2. The catheter placement device according to claim 1, wherein the first indexing finger is supported by a collar and is formed as a separate structure from the safety assembly, the collar being coupled to the safety assembly, and the first indexing finger configured to flexibly deform as the actuator body moves from the second position to the first position.

3. The catheter placement device according to claim 1, wherein the housing includes a plurality of housing tabs that engage the safety assembly to prevent proximal movement thereof.

4. The catheter placement device according to claim 1, wherein the housing includes a plurality of housing abutments that engage a second indexing finger extending from the safety assembly to prevent proximal movement thereof.

5. The catheter placement device according to claim 1, wherein the actuator body includes a top wall, a first side wall, and a second side wall that define an inverse channel through which the catheter assembly moves along a longitudinal axis.

6. The catheter placement device according to claim 5, wherein one of the first side wall or the second side wall includes a plurality of notches that define the plurality of actuator abutments.

7. The catheter placement device according to claim 5, wherein one of the first side wall or the second side wall includes a plurality of apertures that define the plurality of actuator abutments.

8. The catheter placement device according to claim 1, wherein the housing includes a first door and a second door disposed at a distal end thereof and configured to pivot through a horizontal plane between an open position and a closed position.

9. The catheter placement device according to claim 8, wherein the housing includes a first housing half and a second housing half joined along a longitudinally vertical plane, the first door hingedly coupled to the first housing half and the second door hingedly coupled to the second housing half.

10. The catheter placement device according to claim 1, wherein the housing includes a first hinged door disposed at a distal end thereof and configured to pivot through a vertical plane.

11. The catheter placement device according to claim 10, wherein the housing includes a first housing half and a second housing half joined along a longitudinally horizontal plane, the first door hingedly coupled to the first housing half.

12. A catheter placement device, comprising:
a housing;
a needle extending from a distal end of the housing;
a catheter assembly disposed coaxially over the needle, including a catheter supported by a catheter hub, and a safety assembly including a first indexing finger; and
an actuator assembly configured to transition longitudinally between a first position and a second position, the actuator assembly comprising:
an actuator button extending through an elongate opening in the housing; and
an actuator body including a plurality of actuator abutments,
wherein the first indexing finger engages a first actuator abutment of the plurality of actuator abutments and the actuator assembly distally advances the catheter assembly in a stepwise manner as the actuator assembly moves between the first position and the second position, and
wherein the first indexing finger is supported by a collar and is formed as a separate structure from the safety assembly, the collar being coupled to the safety assembly, and the first indexing finger configured to flexibly deform as the actuator body moves from the second position to the first position.

13. The catheter placement device according to claim 12, wherein the housing includes a plurality of housing tabs that engage the safety assembly to prevent proximal movement thereof.

14. The catheter placement device according to claim 12, wherein the housing includes a plurality of housing abutments that engage a second indexing finger extending from the safety assembly to prevent proximal movement thereof.

15. The catheter placement device according to claim 12, wherein the actuator body includes a top wall, a first side wall, and a second side wall that define an inverse channel through which the catheter assembly moves along a longitudinal axis.

16. The catheter placement device according to claim 12, wherein the housing includes a first door and a second door disposed at a distal end thereof and configured to pivot through a horizontal plane between an open position and a closed position.

* * * * *